(12) United States Patent
Blokhin et al.

(10) Patent No.: US 7,253,207 B2
(45) Date of Patent: *Aug. 7, 2007

(54) QUINONES AS DISEASE THERAPIES

(75) Inventors: Andrei V. Blokhin, Madison, WI (US); Benjamin Frydman, Madison, WI (US); Laurence J. Marton, Palo Alto, CA (US); Karen M. Neder, Madison, WI (US); Jerry Shunneng Sun, Madison, WI (US)

(73) Assignee: Cellgate, Inc., Redwood City, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 10/909,978

(22) Filed: Aug. 2, 2004

(65) Prior Publication Data
US 2005/0010060 A1    Jan. 13, 2005

Related U.S. Application Data

(62) Division of application No. 10/139,978, filed on May 6, 2002, now Pat. No. 6,809,176, which is a division of application No. 09/562,980, filed on Apr. 27, 2000, now Pat. No. 6,482,943.

(60) Provisional application No. 60/131,842, filed on Apr. 30, 1999.

(51) Int. Cl.
*A61K 31/35* (2006.01)
*C07D 311/92* (2006.01)

(52) U.S. Cl. .................. 514/454; 514/455; 530/300; 549/389; 549/458; 552/290; 552/291; 552/292; 552/293

(58) Field of Classification Search ............... 530/300; 552/290, 291, 292, 293; 514/454, 455; 549/389, 549/458
See application file for complete search history.

(56) References Cited

U.S. PATENT DOCUMENTS

| | | | |
|---|---|---|---|
| 4,035,174 A | 7/1977 | Grier et al. |
| 4,092,432 A | 5/1978 | Bjorklund et al. |
| 4,153,567 A | 5/1979 | Kluger et al. |
| 4,273,706 A | 6/1981 | Chapman et al. |
| 4,491,651 A | 1/1985 | Naiman |
| 4,537,601 A | 8/1985 | Naiman |
| 4,577,636 A | 3/1986 | Spears |
| 4,590,288 A | 5/1986 | Klemann |
| 4,642,344 A | 2/1987 | Hajek et al. |
| 4,698,446 A | 10/1987 | Lai et al. |
| 4,767,611 A | 8/1988 | Gordon |
| 4,849,207 A | 7/1989 | Sakata et al. |
| 4,898,870 A | 2/1990 | Narutomi et al. |
| 4,935,449 A | 6/1990 | Bey et al. |
| 4,959,356 A | 9/1990 | Miura et al. |
| 4,963,565 A | 10/1990 | Gangadharam |
| 4,992,257 A | 2/1991 | Bonnett et al. |
| 4,996,312 A | 2/1991 | Sakata et al. |
| 5,007,437 A | 4/1991 | Sterzer |
| 5,021,409 A | 6/1991 | Murrer et al. |
| 5,021,571 A | 6/1991 | Mease et al. |
| 5,080,998 A | 1/1992 | Irving et al. |
| 5,120,843 A | 6/1992 | McCall et al. |
| 5,210,239 A | 5/1993 | Abe et al. |
| 5,217,964 A | 6/1993 | Edwards et al. |
| 5,284,647 A | 2/1994 | Niedballa et al. |
| 5,344,435 A | 9/1994 | Turner et al. |
| 5,354,782 A | 10/1994 | Edwards et al. |
| 5,354,858 A | 10/1994 | Morgan et al. |
| 5,374,658 A | 12/1994 | Lau |
| 5,385,942 A | 1/1995 | Abe et al. |
| 5,401,443 A | 3/1995 | Nagano et al. |
| 5,413,719 A | 5/1995 | Sivakumar et al. |
| 5,424,305 A | 6/1995 | Skalkos et al. |
| 5,434,145 A | 7/1995 | Edwards et al. |
| 5,498,522 A | 3/1996 | Porter |
| 5,512,559 A | 4/1996 | Skalkos et al. |
| 5,516,807 A | 5/1996 | Hupe et al. |
| 5,541,230 A | 7/1996 | Basu et al. |
| 5,563,262 A | 10/1996 | Morgan et al. |
| 5,587,394 A | 12/1996 | Morgan et al. |
| H1633 H | 2/1997 | Hiebert et al. |
| 5,599,686 A | 2/1997 | DeFeo-Jones et al. |
| 5,606,053 A | 2/1997 | Prashad et al. |
| 5,607,574 A | 3/1997 | Hart |

(Continued)

FOREIGN PATENT DOCUMENTS

| | | |
|---|---|---|
| DE | 1 295 826 | 5/1969 |
| EP | 0 255 679 A2 | 2/1988 |
| EP | 0 255 679 A3 | 2/1988 |
| EP | 0 255 679 B1 | 2/1988 |
| JP | 07-277964 A | 10/1995 |
| JP | 05-032902 A | 2/1996 |
| JP | 09-235280 A | 9/1997 |
| WO | WO-94/07894 A1 | 4/1994 |
| WO | WO 94/08578 A2 | 4/1994 |
| WO | WO-95/18091 A1 | 7/1995 |

(Continued)

OTHER PUBLICATIONS

Cassis, R. et al. (Mar.-Apr. 1982). "Studies on Quinones. VIII(1). The Application of Michael Adducts from 2-Hydroxy-1,4-naphthoquinones for the Preparation of Dihydronaphthopyrandiones (2)," *Journal of Heterocyclic Chemistry* 19:381-384.

(Continued)

*Primary Examiner*—Elli Peselev
(74) *Attorney, Agent, or Firm*—Morrison & Foerster LLP

(57) ABSTRACT

Novel quinones are provided, as well as compositions comprising these novel quinones. Methods of using the novel quinones in treatment of various indications including cancer are also provided.

21 Claims, 17 Drawing Sheets

U.S. PATENT DOCUMENTS

| | | | |
|---|---|---|---|
| 5,608,061 A | 3/1997 | Ciszewski et al. |
| 5,612,478 A | 3/1997 | Xu et al. |
| 5,627,215 A | 5/1997 | Frei et al. |
| 5,641,773 A | 6/1997 | Pardee et al. |
| 5,646,188 A | 7/1997 | Gilad et al. |
| 5,654,287 A | 8/1997 | Prakash et al. |
| 5,672,202 A | 9/1997 | Stirling et al. |
| 5,674,900 A | 10/1997 | Ubillas et al. |
| 5,677,349 A | 10/1997 | Gilad et al. |
| 5,677,350 A | 10/1997 | Frydman |
| 5,681,837 A | 10/1997 | Bergeron |
| 5,693,632 A | 12/1997 | Morgan et al. |
| 5,707,532 A | 1/1998 | Guerro et al. |
| 5,744,453 A | 4/1998 | Mintz et al. |
| 5,763,388 A | 6/1998 | Lightsey et al. |
| 5,763,625 A | 6/1998 | Boothman et al. |
| 5,776,458 A | 7/1998 | Angelucci et al. |
| 5,780,514 A | 7/1998 | Gutteridge et al. |
| 5,783,598 A | 7/1998 | Boyd et al. |
| 5,824,700 A | 10/1998 | Frydman et al. |
| 5,849,259 A | 12/1998 | Hilger et al. |
| 5,866,679 A | 2/1999 | DeFeo-Jones et al. |
| 5,869,522 A | 2/1999 | Boyd et al. |
| 5,877,165 A | 3/1999 | Miura et al. |
| 5,880,161 A | 3/1999 | Basu et al. |
| 5,883,270 A | 3/1999 | Frydman et al. |
| 5,886,173 A | 3/1999 | Hemmi et al. |
| 5,889,061 A | 3/1999 | Frydman et al. |
| 5,912,241 A | 6/1999 | Gottlieb et al. |
| 5,962,533 A | 10/1999 | Bergeron, Jr. |
| 5,969,163 A | 10/1999 | Frydman et al. |
| 5,977,187 A | 11/1999 | Frydman et al. |
| 5,985,331 A | 11/1999 | Gottlieb et al. |
| 5,998,362 A | 12/1999 | Feng et al. |
| 6,001,573 A | 12/1999 | Roelant |
| 6,025,351 A | 2/2000 | Morgan et al. |
| 6,066,628 A | 5/2000 | Stojiljkovic et al. |
| 6,083,479 A | 7/2000 | Platzek et al. |
| 6,100,430 A | 8/2000 | Yamamoto et al. |
| 6,130,204 A | 10/2000 | DeFeo-Jones et al. |
| 6,143,864 A | 11/2000 | DeFeo-Jones et al. |
| 6,174,858 B1 | 1/2001 | Brady et al. |
| 6,177,561 B1 | 1/2001 | Sinn et al. |
| 6,265,540 B1 | 7/2001 | Isaacs et al. |
| 6,482,943 B1 | 11/2002 | Blokhin et al. |
| 6,809,176 B2 | 10/2004 | Blokhin et al. |
| 2002/0004031 A1 | 1/2002 | Dinkelborg et al. |
| 2002/0183512 A1 | 12/2002 | Blokhin et al. |
| 2003/0013677 A1 | 1/2003 | Blokhin et al. |

FOREIGN PATENT DOCUMENTS

| | | |
|---|---|---|
| WO | WO-96/22962 A1 | 8/1996 |
| WO | WO 96/33988 A1 | 10/1996 |
| WO | WO-96/40096 A1 | 12/1996 |
| WO | WO-97/02027 A1 | 1/1997 |
| WO | WO 97/02030 A1 | 1/1997 |
| WO | WO 97/08162 A1 | 3/1997 |
| WO | WO-97/29199 A2 | 8/1997 |
| WO | WO 97/30022 A1 | 8/1997 |
| WO | WO 97/31611 A2 | 9/1997 |
| WO | WO 97/31936 A2 | 9/1997 |
| WO | WO 97/31936 A3 | 9/1997 |
| WO | WO-98/17624 A1 | 4/1998 |
| WO | WO 98/25884 A1 | 6/1998 |
| WO | WO 98/25885 A1 | 6/1998 |
| WO | WO-98/32729 A1 | 7/1998 |
| WO | WO-98/33503 A1 | 8/1998 |
| WO | WO-98/37057 A1 | 8/1998 |
| WO | WO-98/52966 A1 | 11/1998 |
| WO | WO-99/13920 A2 | 3/1999 |
| WO | WO-99/16474 A1 | 4/1999 |
| WO | WO-99/16757 A1 | 4/1999 |
| WO | WO-99-62512 A1 | 12/1999 |
| WO | WO-00/01419 A1 | 1/2000 |
| WO | WO-00/05235 A1 | 2/2000 |
| WO | WO-00/17205 A2 | 3/2000 |
| WO | WO-00/18439 A2 | 4/2000 |
| WO | WO-00/66175 A2 | 11/2000 |
| WO | WO-00/66175 A3 | 11/2000 |
| WO | WO 00/66528 A2 | 11/2000 |
| WO | WO 00/66528 A3 | 11/2000 |
| WO | WO-00/66587 A2 | 11/2000 |

OTHER PUBLICATIONS

European Search Report mailed on Sep. 14, 2005 for European Patent Application No. 05011989.0 filed on Apr. 27, 2000, 4 pages.

Guay, V. et al. (Jan.-Feb. 1986), "Synthesis of (±)-7- and 8-Hydroxydunnione," *Journal of Natural Products* 49(1):122-125.

Inoue, K. et al. (Jun. 1, 1982). "Structures of Unusually Prenylated Naphthoquinones of *Streptocarpus dunnii* and its Cell Cultures," *Chemical and Pharmaceutical Bulletin* 30(6):2265-2268.

Akgun, N. et al. (1996). "Phototoxicity, Darktoxicity and Uptake Kinetics of Natural Hydrophilic and Hydrophobic Phorphyrins in Endothelial Cells," *Proc. SPIE-Int. Soc. Opt. Eng.* 2625:488-498.

Alfonso, I. et al. (1996). "Sequential Biocatalytic Resolution of (+)-trans-cyclohexane-1,2-diamine. Chemoenzymic Synthesis of an Optically Active Polyamine," *Chem. Commun.* 21:2471-2472.

Allolio, B. et al. (1989). "Treatment of Metastasizing Adrenal Carcinoma with Suramin," *Dtsch. Med. Wuschenschr* 114(10):381-384. (In German; first page of document has English abstract).

Bachrach, U. et al. (1971). "Inactivation of Myxoviruses by Oxidized Polyamines," *J. Gen. Virol.* 11:1-9.

Bachrach, U. et al. (Feb. 1972). "Effect of Oxidized Spermine and Other Aldehydes on the Infectivity of Vaccinia Virus," *Appl. Microbiol.* 23(2):232-235.

Bachrach, U. et al. (1971). "Antivirus Action of Acrolein, Glutaraldehyde and Oxidized Spermine," *J. Gen. Virol.* 13:415-422.

Basu, H.S. et al. (1990). "Effects of Variation in the Structure of Spermine on the Association with DNA and the Induction of DNA Conformational Changes," *Biochem. J.* 269:329-334.

Behe, M. et al. (Mar. 1981). "Effects of Methylation on a Synthetic Polynucleotide: the B-Z Transition in Poly(dG-m$^5$ dC)-Poly(dG-m$^5$ dC)," *Proc. Natl. Acad. Sci. USA* 78(3):1619-1623.

Berchtold, C.M. et al. (1998), "Inhibition of Cell Growth in CaCO2 Cells by the Polyamine Analogue N.sup.1, N.sup.12-bis(ethyl)Spermine is Preceded by a Reduction in MYC Oncoprotein Levels," *J. Cell. Physiol.* 174:380-386.

Bernacki, R.J. et al. (May 1, 1992). "Antitumor Activity of N,N'-Bis(Ethyl)Spermine Homologues Against Human MALME-3 Melanoma Xenografts," *Cancer Res.* 52:2424-2430.

Bloomfield, V.A. et al. (1981). *Interactions of Polyamines with Polynucleotides*, Dekker, New York, pp. 183-206.

Bressoud, D. et al. (1992). "Dark Induction of Haem Oxygenase Messenger RNA by Haematoporphyrin Derivative and Zinc Phthalocyanine; Agents for Photodynamic Therapy," *J. Photochem. Photobiol. B: Biol.* 14:311-318.

Broder, S. et al. (Sep. 21, 1985). "Effects of Suramin on HTLV-III/LAV Infection Presenting as Kaposi's Sarcoma or AIDS-Related Complex: Clinical Pharmacology and Suppression of Virus Replication In Vivo," *Lancet* 2:627-630.

Byers, T.L. et al. (1990). "Regulation of Polyamine Transport in Chinese Hamster Ovary Cells," *J. Cellular Physiol.* 143:460-467.

Chang, B.K. et al. (1992). "Antitumor Effects of N-Alkylated Polyamine Analogues in Human Pancreatic Adenocarcinoma Models," *Cancer Chemother. Pharmacol.* 30:179-182.

Chang, B.K. et al. (1992). "Regulatory and Antiproliferative Effects of N-Alkylated Polyamine Analogues in Human and Hamster Pancreatic Adenocarcinoma Cell Lines," *Cancer Chemother. Pharmacol.* 30:183-188.

Chang, B.K. et al. (Oct. 1993). "Effects of Diethyl Spermine Analogues in Human Bladder Cancer Cell Lines in Culture," *J. Urol.* 150:1293-1297.

Christensson, A. et al. (1990). "Enzymatic Activity of Prostate-Specific Antigen and its Reactions with Extracellular Serine Proteinase Inhibitors," *Eur. J. Biochem.* 194:755-763.

Creaven, P.J. et al. (1997). "Unusual Central Nervous System Toxicity in a Phase I Study of N.sup.1 N.sup.11 Diethylnorspermine in Patients with Advanced Malignancy," *Invest. New Drugs* 15:227-234.

Davidson, N.E. et al. (May 1, 1993). "Growth Inhibition of Hormone-Responsive and -Resistant Human Breast Cancer Cells in Culture by N.sup.1, N.sup.12 -Bis(Ethyl)Spermine," *Cancer Res.* 53:2071-2075.

DeFeo-Jones, D. et al. (Nov. 2000). "A Peptide-Doxorubicin 'Prodrug' Activated by Prostate-Specific Antigen Selectively Kills Prostate Tumor Cells Positive for Prostate-Specific Antigen In Vivo," *Nat. Med.* 6(11):1248-1252.

Denmeade, S.R. et al. (Mar. 2000). "Enzymatic Activation of a Thapsigargin Prodrug by Prostate Specific Antigen (PSA) as Treatment for Metastatic Prostate Cancer," *Proceedings of the American Association for Cancer Research 91st Annual Meeting*, Apr. 1-5, 2000, San Francisco, CA 41:46 Abstract #292.

Denmeade, S.R. et al. (May 1998). "Enzymatic Activation of Prodrugs by Prostate-Specific Antigen: Targeted Therapy for Metastatic Prostate Cancer," *Cancer Journal From Scientific American* 4(Suppl.1):S15-S21.

Driscoll et al. (Apr. 1974). "Structure Antitumor Activity Relationships Among Quinone Derivatives," *Cancer Chemot. Reports* 4(2):1-362.

Dubowchik, G.M. et al. (1998). "Cathepsin B-Sensitive Dipeptide Prodrugs. I. A Model Study of Structural Requirements for Efficient Release of Doxorubicin," *Bioorg. Med. Chem. Lett.* 8:3341-3346.

Dunzendorfer, U. (1985). "Polyamines, Polyamine Antimetabolites and Urogenital Tumors. State of Research and Clinical Results," *Urol. Int.* 40:241-250. (In German, first page of document has English abstract.).

Fernandez, C.O. et al. (1994). "Interactions Between Polyamine Analogs with Antiproliferative Effects and tRNA: a $^{15}$N NMR Analysis," *Cell Mol. Biol.* 40(7):933-944.

Feuerstein, B.G. et al. (1991). "Implications and Concepts of Polyamine-Nucleic Acid Interactions," *J. Cell. Biochem.* 46:37-47.

Fiedler, W.J. et al. (1993). "Synthese Von Selektiv N-funktionalisierten Polyamin-Derivaten," *Helv. Chim. Acta* 76:1511-1519. (In German—first page of document has English abstract.).

Fischer, H.A. (1975). "Synthesis of $^3$H-Spermine," *J. Labeled Compd.* 11(1):141-143, (In German—Chemical Abstracts "CAPlus" record attached.).

Freitas, I. et al. (1987), "Dark Effects of Hematoporphyrin Derivative on Lactate Dehydrogenase Activity and Distribution in HeLa Cells: Cytochemical Evaluation," *Photochemistry and Photobiology* 46(5):699-706.

Freitas, I. et al. (1988). "Dark Effects of Porphyrins on the Activity and Subcellular Distribution of Dehydrogenases in Yoshida Hepatoma Cells: Cytochemical Evaluations," *Medicine Biologie Environment* 16:97-109.

Frydman, B. et al. (1999). "Polyamine-Based Chemotherapy of Cancer," *Exp. Opin. Ther. Patents* 9(8):1055-1068.

Frydman, B. et al. "Novel Polyamine Analog Conjugates And Quinone Conjugates As Therapies For Cancers And Prostate Diseases," U.S. Appl. No. 09/561,172, filed Apr. 27, 2000.

Frydman, L. et al. (Oct. 1992). "Interactions Between Natural Polyamines and tRNA: an $^{15}$N NMR Analysis," *Proc. Natl. Acad. Sci. USA* 89:9186-9190.

Gosule, L.C. et al. (1978). "DNA Condensation with Polyamines I. Spectroscopic Studies," *J. Mol. Biol.* 121:311-326.

Goto, M. et al. (Feb. 1969). "Stereochemical Studies of Metal Chelates. III. Preparation and Stereochemistry of Cobalt (III) Complexes with C-Substituted Triethylenetetramines at the Central Ethylenediamine Bridge," *Inorg. Chem.* 8(2):358-366.

Hafner, E.W. et al. (Dec. 25, 1979). "Mutants of *Escherichia coli* that do not Contain 1,4-Diaminobutane (Putrescine) or Spermidine," *J. Biol. Chem.* 254(24):12419-12426.

Herr, H.W. et al. (Mar. 15, 1984). "Potentiation of Methylglyoxal-Bis-Guanylhydrazone by Alpha-Difluoromethylornithine in Rat Prostate Cancer," *Cancer* 53(6):12494-1298.

Hondo, H. (1988). "Anti-Tumor Effect on Hyperthermia Plus Hematoporphyrin Derivative on Malignant Brain Tumor," *Brain and Nerve* 40(5):477-484. (Biosis English language abstract only).

Horn, Y. et al. (1987). "Phase I-II Clinical Trial with Alpha-Difluoromethylornithine—an Inhibitor of Polyamine Biosynthesis," *Eur. J. Cancer Clin. Oncol.* 23(8):1103-1107.

Horoszewicz, J.S. et al. (Apr. 1983). "LNCaP Model of Human Prostatic Carcinoma," *Cancer Res.* 43:1809-1818.

Igarashi, K. et al. (Oct. 30, 1990). "Spermine-Like Functions of N.sup.1, N.sup.12 -Bis(Ethyl)Spermine: Stimulation of Protein Synthesis and Cell Growth and Inhibition of Gastric Ulceration," *Biochem. Biophys. Res. Commun.* 172(2):715-720.

Iwata, M. et al. (1989). "Efficient Synthetic Method for Differentially Protected Naturally Occurring Acyclic Polyamines," *Bull. Chem. Soc. Japan* 62(4):1102-1106.

Jain, S. et al. (1989). "Base Only Binding of Spermine in the Deep Groove of the A-DNA Octamer d(GTGTACAC)," *Biochem.* 28(6):2360-2364.

James, D. A. et al. (1994). "Potency and Selective Toxicity of Tetra(Hydroxyphenyl)-and Tetrakis(dihydroxyphenyl)porphyrins in Human Melanoma Cells, With and Without Exposure to Red Light," *Photochemistry and Photobiology* 59(4):441-447.

Janne J. et al. (1978). "Polyamines in Rapid Growth and Cancer," *Biochim.Biophys. Acta.* 473:241-293.

Jeffers, L. et al. (1997). "Effects of the Polyamine Analogues BE-4-4-4-4, BE-3-7-3, and BE-3-3-3 on the Proliferation of Three Prostate Cancer Cell Lines," *Cancer Chem. Pharm.* 40:172-179.

Kanter, P.M. et al. (1994). "Preclinical Toxicologic Evaluation of DENSPM (N$^1$, N$^{11}$—diethylnorspermine) in Rats and Dogs," *Anticancer Drugs* 5:448-456.

Khanum, F. et al. (1989). "Effects of Hematoporphyrin Derivative on the Cellular Energy Metabolism in the Absence and Presence of Light," *Photochem. and Photobiol.* 50(5):647-648, 650-651.

Kobiro, K. et al. (1992). "Synthesis and Molecular Structures of Nickel (II) Alkyl-Substituted Cyclam Complexes," *Inorg. Chem.* 31(4):676-685.

Koningsberger, J. C. (1992). "Toxic Dark Effects of Protoporphyrin," *Digestive Disease Week and The 93rd Annual Meeting of the American Gastroenterological Association San Francisco, California Supplement to Gastroenterology* 102(4):A835. (Abstract only).

Koningsberger, J. C. et al. (1995). "Exogenous Protoporphyrin Inhibits Hep G2 Cell Proliferation, Increases the Intracellular Hydrogen Peroxide Concentration and Causes Ultrastructural Alterations," *J. Hepatology* 22:57-65.

Kramer, D. et al. (Feb. 3, 1995). "Stable Amplification of the S-Adenosylmethionine Decarboxylase Gene in Chinese Hamster Ovary Cells," *J. Biol. Chem.* 270(5):2124-2132.

Kramer, D.L. et al. (1993). "Regulation of Polyamine Transport by Polyamines and Polyamine Analogs," *J. Cell. Physiol.* 155:399-407.

Kramer, D.L. et al. (Dec. 15, 1997). "Effects of Novel Spermine Analogs on Cell Cycle Progression and Apoptosis in MALME-3M Human Melanoma Cells," *Cancer Res.* 57:5521-5527.

Lilja, H. et al. (Nov. 1985) "A Kallikrein-like Serine Protease in Prostatic Fluid Cleaves the Predimonant Seminal Vesicle Protein," *J. Clin. Invest.* 76(5):1899-1903.

Lovaas, E. (1997). "Antioxidative and Metal-Chelating Effects of Polyamines," *Adv. Pharmacol.* 38:119-149.

Mamont, P.S. et al. (Mar. 15, 1978). "Anti-Proliferative Properties of DL-Alpha-Difluoromethyl Ornithine in Cultured Cells. A Consequence of the Irreversible Inhibition of Ornithine Decarboxylase," *Biochem. Biophys. Res. Commun.* 81(1):58-66.

Marton, L.J. et al. (1995). "Polyamines as Targets for Therapeutic Intervention," *Ann. Rev. Pharm. Toxicol.* 35:55-91.

Mazzoni, A. et al. (1986). "Comparative Distribution of Free Doxorubicin and Poly-L-aspartic Acid Linked Doxorubicin in MS-2 Sarcoma Bearing Mice," *Cancer Drug Deliv.* 3(3):163-172.

Mi, Z. et al. (1998). "Human Prostatic Carcinoma Cell Lines Display Altered Regulation of Polyamine Transport in Response to Polyamine Analogs and Inhibitors," *Prostate* 34:51-60.

Morgan, D.M.L. (1998). "Polyamines. An Introduction," *Methods. Mol. Biol.* 70:3-30.

Morgan, D.M.L. et al. (1983). "Polyamine Oxidation and the Killing of Intracellular Parasites," *Adv. Polyamine Res.* 4:169-174.

Morgan, D.M.L. et al. (1986). "The Effect of Purified Aminoaldehydes Produced by Polyamine. Oxidation on the Development in Vitro of Plasmodium Falciparum in Normal and Glucose-6-Phosphate-Dehydrogenase-Deficient Erythrocytes," *Biochem. J.* 236:97-101.

Mukhopadhyay, R. et al. (1995). "Effect of Bis(benzyl)Polamine Analogs on Leishmania Donovani Promastigotes," *Exp. Parasitol.* 81:39-46.

Nagarajan, S. et al. (1987). "Chemistry of Naturally Occurring Polyamines. II. Unsaturated Spermidine and Spermine Derivatives," *J. Org. Chem.* 52(22):5044-5046.

Nishimura, K. et al. (1971). "Phagocidal Effects of Acrolein," *Biochim. Biophys. Acta* 247:153-156.

Novarina, A. et al. (1988). "Quantative Histochemistry of Lactate Dehydrogenase in Tumor Cells. Dark Effects of Porphyrin Drugs," *Proceedings of the Eight International Congress of Histochemistry and Cytochemistry and the Thirty-ninth Annyal Meeting of the Histochemical Society J. Histochemistry and Cytochemistry* 36(7a):941. Abstract 404.

O'Sullivan, M.C. et al. (1997). "Polyamine Derivatives as Inhibitors of Trypanothione Reductase and Assessment of Their Trypanocidal Activities," *Bioorg. Med. Chem.* 5(12):2145-2155.

Pegg, A.E. et al. (1982). "Polyamine Metabolism and Function," *Am. J. Physiol.* 243 (Cell Physiol. 12):C212-C221.

Porter, C.W. et al. (1988). "Enzyme Regulation as an Approach to Interference with Polyamine Biosynthesis—An Alternative to Enzyme Inhibition," *Advances in Enzyme Regulation* 27:57-79.

Porter, C.W. et al. (1988). "Regulation of Polyamine Biosynthetic Activity by Spermidine and Spermine Analogs—A Novel Antiproliferative Strategy," *Adv. Exp. Med. Biol.* 250:677-690.

Porter, C.W. et al. (Jul. 15, 1991). "Correlations Between Polyamine Analogue-Induced Increases in Spermidine/Spermine $N^1$-Acetyltransferase Activity, Polyamine Pool Depletion, and Growth Inhibition in Human Melanoma Cell Lines," *Cancer Res.* 51:3715-3720.

Porter, C.W. et al. (Jun. 1, 1987). "Relative Abilities of Bis(Ethyl) Derivatives of Putrescine, Spermidine, and Spermine to Regulate Polyamine Biosynthesis and Inhibit L1210 Leukemia Cell Growth," *Cancer Res.* 47:2821-2825.

Rainwater, L.M. et al. (Aug. 1990). "Prostate-Specific Antigen Testing in Untreated and Treated Prostatic Adenocarcinoma," *Mayo Clinic Proc.* 65:1118-1126.

Redd, M.J. et al. (Apr. 25, 1997). "A Complex Composed of Tup1 and Ssn6 Represses Transcription in Vitro," *J. Biol. Chem.* 272(17):11193-11197.

Reddy, V.K. et al. (1998). "Conformationally Restricted Analogues of $^1N$, $^{12}N$-bisethylspermine:Synthesis and Growth Inhibitory Effects on Human Tumor Cell Lines," *J. Med. Chem.* 41(24):4723-4732.

Redgate, E.S. et al. (1995). "Polyamines in Brain Tumor Therapy," *J. Neuro-Oncol.* 25:167-179.

Rihova, B. et al. (1993). "Targetable Photoactivatable Drugs. 3. In Vitro Efficacy of Polymer Bound Chlorin $E_{.sub.6}$ Toward Human Hepatocarcinoma Cell Line (PLC/PRF/5) Targeted with Galactosamine and to Mouse Splenocytes Targeted with Anti-Thy 1.2 Antibodies," *J. Controlled Release* 25:71-87.

Shappell, N.W. et al. (1992). "Differential Effects of the Spermine Analog, $N^1$, $N^{12}$-Bis(Ethyl)-Spermine, on Polyamine Metabolism and Cell Growth in Human Melanoma Cell Lines and Melanocytes," *Anticancer Res.* 12:1083-1089.

Sharma, A. et al. (Aug. 1997). "Antitumor Efficacy of $N^1,N^{11}$-Diethylnorspermine on a Human Bladder Tumor Xenograft in Nude Athymic Mice," *Clin. Cancer Res.* 3:1239-1244.

Sicuro, T. et al. (1987). "Dark-and Light-Interaction of Porphyrins with Malignant Cell Compartment," *Medicine Biologie Environnement* 15:67-70.

Sinha, A.A. et al. (1995). "Cathepsin B in Angiogenesis of Human Prostate: An Immunohistochemical and Immunoelectron Microscopic Analysis," *Anat. Rec.* 241:353-362.

Sinha, A.A. et al. (1995). "Immunohistochemical Localization of Cathepsin B in Neoplastic Human Prostate," *Prostate* 26:171-178.

Snyder, R.D. et al. (1994). "Anti-Mitochondrial Effects of Bisethyl Polyamines in Mammalian Cells," *Anticancer Res.* 14:347-356.

Snyder, R.D. et al. (May 15, 1991). "Effects of Polyamine Analogs on the Extent and Fidelity of In Vitro Polypeptide Synthesis," *Biochem. Biophys. Res. Commun.* 176(3):1383-1392.

Splinter, T.A.W. et al. (1986). "Phase I Study of Alpha-difluoromethylornithine and Methyl-GAG," *Eur. J. Cancer Clin. Oncol.* 22(1):61-67.

Takenaka, S. et al. (1996). "Construction of a Dimeric DNA-Binding Peptide Model by Peptide-Anthraquinone Conjugation," *Int. J. Pept. Prot. Res.* 48(5):397-400.

Vonarx-Coinsman, V. et al. (1995). "HepG2 Human Hepatocarcinoma Cells: an Experimental Model for Photosensitization by Endogenous Porphyrins," *J. Photochem. and Photobiol. B: Biology* 30:201-208.

Watt, K.W.K. et al. (May 1986). "Human Prostate-Specific Antigen: Structural and Functional Similarity with Serine Proteases," *Proc. Natl. Acad. Sci. USA* 83:3166-3170.

Woodburn, K. W. (1992). "Evaluation of Porphyrin Characteristics Required for Photodynamic Therapy," *Photochemistry and Photobiology* 55(5):697-701, 703-704.

Wunz, T.P. et al. (1987), "New Antitumor Agents Containing the Anthracene Nucleus," *J. Med. Chem.* 30(8):1313-1321.

Yan, S. et al. (Feb. 1998). "Cathepsin B and Human Tumor Progression," *Biol. Chem.* 379:113-123.

Yuan, Z.M. et al. (1994). "Cytotoxic Activity of $N^1$- and $N^8$-Aziridinyl Analogs of Spermidine," *Biochem. Pharmacol.* 47(9):1587-1592.

Zagaja, G.P. et al. (1998). "Effects of Polyamine Analogues on Prostatic Adenocarcinoma Cells in Vitro and In Vivo," *Cancer Chemother. Pharmacol.* 41(6):505-512.

Ashraf, W. et al. (1994). "Comparative Effects of Intraduodenal Psyllium and Senna on Canine Small Bowel Motility," *Aliment. Pharmacol. Ther.* 8:329-336.

Baez, S. et al. (May 15, 1997). "Glutathione Transferases Catalyse the Detoxication of Oxidized Metabolites (O-Quinones) of Catecholamines and May Serve as an Antioxidant System Preventing Degenerative Cellular Processes," *Biochem. J.* 324:25-28.

Bailey, S.M. et al. (1997). "Involvement of DT-Diaphorase (EC 1.6.99.2) in the DNA Cross-Linking and Sequence Selectivity of the Bioreductive Anti-Tumour Agent EO9," *Br. J. Cancer* 76(12):1596-1603.

Begleiter, A. et al. (1997). "Induction of DT-Diaphorase in Cancer Chemoprevention and Chemotherapy," *Oncol. Res.* 9:371-382.

Boveris, A. et al. (1978). "Superoxide Anion Production and Trypanocidal Action of Naphthoquinones on Trypanosoma Cruzi," *Comp. Biochem. Physiol.* 61C:327-329.

Bullock, F.J. et al. (Jan. 1970). "Antiprotozoal Quinones. II. Synthesis of 4-amino-1,2-naphthoquinones and Related Compounds as Potential Antimalarials," *J. Med. Chem.* 13(1):97-103.

Chung, J. et al. (Nov. 8, 1996). "Acceleration of the Alcohol Oxidation Rate in Rats with Aloin, a Quinone Derivative of Aloe," *Biochem. Pharmacol.* 52:1461-1468.

Clarys, P. and Barel, A. (1998). "Efficacy of Topical Treatment of Pigmentation Skin Disorders with Plant Hydroquinone Glucosides as Assessed by Quantitative Color Analysis," *J. Dermatol.* 25:412-414.

Cortelli, P. et al. (1997). "Clinical and Brain Bioenergetics Improvement With Idebenone in a Patient with Leber's Hereditary Optic Neuropathy: a Clinical and 31P-MRS Study," *J. Neurol. Sci.* 148:25-31.

Cote, P. and Goodman, L. (1973). "Glucopyranosides Derived from 2-hydroxy-1,4-naphthoquinones," *Carbohyd. Res.* 26:247-251.

De Groot, F.M.H. et al. (1999). "Synthesis and Biological Evaluation of Novel Prodrugs of. Anthracyclines for Selective Activation by the Tumor-Associated Protease Plasmin," *J. Med. Chem.* 42(25):5277-5283.

Dekant, W. (1993). "Bioactivation of Nephrotoxins and Renal Carcinogens by Glutathione S-Conjugate Formation," *Toxicol. Lett.* 67:151-160.

Denmeade, S.R. et al. (Nov. 1997). "Specific and Efficient Peptide Substrates for Assaying the Proteolytic Activity of Prostate-Specific Antigen," *Cancer Res.* 57:4924-4930.

Dolan, M.E. et al. (1998). "Effects of 1,2-naphthoquinones on Human Tumor Cell Growth and Lack of Cross-Resistance with Other Anticancer Agents," *Anticancer Drugs* 9:437-448.

Dunn, W.J. III et al. (1980). "Structure-Activity Analyzed by Pattern Recognition: the Asymmetric Case," *J. Med. Chem.* 23(6):595-599.

Eyer, P. (Oct. 1994). "Reactions of Oxidatively Activated Arylamines with Thiols: Reaction Mechanisms and Biologic Implications. An Overview," *Environ. Health Persp.* 102(Suppl. 6):123-132.

Fowler, L.M. et al. (1991). "Nephrotoxicity of 4-Aminophenol Glutathione Conjugate," *Hum. Exp. Toxicol.* 10:451-459.

Frydman, B. et al. (Feb. 15, 1997). "Induction of DNA Topoisomerase II-Mediated DNA Cleavage by Beta-Lapachone and Related Naphthoquinones," *Cancer Res.* 57:620-627.

Gantchev, T.G. and Hunting, D.J. (1997). "Inhibition of the Topoisomerase II-DNA Cleavable Complex by the Ortho-Quinone Derivative of the Antitumor Drug Etoposide (VP-16)," *Biochem. Biophys. Res. Comm.* 237(1):24-27.

Hinson, J.A. and Forkert, P. (1995). "Phase II Enzymes and Bioactivation," *Can. J. Physiol. Pharm.* 73:1407-1413.

Inouye, H. et al. (Feb. 1975). "Quinones and Related Compounds in Higher Plants. II. On the Naphthoquinones and Related Compounds from Catalpa Wood," *Chem. Pharm. Bull.* 23(2):384-391.

Jeong, J.K. et al. (Sep. 1996). "Quinone Thioether-Mediated DNA Damage, Growth Arrest, and Gadd153 Expression in Renal Proximal Tubular Epithelial Cells," *Mol. Pharmacol.* 50(3):592-598.

Li, C.J. et al. (Sep. 1, 1995). "Induction of Apoptosis by Beta-Lapachone in Human Prostate Cancer Cells." *Cancer Res.* 55:3712-3715.

Mahadik, S.P. and Scheffer, R.E. (1996). "Oxidative Injury and Potential Use of Antioxidants in Schizophrenia," *Prostaglandins Leukot. Essent. Fatty Acids* 55(1&2):45-54.

Mertens, J.J.W.M. et al. (1991). "Inhibition a Gamma-Glutamyl Transpeptidase Potentiates the Nephrotoxicity of Glutathione-Conjugated Chlorohydroquinones," *Toxicol. Appl. Pharmacol.* 110:45-60.

Monks, T.J. (1995). "Modulation of Quinol/Quinone-Thioether Toxicity by Intramolecular Detoxication," *Drug Metab. Rev.* 27(1&2):93-106.

Monks, T.J. et al. (1994). "Oxidation and Acetylation as Determinants of 2-Bromocystein-S-ylhydroquinone-Mediated Nephrotoxicity," *Chem. Res. Toxicol.* 7(4):495-502.

Mordente, A. et al. (1998). "Antioxidant Properties of 2,3-Dimethoxy-5-Methyl-6-(10-Hydroxydecyl)-1,4-Benzoquinone (Idebenone)," *Chem. Res. Toxicol.* 11(1):54-63.

Müller-Lissner, S.A. (1993). "Adverse Effects of Laxatives: Fact and Fiction," *Pharmacol.* 47(Suppl. 1):138-145.

Nanji, A.A. and Tahan, S.R. (1996). "Association Between Endothelial Cell Proliferation and Pathologic Changes in Experimental Alcoholic Liver Disease," *Toxicol. Appl. Pharmacol.* 140:101-107.

Neder, K. et al. (1998). "Reaction of β-lapachone and Related Maphthoquinones with 2-Mercaptoethanol: A Biomimetic Modes of Topoisomerase II Poisoning by Quinones," *Cell. and Mol. Biol.* 44(3):465-474.

Nelson, W.L. et al. (1984). "The 3,4-Catechol Derivative of Propranolol, a Minor Dihydroxylated Metabolite," *J. Med. Chem.* 27(7):857-861.

O'Brien, P.J. (1991). "Molecular Mechanisms of Quinone Cytotoxicity," *Chem. Biol. Interactions* 80:1-41.

Pershin, G.N. et al. (1975). "Bonaphthon, a New Antiviral Chemotherapeutic Agent," Retrieved from STN Database Accession No. 82:118989 *In Farmakol. Toksikol* (1975) 38(1):69-73.

Planchon, S.M. et al. (Sep. 1, 1995). "β-Lapachone-Mediated Apoptosis in Human Promyelocytic Leukemia (HL-60) and Human Prostate Cancer Cells: A p53-Independent Response," *Cancer Res.* 55:3706-3711.

Planchon, S.M. et al. (1999). "Bcl-2 Protects Against Beta-Lapachone-Mediated Caspase 3 Activation and Apoptosis in Human Myeloid Leukemia (HL-60) Cells," *Oncol. Rep.* 6:485-492.

Puckett-Vaughn, D.L. et al. (1993). "Enzymatic Formation and Electrochemical Characterization of Multiply Substituted Glutathione Conjugates of Hydroquinone," *Life Sci.* 52(14):1239-1247.

Rao, D.N.R. et al. (1997). "A Comparative Study of the Redox-Cycling of a Quinone (Rifamycin S) and a Quinonimine (Rifabutin) Antibiotic by Rat Liver Microsomes," *Free Radic. Biol. Med.* 22(3):439-446.

Saito, T. (Mar. 1988). "An Anticancer Drug—Carboquone," *Jpn. J. Cancer Chemother.* 15(3):549-554. (English abstract included).

Singh, S. et al. (Nov. 15, 1996). "Capsaicin (8-Methyl-N-Vanillyl-6-Nonenamide) is a Potent Inhibitor of Nuclear Transcription Factor-Kappa B Activation by Diverse Agents," *J. Immunol.* 157(10):4412-4420.

Sun, J.S. et al. (1998). "A Preparative Synthesis of Lapachol and Related NaphthoQuinones," *Tetrahedron Letters* 39:8221-8224.

Takuwa, A. et al. (Sep. 1986). "The Addition of Alcohol to 1,2-naphthoquinone Promoted by Metal Ions. Facile Synthesis of 4-alkoxy-1,2-naphthoquinones," *Bull. Chem. Soc. Jpn.* 59(9):2959-2961.

Takuwa, A. et al. (1986). "Structural Influences on the Isomerization of 4-benzyl- and 4-allyl-1,2-Naphthoquinones to Quinone Methodes and their Stereochemistry," *J. Chem. Soc. Perkin Trans.* 1:1627-1631.

Matsumoto, T. et al., "α-Caryopteron, ein neues Pyrano-juglon aus *Caryopteris clandonesis*", Helvetica Chimica Acta, vol. 52, Fasc. 3, 1969, No. 91, pp. 808-812 (includes English-language Chemical Abstract).

Planchon, S.M. et al. (1999). "Bcl-2 Protects Against β-Lapachone-Mediated Caspase 3 Activation and Apoptosis in Human Myeloid Leukemia (HL-60) Cells," *Oncol. Rep.* 6(3):485-492, Corresponding Caplus and Registry Records, 18 pages.

WO 97/31611: Corresponding Caplus and Registry Records, 18 pages.

Scheme 2
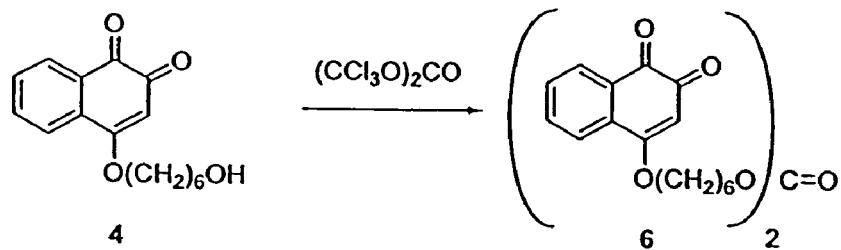
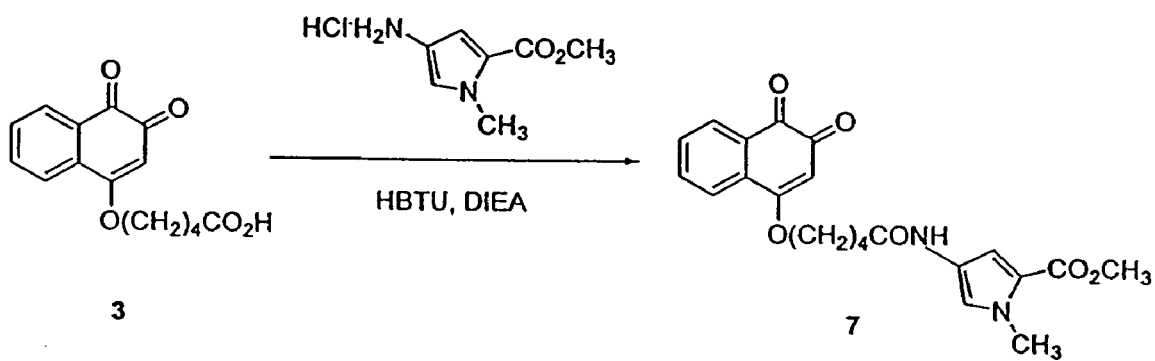
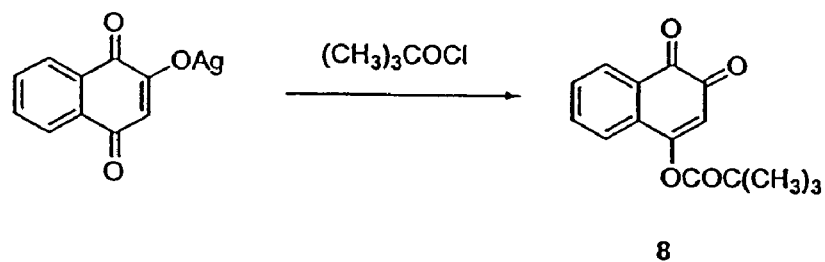
Figure 2

Scheme 3

Figure 4 Scheme 4

Figure 5  Scheme 5

Figure 6 Scheme 6

Figure 7　　Scheme 7

Scheme 8

Scheme 10

Scheme 11

R = (CH$_2$)$_4$CH$_3$

Scheme 12

Scheme 13

Boc-Gln + β-Ala-β-Lapachone → Boc-Gln-β-Ala-β-Lapachone →

Gln-β-Ala-β-Lapachone → Boc-Leu-Gln-β-Ala-β-Lapachone →

Leu-Gln-β-Ala-β-Lapachone → Nα-Boc-Lys(Nε-Cbz)-Leu-Gln-β-Ala-β-Lapachone

→ Lys(Nε-Cbz)-Leu-Gln-β-Ala-β-Lapachone → morpholino-Ser(OBn)-Lys(Nε-Cbz)-Leu-Gln-β-Ala-β-Lapachone → morpholino-Ser-Lys-Leu-Gln-β-Ala-β-Lapachone

N-Fmoc-Ser(OBn) → N-Fmoc-Ser(OBn)-OtBu → Ser(OBn)-OtBu →
morpholino-Ser(OBn)-OtBu → morpholino-Ser(OBn)

FIG. 13

Scheme 14

Boc-Leu + β-Lapachone → Boc-Leu-β-Lapachone → Leu-β-Lapachone →

Boc-Gln-Leu-β-Lapachone → Gln-Leu-β-Lapachone →

Boc-Leu-Gln-Leu-β-Lapachone → Leu-Gln-Leu-β-Lapachone →

Boc-Lys(Nε-Cbz)-Leu-Gln-Leu-β-Lapachone →

Lys(Nε-Cbz)-Leu-Gln-Leu-β-Lapachone → morpholino-Ser(OBn)-Lys(Nε-Cbz)-Leu-Gln-Leu-β-Lapachone → morpholino-Ser-Lys-Leu-Gln-Leu-β-Lapachone

FIG. 14

Scheme 16

Scheme 17

QUINONES AS DISEASE THERAPIES

CROSS-REFERENCE TO RELATED APPLICATIONS

This application is a divisional of U.S. Ser. No. 10/139,978 filed May 6, 2002 (now U.S. Pat. No. 6,809,176), which is a divisional of U.S. Ser. No. 09/562,980 filed Apr. 27, 2000 (now U.S. Pat. No. 6,482,943), which claims the benefit of U.S. Provisional Application Ser. No. 60/131,842, filed Apr. 30, 1999, the contents of which are hereby incorporated by reference into the present disclosure for all purposes as if fully put forth herein.

STATEMENT OF RIGHTS TO INVENTIONS MADE UNDER FEDERALLY SPONSORED RESEARCH

Not applicable.

TECHNICAL FIELD

This invention relates to novel quinones. The invention also relates to conjugates of quinones with various peptides. The invention also relates to various medicinal and industrial uses of these compounds, including the use of these compounds in treating diseases such as cancer.

BACKGROUND OF THE INVENTION

The quinones are a large and varied group of natural products found in all major groups of organisms. Quinones are a group of aromatic dioxo compounds derived from benzene or multiple-ring hydrocarbons such as naphthalene, anthracene, etc. They are classified as benzoquinones, naphthoquinones, anthraquinones, etc., on the basis of the ring system. The C=O groups are generally ortho or para, and form a conjugated system with at least two C=C double bonds; hence the compounds are colored, yellow, orange or red. Quinones with long isoprenoid side chains, such as plastoquinone, ubiquinone and phytoquinone are involved in the basic life processes of photosynthesis and respiration. Quinones are biosynthesized from acetate/malonate via shikimic acid. A few quinones are used as laxatives and worming agents, and others are used a pigments in cosmetics, histology and aquarrell paints. Quinones have a variety of medicinal and industrial uses.

Many efficient antineoplastic drugs are either quinones (anthracycline derivatives, mitoxantrone, actinomycin), quinonoid derivatives (quinolones, genistein, bactracyclin), or drugs such as etoposide that can easily be converted to quinones by in vivo oxidation. Gantchev et al. (1997) *Biochem. Biophys. Res. Comm.* 237:24-27. The literature on quinone-DNA interactions is replete with references to quinones having the potential to undergo redox cycling with the formation of highly reactive oxygen species that are thought to relate to their cytotoxicity. O'Brien (1991) *Chem. Biol. Interactions* 80:1-41. It has also been shown that many quinones are efficient modifiers of the enzymatic activity of topoisomerase II, an enzyme essential for cell division.

Quinones are now widely used as anti-cancer, anti-bacterial and anti-malarial drugs, as well as fungicides. The antitumor activities of the quinones were revealed more than two decades ago when the National Cancer Institute published a report in which fifteen-hundred synthetic and natural quinones were screened for their anticancer activities. Driscoll et al. (1974) *Cancer Chemot. Reports* 4:1-362. Anti-cancer quinones include β-Lapachone, a plant product, which inhibits DNA topoisomerase II and induces cell death with characteristics of apoptosis in human prostate and promyelocytic leukemia cancer cell lines. Human breast and ovary carcinoma showed sensitivity of the cytotoxic effect of β-lapachone without signs of apoptosis. Li et al. (1995) *Cancer Res.* 55:3712-5; and Planchon et al. (1995) *Cancer Res.* 55:3706-11. 1,2-Naphthoquinone (3,4-b)dihydrofuran inhibits neoplastic cell growth and proliferation of several cancers, such as prostate, breast, colon, brain and lung, including multi-drug resistant types. WO 97/31936. Furanonaphthoquinone derivatives and other naphthoquinones and naphth-[2,3-d]-imidazole-4,9-dione compounds are also useful in treating malignant tumors such as those affecting the blood, breast, central nervous system, cervix, colon, kidney, lung, prostate and skin. WO 97/30022 and JP Patent No. 9235280. Anthraquinone derivatives with telomerase inhibitory activity are also useful in treating leukemia, lung cancer, myeloma, lymphoma, prostate, colon, head and neck, melanoma, hepatocellular carcinoma, bladder, ovarian, breast and gastric cancers. WO 98/25884 and WO 98/25885. Ansamycin benzoquinones are useful in the treatment of primitive neuroectodermal tumors, prostate cancer, melanoma and metastatic Ewing's sarcoma. WO 94/08578.

Quinones also have a number of other medicinal uses. Terpenoid-type quinones are also useful as treatments for diabetes. U.S. Pat. No. 5,674,900. Additional quinones can be used to treat cirrhosis and other liver disorders. U.S. Pat. Nos. 5,210,239 and 5,385,942. Hydroquinone amines and quinone amines are also useful for treating a number of conditions, including spinal trauma and head injury. U.S. Pat. No. 5,120,843. Degenerative central nervous system diseases, as well as vascular diseases, are treatable with quinones such as Idebenone [2,3-dimethoxy-5-methyl-6-(10-hydroxydecyl)-1,4-benzoquinone] and Rifamycin S. Mordente et al. (1998) *Chem. Res. Toxicol.* 11:54-63; Rao et al. (1997) *Free Radic. Biol. Med.* 22:439-46; Cortelli et al. (1997) *J. Neurol. Sci.* 148:25-31; and Mahadik et al. (1996) *Prostaglandins Leukot. Essent. Fatty Acids* 55:45-54. A vitamin K analog, 6-cyclo-octylamino-5,8-quinoline quinone shows efficacy for treatment of leprosy and tuberculosis. U.S. Pat. No. 4,963,565. Hydroquinone is used to treat skin pigmentation disorders. Clarys et al. (1998) *J. Dermatol.* 25:412-4. Mitomycin C-related drug indoloquinone EO9 has demonstrated cell killing against HL-60 human leukemia cells, H661 human lung cancer cells, rat Walker tumor cells and human HT29 colon carcinoma cells. Begleiter et al. (1997) *Oncol. Res.* 9:371-82; and Bailey et al. (1997) *Br. J. Cancer* 76:1596-603. Quinones such as aloin, a C-glycoside derivative of anthraquinone, accelerate ethanol oxidation and may be useful in treating acute alcohol intoxication. Chung et al. (1996) *Biochem. Pharmacol.* 52:1461-8 and Nanji et al. (1996) *Toxicol. Appl. Pharmacol.* 140:101-7. Quinones capsaicin and resiniferatoxin blocked activation of nuclear transcription factor NF-κB, which is required for viral replication, immune regulation and induction of various inflammatory and growth-regulatory genes. Singh et al. (1996) *J. Immunol.* 157:4412-20. Antiretroviral and antiprotozoan naphthoquinones are described in U.S. Pat. Nos. 5,780,514 and 5,783,598. Anthraquinones are also useful as laxatives. Ashraf et al. (1994) *Aliment. Pharmacol. Ther.* 8:329-36; and Muller-Lissner (1993) *Pharmacol.* 47 (Suppl. 1): 138-45.

A subset of quinones designated lapachones has been shown to have activity against neoplastic cells, as described in U.S. Pat. Nos. 5,969,163, 5,824,700, and 5,763,625. Antiviral activity (in combination with xanthine) or reverse transcriptase inhibitory activity for β-lapachone is suggested in U.S. Pat. Nos. 5,641,773 and 4,898,870, while antifungal and trypanosidal activity of β-lapachone is suggested in U.S. Pat. Nos. 5,985,331 and 5,912,241.

Quinones can be administered alone or in conjunction with other agents, such as 1,2-dithiole-3-thione. Begleiter et al. (1997). Hydroxyquinone can be used in conjunction with glycol or glyceryl esters of retinoic acid to treat skin disorders. WO 9702030. Combinational chemotherapy of carboquone, a benzoquinine derivative, and cis-Platinum, diminishes the side effects of the former. Saito (1988) *Gan To Kagaku Ryoho* 15:549-54.

Quinones also have various additional uses. A few quinones are used as laxatives and worming agents, and others are used a pigments in cosmetics, histology and aquarrell paints. Quinones include 2,5-cyclohexadiene-1,4-dione, which is useful as an oxidizing agent; in photography (U.S. Pat. No. 5,080,998); in manufacturing dyes and hydroquinone; in tanning hides; in strengthening animal fibers; and as a reagent.

In rapidly dividing cells such as tumor cells, cytotoxicity due to quinone administration has been attributed to DNA modification. However the molecular basis for the initiation of quinone cytotoxicity in resting or non-dividing cells has been attributed to the alkylation of essential protein thiol or amine groups and/or the oxidation of essential protein thiols by activated oxygen species and/or GSSG, glutathione disulfide. Oxidative stress arises when the quinone is reduced by reductases to a semiquinone radical which reduces oxygen to superoxide radicals and reforms the quinone. This futile redox cycling and oxygen activation forms cytotoxic levels of hydrogen peroxide and GSSG is retained by the cell and causes cytotoxic mixed protein disulfide formation. O'Brien (1991) *Chem. Biol. Interact.* 80:1-41.

Conjugation of quinones and glutathione (GSH) are sometimes associated with the process of detoxification. Jeong et al. (1996) *Mol. Pharmacol.* 50:592-8. For example, certain o-quinones contribute to the neurodegenerative processes underlying Parkinson's disease and schizophrenia. Glutathione transferase (GST) M2-2, which conjugates glutathione and o-quinones, prevents these processes. Baez et al. (1997) *Biochem. J.* 324:25-8. However, in many cases, conjugation with GSH actually leads to quinone bioactivation and toxicity. For example, the nephrotoxicity of hydroquinone and bromobenzene is mediated via quinone-glutathione conjugates. Jeong et al. (1996) *Mol. Pharmacol.* 50:592-8. The formation of GSH conjugates is also involved in the bioactivation of vicinal dihalopropane 1,2-dibromo-3-chloropropane. Hinson et al. (1995) *Can. J. Physiol. Pharm.* 73:1407-13. Additional examples of GSH conjugation potentiating the toxicity of quinones are described in Fowler et al. (1991) *Hum. Exp. Toxicol.* 10:451-9; Mertens et al. (1991) *Toxicol. Appl. Pharmacol.* 110:45-60; Puckett-Vaughn et al. (1993) *Life Sci.* 52:1239-47; Dekant (1993) *Toxicol. Lett.* 67:151-160; Monks et al. (1994) *Chem. Res. Toxicol.* 7:495-502; Monks (1995) *Drug Metab. Rev.* 27:93-106; and Eyer (1994) *Environ. Health Persp.* 102 (Suppl. 6):123-32.

Because of the wide variety of biological processes in which quinones play a critical role, it would be advantageous to develop novel quinones for various uses, including disease treatment.

All references cited herein are hereby incorporated by reference in their entirety.

SUMMARY OF THE INVENTION

The invention provides novel quinone compounds and methods for use of the quinone compounds in treating diseases.

In one embodiment, the invention comprises compounds of the formula

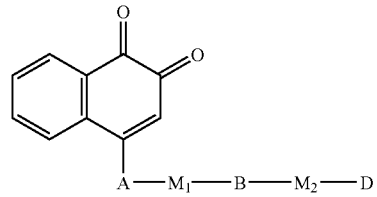

wherein A is selected from the group consisting of —O— and —CH$_2$—; wherein M$_1$ is selected from the group consisting of a single bond and C$_1$-C$_8$ alkyl, C$_1$-C$_8$ branched alkyl, C$_3$-C$_8$ cycloalkyl, and C$_3$-C$_8$ cycloaryl; wherein B is selected from the group consisting of —CH$_2$—, —O—, —C(=O)—O—; —O—C(=O)—, and —N(R$_1$)—; wherein R$_1$ is selected from the group consisting of —H, C$_1$-C$_8$ alkyl, C$_1$-C$_8$ branched alkyl, C$_3$-C$_8$ cycloalkyl, and C$_3$-C$_8$ cycloaryl; wherein M$_2$ is selected from the group consisting of a single bond and C$_1$-C$_8$ alkyl, C$_1$-C$_8$ branched alkyl, C$_3$-C$_8$ cycloalkyl, and C$_3$-C$_8$ cycloaryl; wherein D is selected from the group consisting of —H, —OH, —N(R$_7$)(R$_8$), pentoses, hexoses,

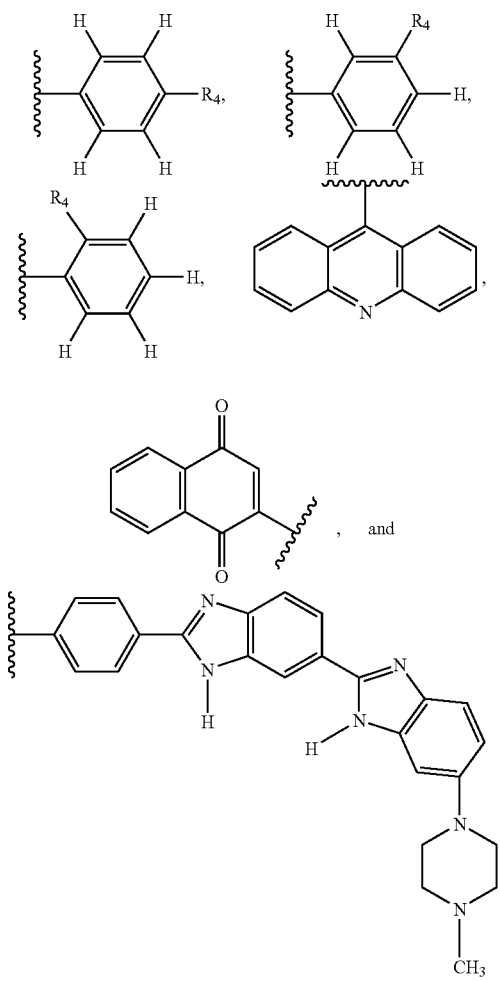

wherein $R_4$ is selected from the group consisting of —H, $C_1$-$C_8$ alkyl, $C_1$-$C_8$ branched alkyl, $C_3$-$C_8$ cycloalkyl, $C_3$-$C_8$ cycloaryl, —N($R_9$)($R_{10}$), and —CN; and wherein $R_7$, $R_8$, $R_9$ and $R_{10}$ are independently selected from the group consisting of —H, $C_1$-$C_8$ alkyl, $C_1$-$C_8$ branched alkyl, $C_3$-$C_8$ cycloalkyl, $C_3$-$C_8$ cycloaryl, and

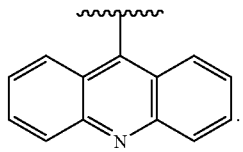

The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

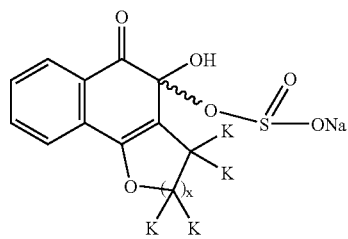

wherein x is an integer between 1 and 2; and each K is independently selected from the group consisting of H, $C_1$-$C_8$ alkyl, $C_1$-$C_8$ alkenyl, $C_1$-$C_8$ alkanol, $C_1$-$C_8$ alkoxy,

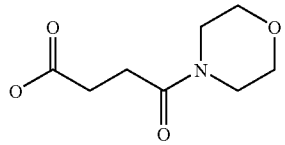

and where zero or two, but no more than two, vicinal K's in the molecule represent single electrons which form a pi bond, thus forming a double bond together with the existing sigma bond between the two adjacent carbons bearing the two vicinal K's.

The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

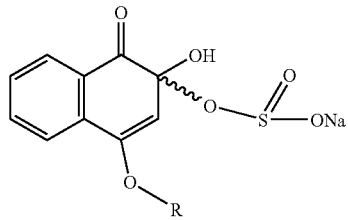

wherein R is selected from the group consisting of $C_1$-$C_8$ alkyl, $C_1$-$C_8$ cycloalkyl, $C_3$-$C_8$ cycloaryl, $C_1$-$C_8$ branched alkyl, and $C_1$-$C_8$ alkanol. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

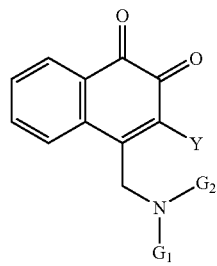

wherein Y is selected from the group consisting of —H, —F, —Br, —Cl, and —I; and wherein $G_1$ and $G_2$ are independently selected from the group consisting of H, $C_1$-$C_8$ alkyl,

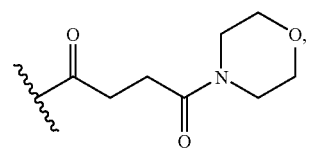

and —C(=O)—$CH_nX_{3-n}$, where n is an integer from 0 to 3 and X is selected from the group consisting of F, Cl, Br, and I. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

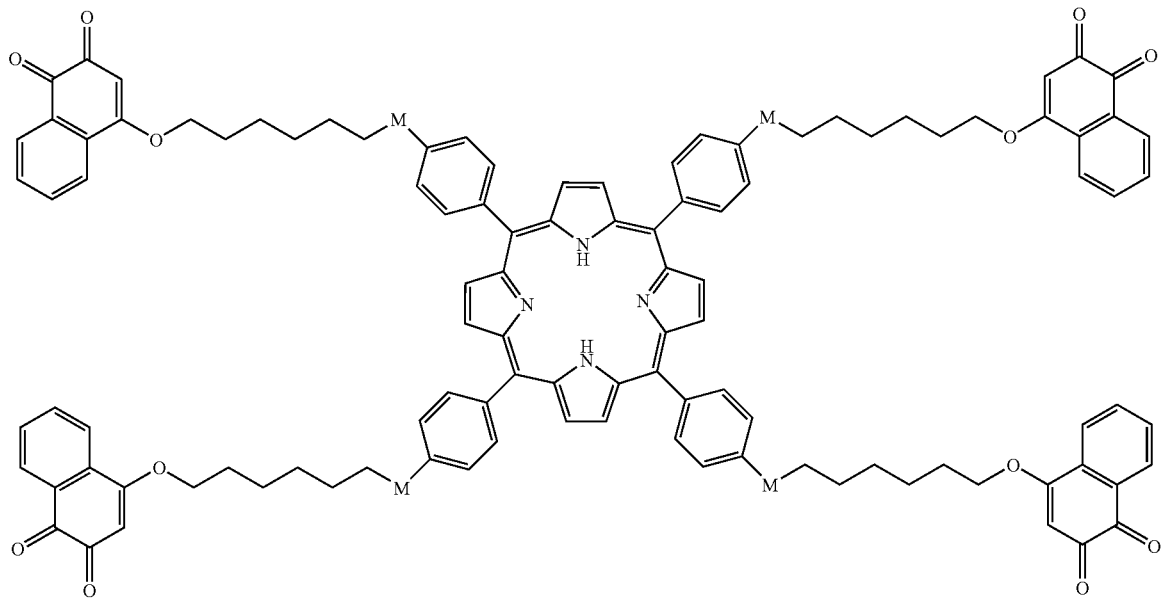

wherein M is selected from the group consisting of —O—, —C(=O)—O—, —O—(C=O)—, —C(=O)—N—, and —N—(C=O)—. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

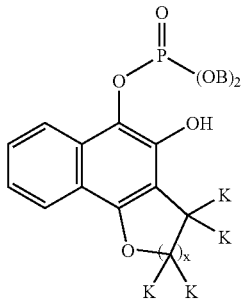

wherein x is an integer between 1 and 2; each B is independently selected from the group consisting of H, $C_1$-$C_8$ alkyl, $C_3$-$C_8$ cycloalkyl, $C_3$-$C_8$ cycloaryl, $C_1$-$C_8$ alkyl-$C_3$-$C_8$ cycloalkyl, and $C_1$-$C_8$ alkyl-$C_3$-$C_8$ cycloaryl; and each K is independently selected from the group consisting of H, OH, $C_1$-$C_8$ alkyl, $C_1$-$C_8$ alkenyl, $C_1$-$C_8$ alkanol, $C_1$-$C_8$ alkoxy, and where zero or two, but no more than two, vicinal K's in the molecule represent single electrons which form a pi bond, thus forming a double bond together with the existing sigma bond between the two adjacent carbons bearing the two vicinal K's. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

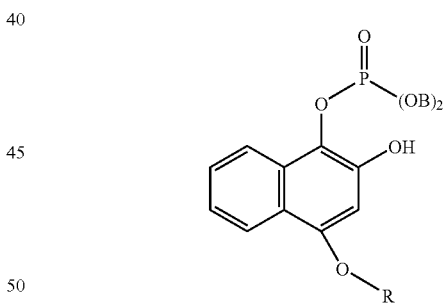

wherein each B is independently selected from the group consisting of H, $C_1$-$C_8$ alkyl, $C_3$-$C_8$ cycloalkyl, $C_3$-$C_8$ cycloaryl, $C_1$-$C_8$ alkyl-$C_3$-$C_8$ cycloalkyl, and $C_1$-$C_8$ alkyl-$C_3$-$C_8$ cycloaryl; and wherein R is selected from the group consisting of $C_1$-$C_8$ alkyl and $C_1$-$C_8$ alkanol. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

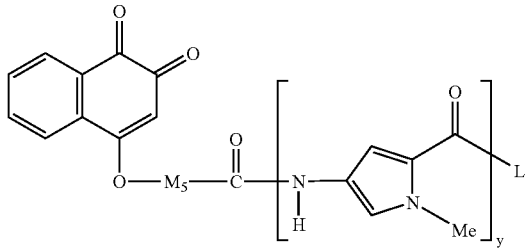

where $M_5$ is $C_1$-$C_8$ alkyl, y is an integer from 1 to 6, and L is selected from the group consisting of —O—$K_1$ or —N($K_1K_2$); where $K_1$ and $K_2$ are independently selected from the group consisting of H, $C_1$-$C_8$ alkyl, $C_1$-$C_8$ alkyl-COOH, $C_1$-$C_8$ alkyl-COOH, $C_1$-$C_8$ alkyl, $C_1$-$C_8$ alkyl-N($G_1G_2$), and $C_1$-$C_8$ alkyl-N($G_3$)—$C_1$-$C_8$ alkyl-N($G_4G_5$); and wherein each of $G_1$, $G_2$, $G_3$, $G_4$, and $G_5$ is independently selected from the group consisting of H and $C_1$-$C_8$ alkyl. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

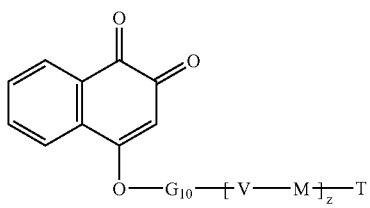

where z is an integer between one and ten; $G_{10}$ is selected from the group consisting of $C_1$-$C_8$ alkyl; each M is independently selected from the group consisting of $C_1$-$C_8$ alkyl; each V is selected from the group consisting of —C(=O)—N— and —N—(C=O)—; and T is selected from the group consisting of —COO$M_8$ and —CONM$_9$M$_{10}$, where each of $M_8$, $M_9$ and $M_{10}$ are independently selected from the group consisting of H and $C_1$-$C_8$ alkyl. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

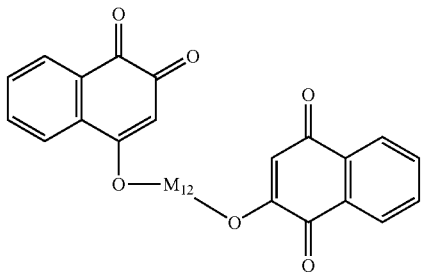

where $M_{12}$ is selected from the group consisting of $C_1$-$C_8$ alkyl.

In another embodiment, the invention comprises compounds of the formula

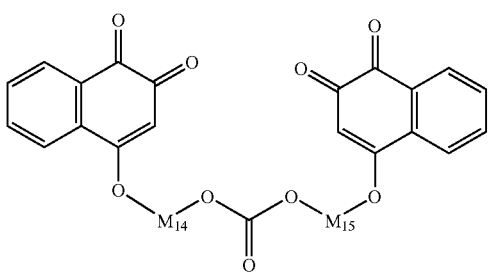

where $M_{14}$ and $M_{15}$ are independently selected from the group consisting of $C_1$-$C_8$ alkyl. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

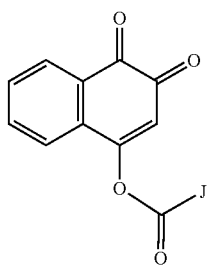

where J is selected from the group consisting of $C_1$-$C_8$ alkyl, $C_1$-$C_8$ cycloalkyl, $C_3$-$C_8$ cycloaryl, and $C_1$-$C_8$ branched alkyl. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention comprises compounds of the formula

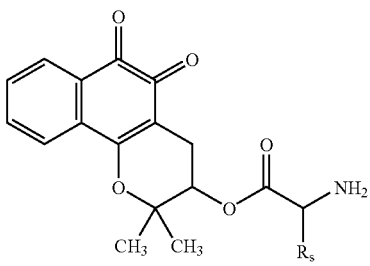

where $R_s$ is the side chain of a naturally-occuring amino acid. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

In another embodiment, the invention embraces compounds of the formula S-L-QUIN, where S represents a single amino acid or a peptide of at least two amino acids, L is a linking group containing at least one carbon, oxygen, or nitrogen atom attached covalently to both S and QUIN, or a nonentity; and QUIN is a quinone, quinone derivative, hydroquinone, or hydroquinone derivative. In a preferred embodiment, S or a portion thereof, S-L or a portion thereof, or both S or a portion thereof and then L or a portion thereof, are cleaved from the quinone-containing remainder of the molecule by an enzyme, such as the enzyme prostate specific antigen. In another preferred embodiment, L is —O—, —NH—, or —NH—($C_1$-$C_8$ alkyl)-O—. In yet another preferred embodiment, L is —NH—($C_6H_4$)$CH_2$—O—(C=O)—NH—($C_1$-$C_8$ alkyl)-O—. A preferred peptide for the S moiety is X-Ser-Lys-Leu-Gln, where X is a protecting group or an amino-terminal capping group, and the side chains of Ser, Lys, and Gln may optionally be protected with protecting groups. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

The invention also embraces compounds of the formula S-L-QUIN, wherein S represents a single amino acid or a peptide of at least two amino acids; L is a linking group containing at least one carbon, oxygen, or nitrogen atom attached covalently to both S and QUIN, or a nonentity; and QUIN is selected from the group consisting of the any of the above-mentioned quinone compounds which have a reactive group capable of being conjugated with an amino or carboxyl group, as well as the compounds

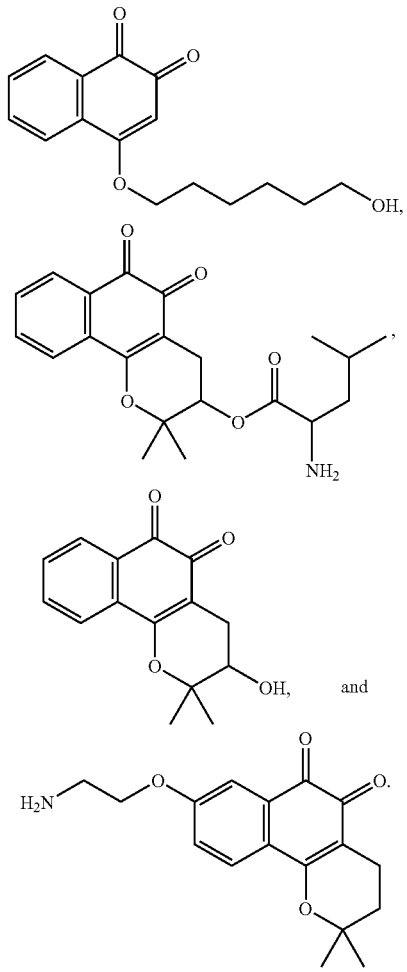

The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

The invention also encompasses a method for making the above-described compounds of formula S-L-QUIN, comprising the steps of a) covalently linking L to S, and b) covalently linking L to QUIN. Steps a) and b) can be performed in either order or simultaneously.

The invention also encompasses compounds of the formula

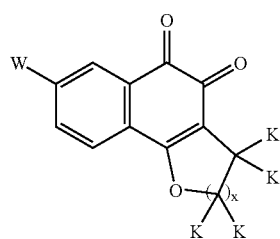

where x is an integer between 1 and 2; W is selected from —H, —OH, —O—$C_1$-$C_8$ alkyl, —O—$C_1$-$C_8$ alkyl-$NH_2$, and —O—$C_1$-$C_8$ alkyl-NH—S, wherein S is a single amino acid or a peptide of two or more amino acids; and each K is independently selected from the group consisting of H, OH, $C_1$-$C_8$ alkyl, $C_1$-$C_8$ alkenyl, $C_1$-$C_8$ alkanol, $C_1$-$C_8$ alkoxy, and where zero or two, but no more than two, vicinal K's in the molecule represent single electrons which form a pi bond, thus forming a double bond together with the existing sigma bond between the two adjacent carbons bearing the two vicinal K's. In a preferred embodiment, W is —O—$C_1$-$C_8$ alkyl-NH—S, S is a single amino acid or a peptide of two or more amino acids; and the group —NH— forms an amide bond with the alpha-carboxy group of S when S is a single amino acid. Alternatively, the group —NH— forms an amide bond with the C-terminal alpha-carboxy group of S when S is a peptide of two or more amino acids. A preferred subset of the above compounds are the compounds of the formula

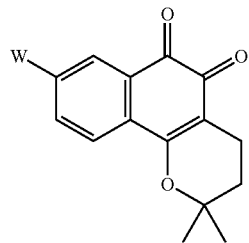

where W is selected from —H, —OH, —O—$C_1$-$C_8$ alkyl, —O—$C_1$-$C_8$ alkyl-$NH_2$, and —O—$C_1$-$C_8$ alkyl-NH—S, and wherein S is a single amino acid or a peptide of two or more amino acids. In a preferred embodiment, W is —O—$C_1$-$C_8$ alkyl-NH—S, S is a single amino acid or a peptide of two or more amino acids, and the group —NH— forms an amide bond with the alpha-carboxy group of S when S is a single amino acid. Alternatively, the group —NH— forms an amide bond with the C-terminal alpha-carboxy group of S when S is a peptide of two or more amino acids. The invention also comprises the above compounds in combination with a pharmaceutically acceptable carrier. The invention also comprises use of the above compounds to treat an indication characterized by the proliferation of disease cells in an individual, comprising administering to the individual a therapeutic amount of one or more of the above compounds, optionally together with another therapeutically effective compound or compounds.

The invention also includes all salts, stereoisomers, and tautomers of the foregoing compounds, unless explicitly indicated otherwise.

In another embodiment, the invention comprises any one or more of the foregoing compounds, optionally in combination with another therapeutic compound, combined with a pharmaceutically acceptable excipient or carrier.

The invention also provides methods of treating an indication comprising the step of administering to the individual an effective amount of a composition comprising a novel quinone. In one embodiment, the invention comprises a method of treating an indication characterized by the proliferation of disease cells in an individual comprising administering to the individual a therapeutic amount of any of the foregoing compounds. In one method, the indication is cancer. In various embodiments, the cancer affects cells of the bladder, blood, brain, breast, colon, digestive tract, lung, ovaries, pancreas, prostate gland, or skin. In other embodiments, the indication can also include, but is not limited to, Alzheimer's disease, epilepsy, multiple sclerosis, problems associated with tissue grafts and organ transplants, psoriasis, restenosis, stomach ulcers, or tissue overgrowth after surgery. In other embodiments, the indication is an infection or infestation of parasites, bacteria, fungi or insects.

BRIEF DESCRIPTION OF THE DRAWINGS

FIG. 2 depicts Scheme 2, illustrating the synthetic preparation of additional compounds of the invention.

FIG. 13 depicts Scheme 13, illustrating synthetic preparation of peptides conjugated to certain quinone compounds.

FIG. 14 depicts Scheme 14, illustrating additional synthetic preparation of peptides conjugated to certain quinone compounds.

MODES FOR CARRYING OUT THE INVENTION

Figure 1:
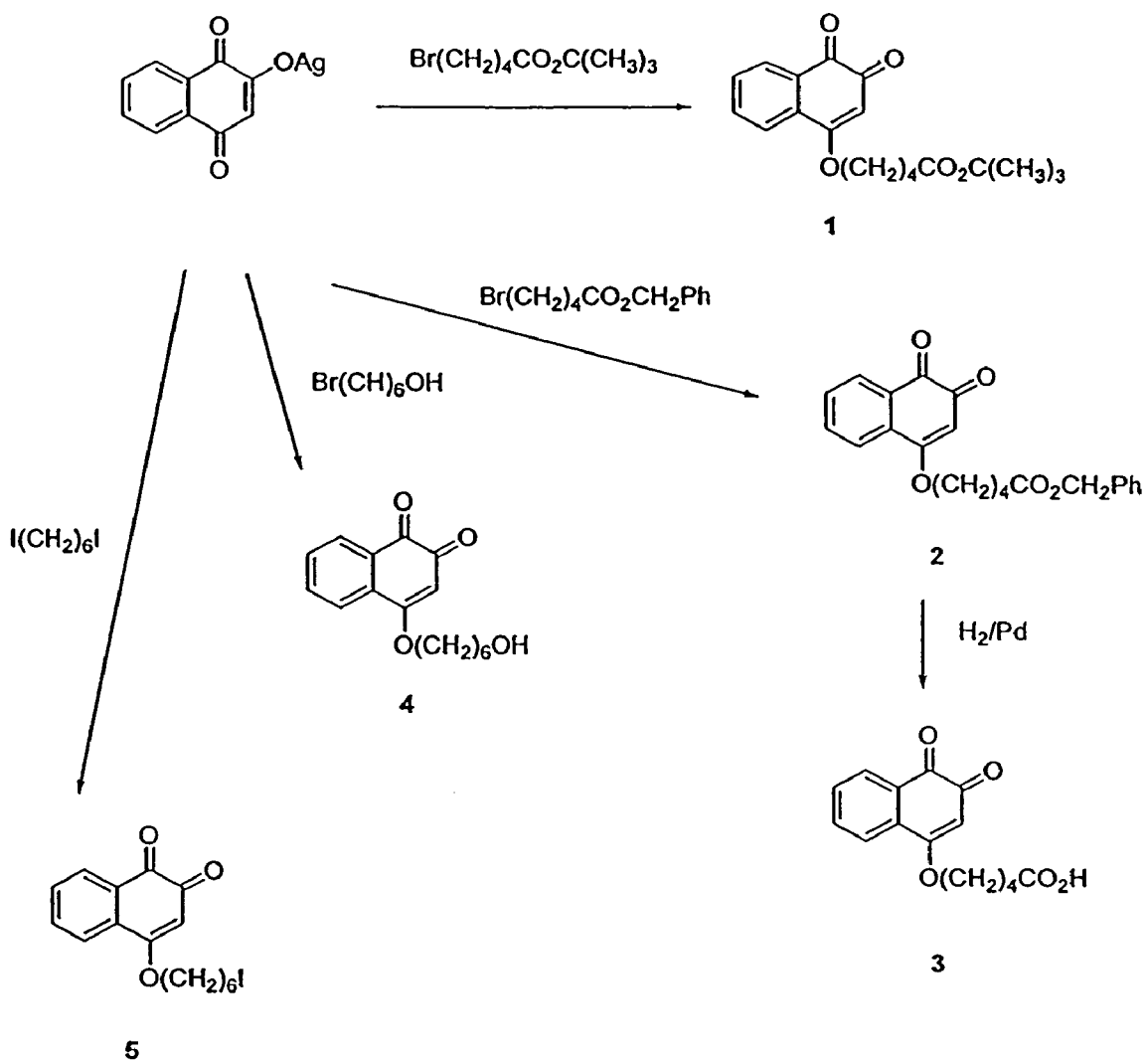
FIG. 1 depicts Scheme 1, illustrating the synthetic preparation of certain compounds of the invention.
Figure 3:
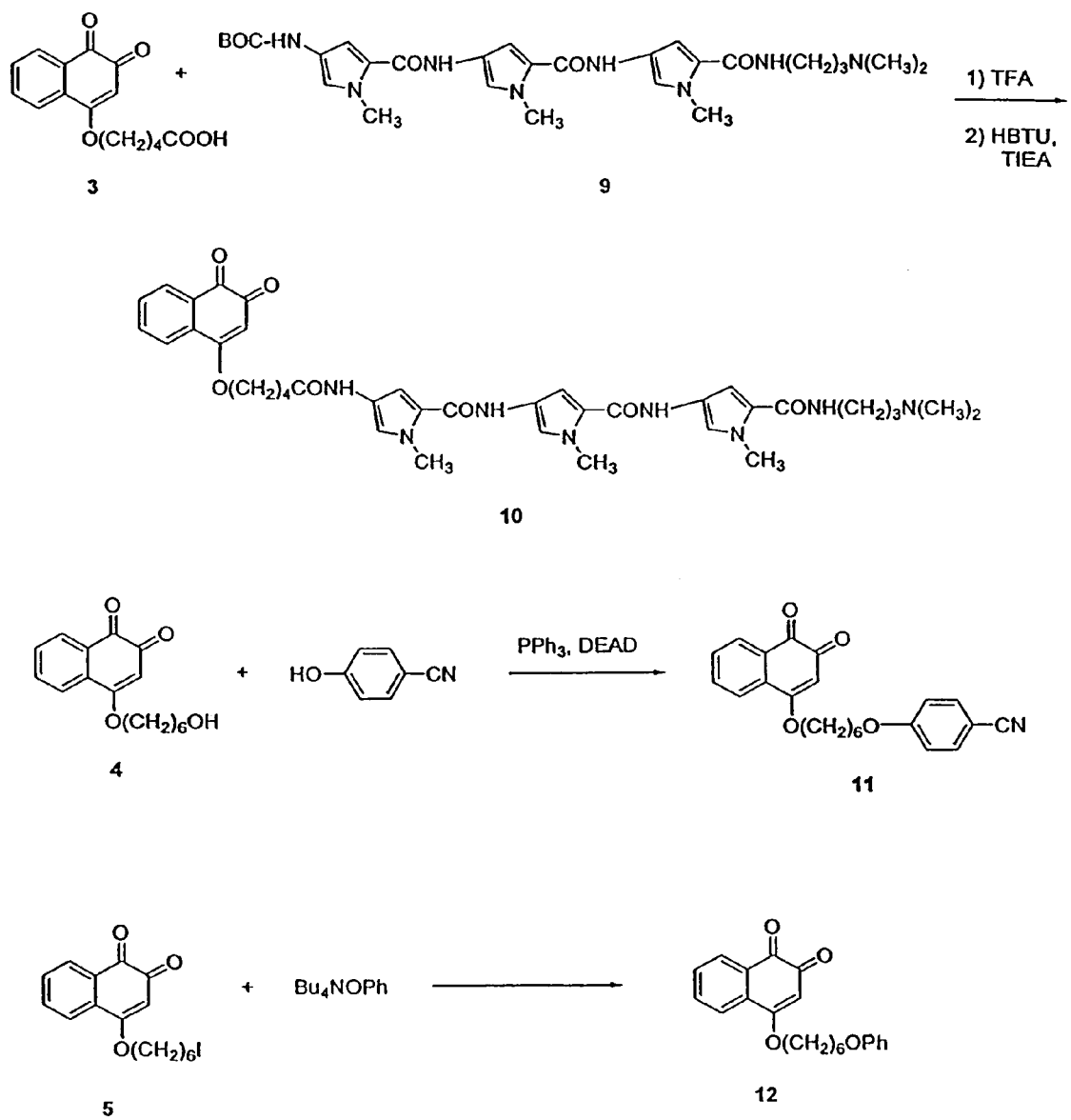
FIG. 3 depicts Scheme 3, illustrating the synthetic preparation of additional compounds of the invention.
Figure 4:
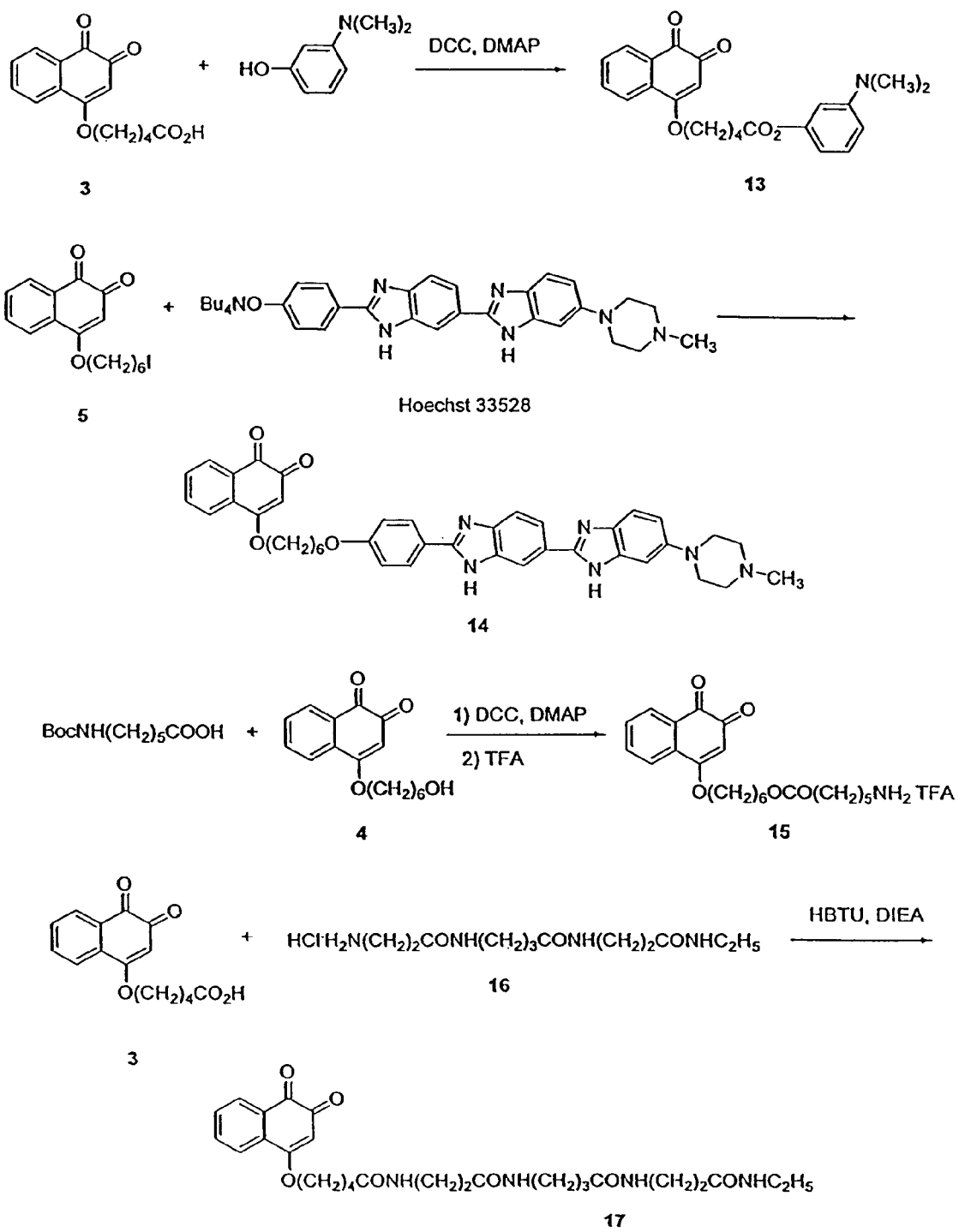
FIG. 4 depicts Scheme 4, illustrating the synthetic preparation of additional compounds of the invention.
Figure 5:
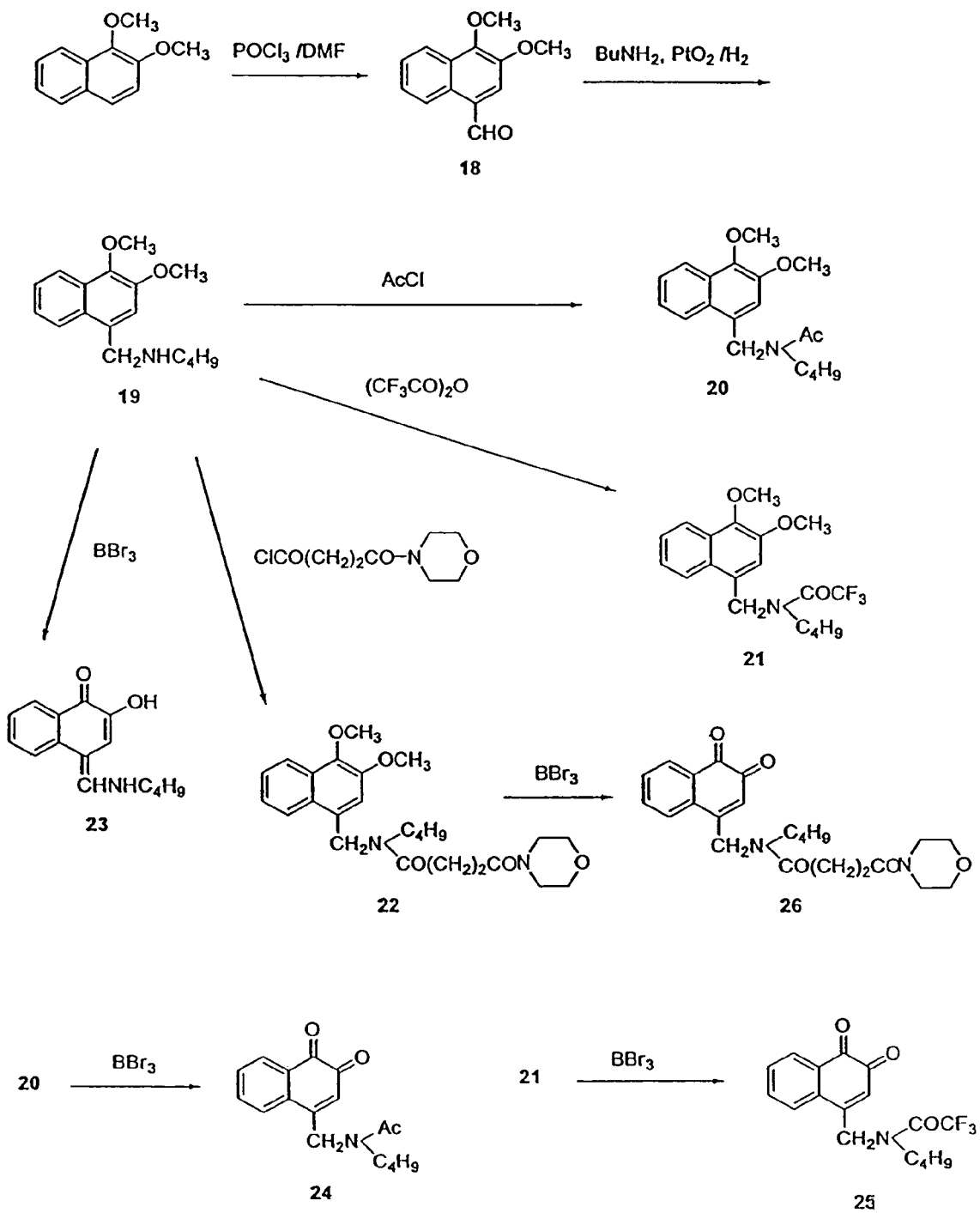
FIG. 5 depicts Scheme 5, illustrating the synthetic preparation of additional compounds of the invention.
Figure 6:
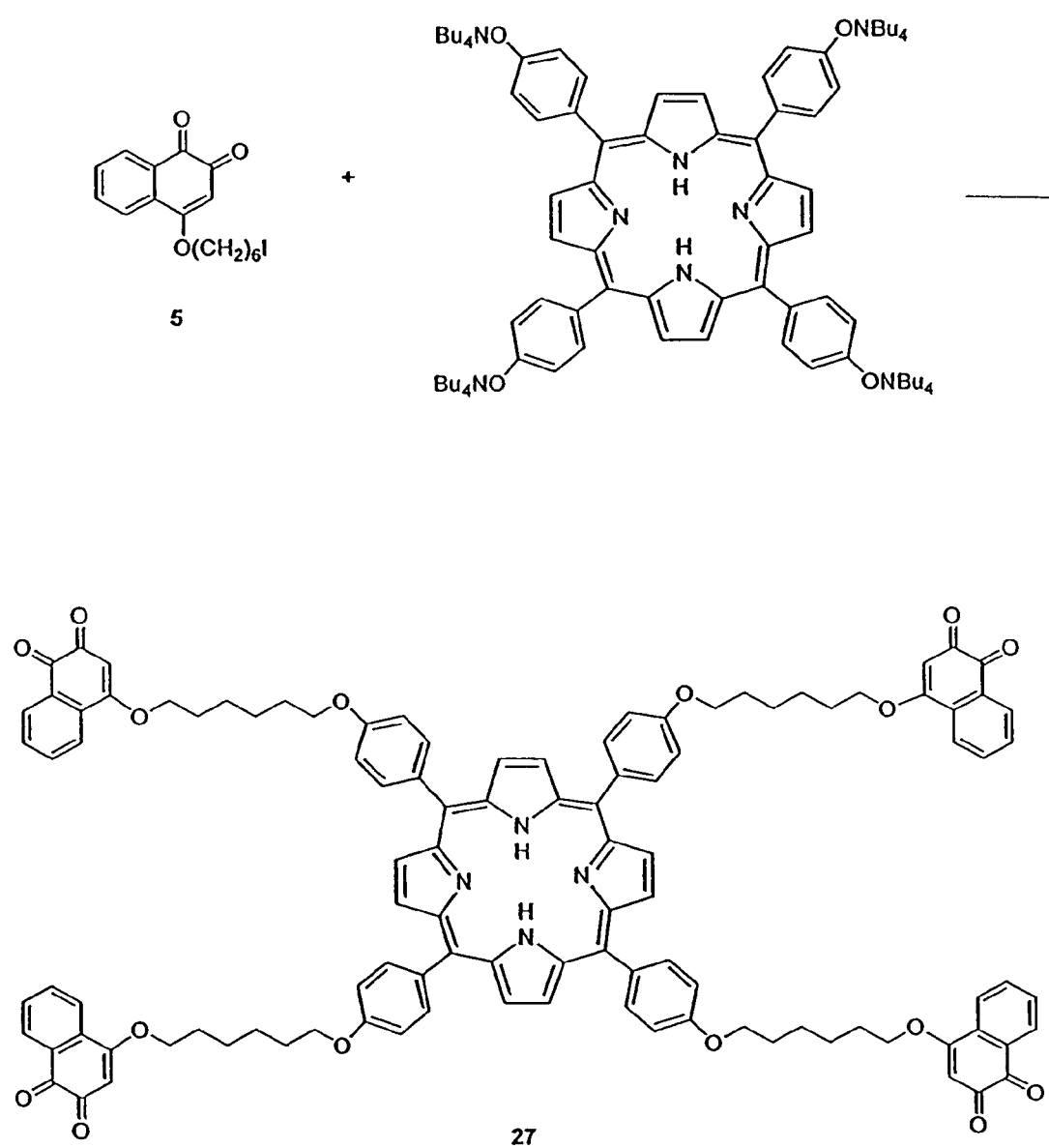
FIG. 6 depicts Scheme 6, illustrating the synthetic preparation of additional compounds of the invention.
Figure 7:
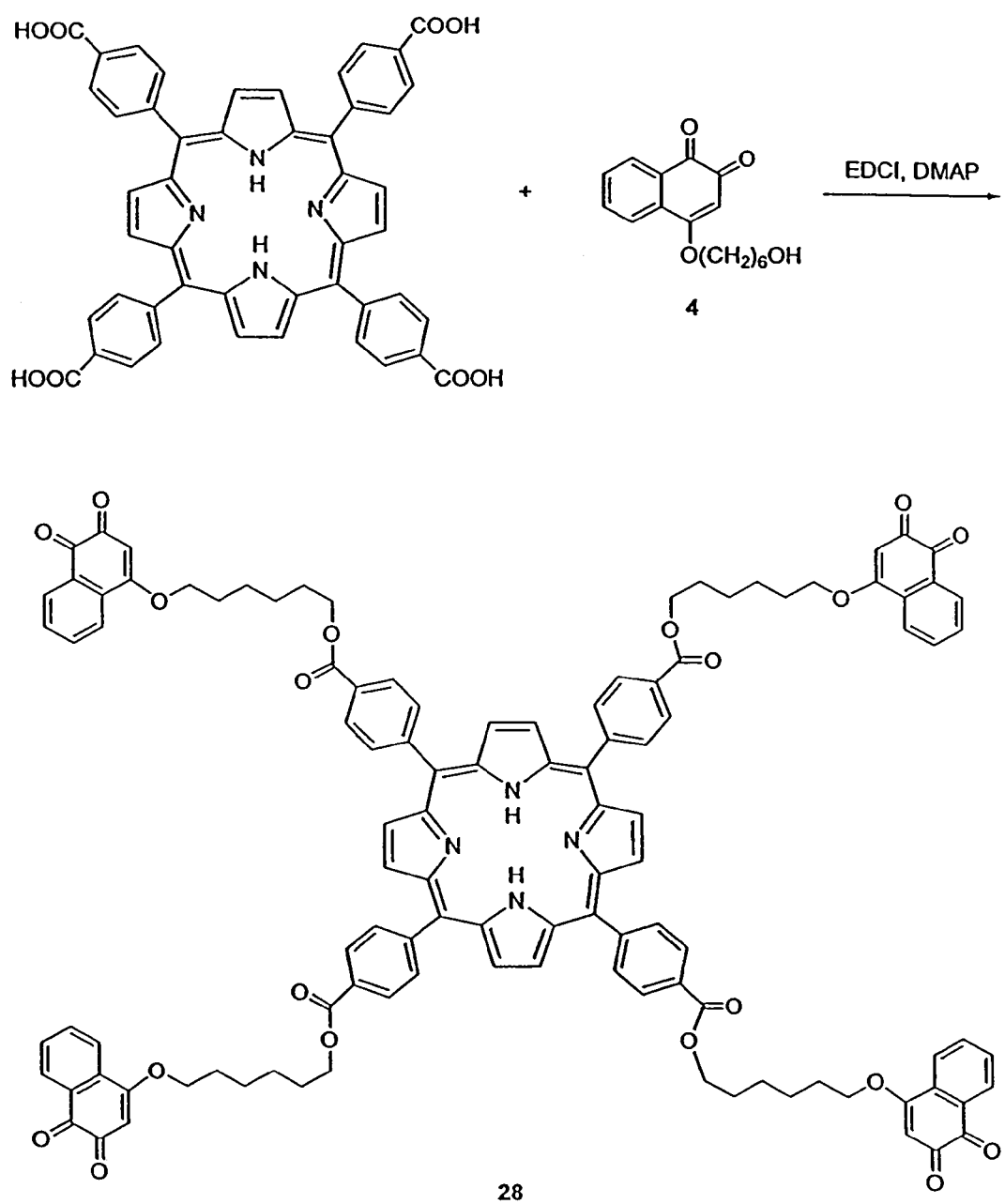
FIG. 7 depicts Scheme 7, illustrating the synthetic preparation of additional compounds of the invention.
Figure 8:
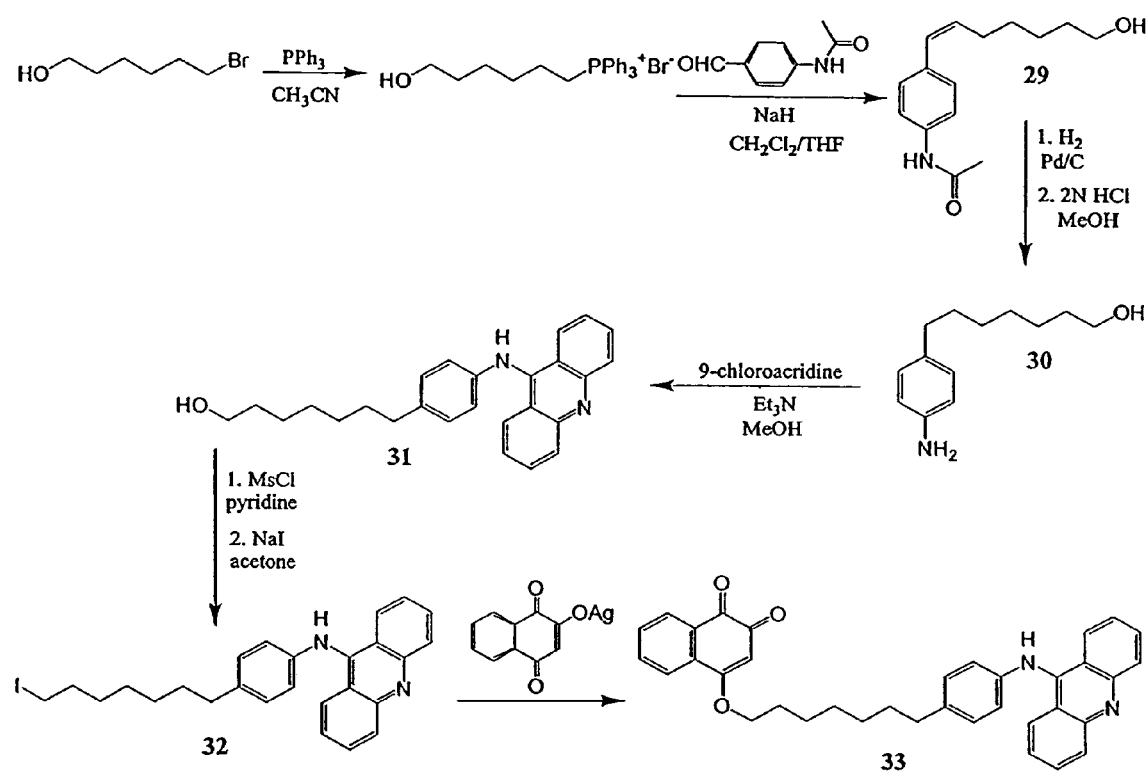
FIG. 8 depicts Scheme 8, illustrating the synthetic preparation of additional compounds of the invention.
Figure 9:
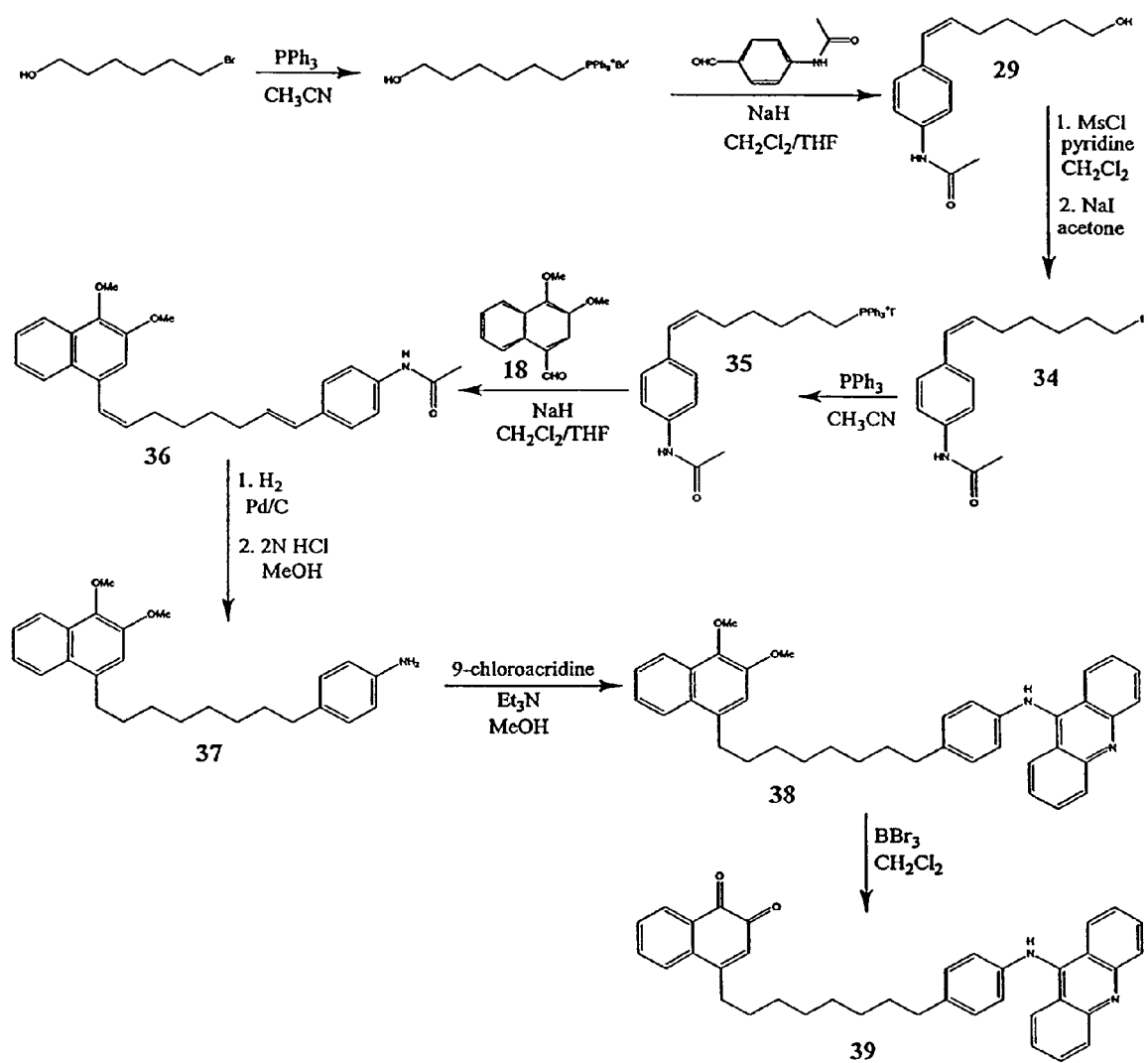
FIG. 9 depicts Scheme 9, illustrating the synthetic preparation of additional compounds of the invention.
Figure 10:
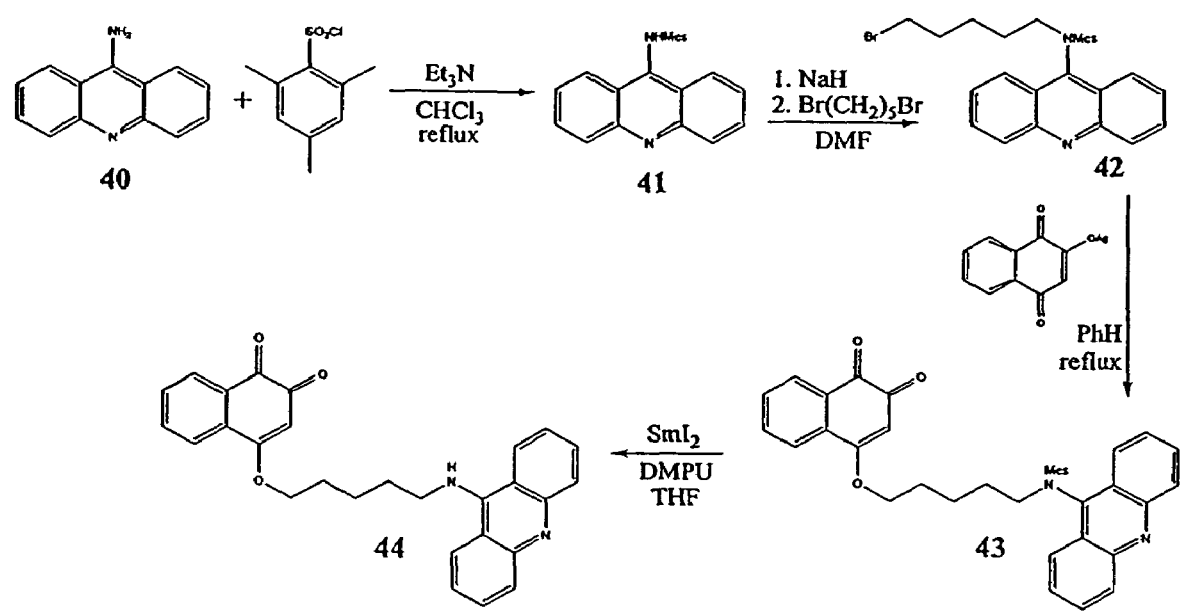
FIG. 10 depicts Scheme 10, illustrating the synthetic preparation of additional compounds of the invention.
Figure 11:
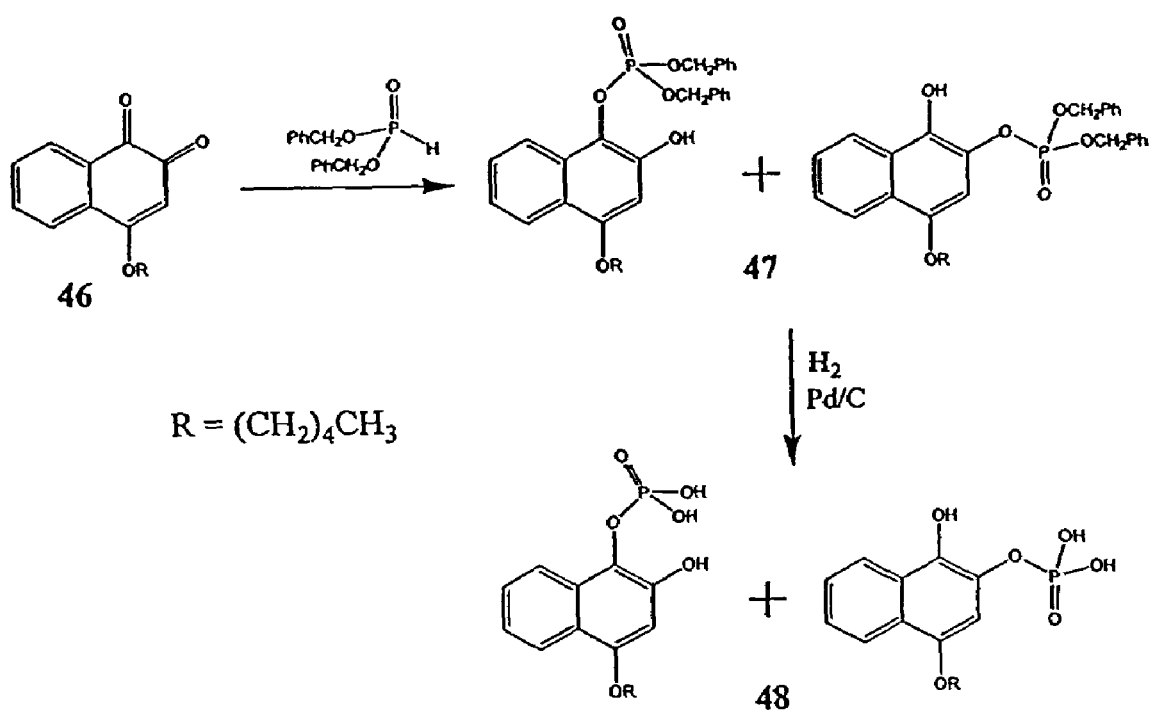
FIG. 11 depicts Scheme 11, illustrating the synthetic preparation of additional compounds of the invention.
Figure 12:
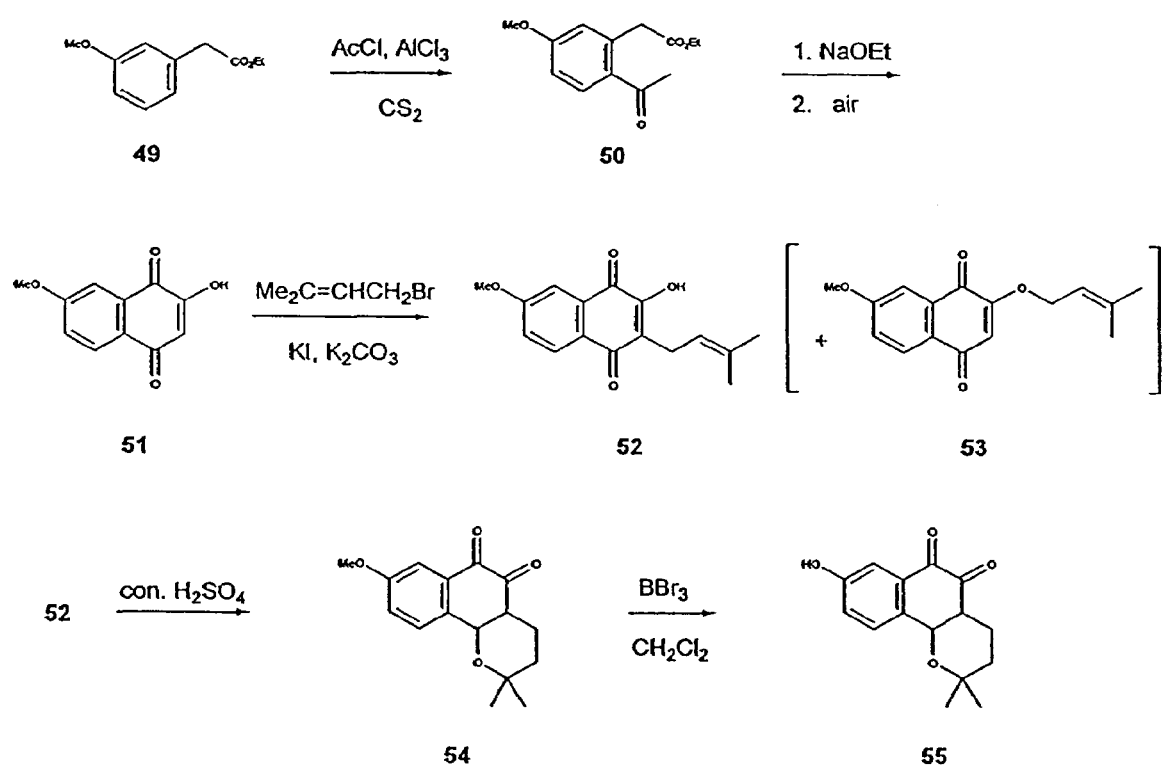
FIG. 12 depicts Scheme 12, illustrating the synthetic preparation of additional compounds of the invention.

The present invention encompasses novel quinones and methods of their use. Such methods include treating indications in an individual comprising the step of administering to the individual an effective amount of a novel quinone. The indications include cancer. In various embodiments, the cancer affects cells of the bladder, blood, brain, breast, colon, digestive tract, lung, ovaries, pancreas, prostate gland, or skin. In other embodiments, the indication can also include, but is not limited to, Alzheimer's disease, epilepsy, multiple sclerosis, problems associated with tissue grafts and organ transplants, psoriasis, restenosis, stomach ulcers, or tissue overgrowth after surgery. In other embodiments, the indication is an infection or infestation of parasites, bacteria, fungi or insects. The invention also includes industrial uses of these novel quinones, such as uses as pigments or dyes, as laxatives and worming agents, in cosmetics, histology and paint-making, in photography, in tanning hides, in strengthening animal fibers, and as a reagent.

Definitions

By a "quinone" is meant any of a group of aromatic dioxo compounds derived from benzene or multiple-ring hydrocarbons such as naphthalene, anthracene, etc. They are classified as benzoquinones, naphthoquinones, anthraquinones, etc., on the basis of the ring system. The C=O groups are generally ortho or para, and form a conjugated system with at least two C=C double bonds; hence the compounds are colored, yellow, orange or red. This type of chromophore is found in many natural and synthetic pigments. Exemplary quinones include 2,5-cyclohexadiene-1,4-dione, which is useful as an oxidizing agent, in photography, in manufacturing dyes and hydroquinone, in tanning hides, in strengthening animal fibers, and as a reagent; and various 1,2-naphthoquinones, which have medicinal uses. Frydman et al. (1997) Cancer Res. 57:620-627. By "hydroquinone" is meant the reduced form of any quinone; for example, the reduced form of 1,4-benzoquinone is 1,4-dihydroxybenzene (p-dihydroxybenzene).

An "indication" includes any symptom or the like which points out a suitable remedy or treatment or which shows the presence of a disease. As used herein, an "indication" also includes a "disease" itself, where a disease is a condition of an organ, part, structure or system of the body in which there is incorrect function resulting from the effect(s) of heredity, infection, diet and/or environment. The indication can be characterized by proliferation of diseased cells, such as cancer. By "cancer" is meant the abnormal presence of cells which exhibit relatively autonomous growth, so that they exhibit an aberrant growth phenotype characterized by a significant loss of cell proliferation control. Cancerous cells can be benign or malignant. In various embodiments, the cancer affects cells of the bladder, blood, brain, breast, colon, digestive tract, lung, ovaries, pancreas, prostate gland, or skin. In other embodiments, the indication can also include, but is not limited to, Alzheimer's disease, epilepsy, multiple sclerosis, problems associated with tissue grafts and organ transplants, psoriasis, restenosis, stomach ulcers, or tissue overgrowth after surgery. In other embodiments, the indication is an infection or infestation of parasites, bacteria, fungi or insects.

By "DNA toposiomerase II" is meant is the scaffold protein capable of cleaving double-stranded DNA, passing an uncut portion of the DNA between the cut ends, and resealing the cut. DNA topoisomerase II ("topo II") is critical in DNA replication, because it can unknot tangles of DNA that would otherwise form as the long parental strands unwind and daughter strands are synthesized. During cleavage by topo II, the free 5' phosphates on the DNA strands become covalently linked to tyrosine side chains of the enzyme. Staining of metaphase chromosomes with fluorescent antibodies raised against highly purified topo II demonstrates that this enzyme is associated with the chromosome scaffold. Even in interphase chromosomes, which are not as condensed as metaphase chromosomes, the DNA remains associated with topo II and hence with the chromosome scaffold. During interphase, proteins, including topo II, are bound to fixed sites in mammalian DNA that are 30-90 kb apart. The binding sites for topo II are called scaffold-associated regions (SARs), which occur between but not within transcription units. DNA topoisomerase II is reviewed and discussed in, for example, Austin et al. (1998) *Bioessays* 20:215-26; Larsen et al. (1996) *Prog. Cell Cycle Res.* 2:229-39; Chaly et al. (1996) *Chromosome Res.* 4:457-66; Kimura et al. (1994) *J. Biol. Chem.* 269:1173-6; and Roca et al. (1993) *J. Biol. Chem.* 268:14250-5.

An "individual" is a vertebrate, preferably a mammal, more preferably a human. Mammals include, but are not limited to, farm animals, sport animals, rodents, primates, and pets.

An "effective amount" or "therapeutic amount" is an amount sufficient to effect beneficial or desired clinical results. An effective amount can be administered in one or more administrations. For purposes of this invention, an effective amount of a quinone is an amount that is sufficient to palliate, ameliorate, stabilize, reverse, slow or delay the progression of the disease state. A therapeutic amount of a quinone of the present invention is an amount sufficient to inhibit proliferation of diseased cells. A quinone is considered to be an effective agent if it is effective against at least one disease or in at least one application, even if it is not effective against another disease or in another application.

As used herein, "treatment" is an approach for obtaining beneficial or desired clinical results. For purposes of this invention, beneficial or desired clinical results include, but are not limited to, alleviation of symptoms, diminishment of extent of disease, stabilization (i.e., not worsening) of state of disease, prevention of spread (i.e., metastasis) of disease, delay or slowing of disease progression, amelioration or palliation of the disease state, improvement in quality of enjoyment of life, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering quinones of the present invention.

The invention includes all salts of the compounds described herein. Particularly preferred are pharmaceutically acceptable salts. Pharmaceutically acceptable salts are those salts which retain the biological activity of the free acids or bases and which are not biologically or otherwise undesirable. The desired salt may be prepared by methods known to those of skill in the art by treating an amine-containing quinone with an acid, or by treating an acid-containing quinone with a base. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Examples of bases include, but are not limited to, sodium hydroxide and potassium hydroxide (which yield sodium and potassium salts, respectively), triethylamine, and t-butylamine.

The invention also includes all stereoisomers of the compounds, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

The term "alkyl" refers to saturated aliphatic groups including straight-chain, branched-chain, cyclic groups, and combinations thereof, having the number of carbon atoms specified, or if no number is specified, having up to 12 carbon atoms. Examples of alkyl groups include, but are not limited to, groups such as methyl, ethyl, n-propyl, isopropyl, n-butyl, isobutyl, sec-butyl, t-butyl, n-pentyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl. Alkyl groups may be unsubstituted, or may be substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —$CF_3$, —$CF_2$—$CF_3$, and other perfluoro and perhalo groups.

The term "alkenyl" refers to unsaturated aliphatic groups including straight-chain, branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —$CH_2$—CH=CH—$CH_3$ and —$CH_2$—$CH_2$-cyclohexenyl, there the ethyl group can be attached to the cyclohexenyl moiety at any available carbon valence. The term "alkynyl" refers to unsaturated aliphatic groups including straight-chain, branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. Substituted aryls can be substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—CH($CH_3$)—S—$CH_3$, —$CH_2$—$CH_2$—NH—$CH_2$—$CH_2$—,1-ethyl-6-propylpiperidino, 2-ethylthiophenyl, and morpholino. Examples of heteroalkenyl groups include, but are not limited to, groups such as —CH=CH—NH—CH($CH_3$)—$CH_2$—. "Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Heteroalkyl, heteroalkenyl, heteroalkynyl and heteroaryl groups can be unsubstituted or substituted with one or more substituents, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—$SO_2$-phenyl, —NH—(C=O)O-alkyl, —NH—(C=O)O-alkyl-aryl, and —NH—(C=O)-alkyl. The heteroatom(s) as well as the carbon atoms of the group can be substituted. The heteroatom(s) can also be in oxidized form. Unless otherwise specified, heteroalkyl, heteroalkenyl, heteroalkynyl, and heteroaryl groups have between one and five heteroatoms and between one and twenty carbon atoms.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The terms "halo" and "halogen" as used herein refer to Cl, Br, F or I substituents.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis,* 2nd Ed. (John Wiley & Sons, Inc., New York). Preferred amino protecting groups include, but are not limited to, benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Preferred hydroxylprotecting groups include Fmoc, benzyl, t-butyl, TBDIMS, photolabile protecting groups (such as nitroveratryl oxymethyl ether (Nvom)), Mom (methoxy methyl ether), and Mem (methoxy ethoxy methyl ether). Particularly preferred protecting groups include NPEOC (4-nitrophenethyloxycarbonyl) and NPEOM (4-nitrophenethyloxymethyloxycarbonyl). Amino acid protecting groups are well-known in the field of peptide synthesis, and include groups such as those disclosed in Stewart, J. M. and Young, J. D., *Solid Phase Peptide Synthesis, 2nd Ed.*, Pierce Chemical Company: Rockford, Ill., 1984; Atherton, E. and Sheppard, R. C., *Solid Phase Peptide Synthesis: A Practical Approach*, IRL Press: New York, 1989; Jones, J., *The Chemical Synthesis of Peptides (International Series of Monographs on Chemistry, No. 23)*, Clarendon Press: Oxford, 1991; Bodanszky, M., *The Practice of Peptide Synthesis*, Springer-Verlag: New York, 1984; Bodanszky, M., *Peptide Chemistry: A Practical Textbook, 2nd Ed.*, Springer-Verlag: New York, 1993; Bodanszky, M., *Principles of Peptide Synthesis, 2nd Ed.*, Springer-Verlag: New York, 1993; *Synthetic Peptides: A User's Guide* (Grant, G. A., Ed.), W.H. Freeman: New York, 1992; and Barany, G. and Merrifield, R. B., "Solid Phase Peptide Synthesis", Chapter 1 (pp. 1-284) of *The Peptides*, Vol. 2, Academic Press: New York, 1979. Additional publications include the 97/98 Novabiochem Catalog and Peptide Synthesis Handbook and the Novabiochem Combinatorial Chemistry Catalog (Calbiochem-Novabiochem, San Diego, Calif.), and the user's manuals and synthesis bulletins for Perkin-Elmer Applied Biosystems (Foster City, Calif.) peptide synthesizers. Purification methods appropriate for peptides are discussed in the references cited above, and in *High-Performance Liquid Chromatography of Peptides and Proteins: Separation, Analysis and Conformation* (Mant, C. T. and Hodges, R. S., Eds.), CRC Press: Boca Raton, Fla., 1991. Materials for use in peptide synthesis, such as protected amino acids, synthesis reagents, solvents, and resin supports, are available commercially from a number of suppliers, including Calbiochem-Novabiochem, San Diego, Calif.; Advanced Chemtech, Louisville, Ky.; Bachem Bioscience, Inc., King of Prussia, Pa.; Sigma Chemical Company, St. Louis, Mo.; Richelieu Biotechnologies, Inc., Montreal, Quebec, Canada; Peninsula Laboratories, Inc., Belmont, Calif.; Perkin-Elmer Applied Biosystems, Inc., Foster City, Calif.; and Peptides International, Louisville, Ky.

An "amino-capping group" or "amino-terminal capping group" or "N-terminal capping group" is a group that covalently links to an amino group. Examples of amino-capping groups include, but are not limited to, 4-morpholinocarbonyl, acetyl, and trifluoroacetyl.

Novel Quinones

The present invention encompasses novel quinones. While not wishing to be bound by any particular theory explaining quinone toxicity, the inventors suggest that the novel quinones can be designed based on the suspected DNA topoisomerase II-poisoning activity of quinones. Alternatively, quinone toxicity may be related to the compound's potential to undergo redox cycling with the formation of highly reactive oxygen species. O'Brien (1991) *Chem. Biol. Interactions* 80:1-41. In the next step, the quinone is tested in vitro for efficacy in inhibiting proliferation of diseased cells (such as tumor cells). If it is efficable, the quinone is then tested in animals, such as nude mice with tumor xenografts. Simultaneously, toxicity of the compound should be determined. If the quinone is found to efficable and safe, testing can then proceed to human trials.

In Vitro Testing of Novel Quinones

Novel quinones of the present invention can be tested in vitro by any means known in the art. The quinones can be tested, for example, for toxicity against a chosen cell line, such as a tumor cell line.

In Vivo Testing of Novel Quinones

Following a showing of efficacy of the novel quinones in vitro, these compounds can be tested in vivo. Typical tests include, but are not limited to, examinations of the effects of compound administration on animals, such as nude mice with tumor xenografts.

Methods of Administrating Quinones

The novel quinone compounds of the present invention can be administered to an individual via any route known in the art, including, but not limited to, those disclosed herein. Preferably administration of the novel quinones is intravenous. Other methods of administration include but are not limited to, oral, intrarterial, intratumoral, intramuscular, subcutaneous, intraperitoneal, gastrointestinal, and directly to a specific or affected organ. The novel quinone compounds described herein are administratable in the form of tablets, pills, powder mixtures, capsules, injectables, solutions, suppositories, emulsions, dispersions, food premixes, and in other suitable forms. Additional methods of administration are known in the art. The pharmaceutical dosage form which contains the compounds described herein is conveniently admixed with a non-toxic pharmaceutical organic carrier or a non-toxic pharmaceutical inorganic carrier. Typical pharmaceutically-acceptable carriers include, for example, mannitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying, preserving, or wetting agents, and the like. A suitable carrier is one which does not cause an intolerable side effect, but which allows the novel quinone compounds to retain its pharmacological activity in the body. Formulations for parenteral and nonparenteral drug delivery are known in the art and are set forth in *Remington's Pharmaceutical Sciences*, 18th Edition, Mack Publishing (1990). Solid forms, such as tablets, capsules and powders, can be fabricated using conventional tableting and capsule-filling machinery, which is well known in the art. Solid dosage forms can contain any number of additional non-active ingredients known to the art, including excipients, lubricants, dessicants, binders, colorants, disintegrating agents, dry flow modifiers, preservatives, and the like. Liquid forms for ingestion can be formulated using known liquid carriers, including aqueous and non-aqueous carriers, suspensions, oil-in-water and/or water-in-oil emulsions, and the like. Liquid formulations can also contain any number of additional non-active ingredients, including colorants, fragrance, flavorings, viscosity modifiers, preservatives, stabilizers, and the like. For parenteral administration, novel quinone compounds can be administered as injectable dosages of a solution or suspension of the compound in a physiologically acceptable diluent or sterile liquid carrier such as water or oil, with or without additional surfactants or adjuvants. An illustrative list of carrier oils would include animal and vegetable oils (peanut oil, soy bean oil), petroleum-derived oils (mineral oil), and synthetic oils. In general, for injectable unit doses, water, saline, aqueous dextrose and related sugar solutions, and ethanol and glycol solutions such as propylene glycol or polyethylene glycol are preferred liquid carriers. The pharmaceutical unit dosage chosen is preferably fabricated and administered to provide a final concentration of drug at the point of contact with the cancer cell of from 1 µM to 10 mM. More preferred is a concentration of from 1 to 100 μM. As with all pharmaceuticals, the optimal effective concentration of novel quinone compounds will need to be determined empirically and will depend on the type and severity of the disease, route of administration, disease progression and health and mass or body area of the patient. Such determinations are within the skill of one in the art.

The following examples are provided to illustrate, but not limit, the invention.

EXAMPLES

Example 1

Synthetic Preparation of Quinone Compounds

Preparation of quinones of the invention is described below and depicted in the Figures.

New chemistry was developed in order to construct drugs where the 1,2-naphthoquinone moiety is bound to a DNA minor groove binder unit or a DNA intercalator. While not wishing to limit the invention to any particular theory of operation, it is believed that the 1,2-naphthoquinone derivatives "poison" topoisomerase II and transform this essential DNA replication enzyme into a nuclease-type enzyme that cleaves DNA. It is postulated that this modification of topoisomerase II by the 1,2-naphthoquinones is very likely due to the alkylation of the thiol residues of the enzyme by the quinones (Michael additions).

Scheme 1 outlines derivatization reactions leading to 1,2-naphthoquinone intermediates. The silver salt of 2-hydroxy-1,4-naphthoquinone was alkylated with the tert-butyl or benzyl esters of 5-bromo-pentanoic acid to give either 1 or 2. The benzyl ester 2 was transformed into the acid 3 by hydrogenolysis. The silver salt was also alkylated with 6-bromohexanol to give 4, or with 1,6-diiodohexane to give 5. The alcohol 4 treated with triphosgene gives 6 (Scheme 2). The acid 3 can be derivatized by reaction with 3-amino-1-methyl-5-methyloxycarbonylpyrrole (Baird and Dervan (1996) *J. Am. Chem. Soc.* 118:6141) in the presence of o-benzotriazol-1-yl-N,N,N',N'-tetramethyluronium hexafluorophosphate (HBTU) and diisopropylethyl amine (DIEA) to give the amide 7. The silver salt of 2-hydroxy-1,4-naphthoquinone reacted with pivalyl chloride to give 8 (Scheme 2). Acid 3 was condensed with the polypyrrole amide 9 (Baird and Dervan (1996) *J. Am. Chem. Soc.* 118:6141) after cleavage of the protecting t-butyl group with TFA. The resulting product 10 is a molecule where the 1,2-naphthoquinone moiety is covalently bound to a DNA minor groove binder (Scheme 3). Alcohol 4 was condensed using the Mitsonobu reaction (triphenylphosphine, diethyl acetylenedicarboxylate) with 4-hydroxy-benzonitrile to give 11. Iodide 5 was reacted with the tetrabutyl ammonium salt of phenol to give 12.

The acid 3 was esterified with 3-dimethylaminophenol using dicyclohexylcarbodiimide (DCC) and 4-dimethylamino pyridine (DMAP) and gave 13. By reaction of 5 and the tetrabutylammonium salt of Hoechst 33528 it was possible to obtain 14, where the quinone is covalently bound to the DNA minor groove binder. By esterification of 4 with 6-aminohexanoic acid (used as its BOC derivative and deprotected with TFA) in the presence of DCC and DMAP, it was possible to obtain 15 as its trifluoroacetate (Scheme 4). By condensation of the acid 3 with the N-ethyl diamide 16, the polyamide quinone 17 was prepared (Scheme 4).

A new class of 4-aminoalkyl substituted 1,2-naphthoquinones was obtained following the outline depicted in Scheme 5. A Vilsmeier reaction on 1,2-dimethoxynaphthalene gave the formyl derivative 18. It was converted by reductive amination with n-butylamine into 19. Treatment of 19 with acetyl chloride gave 20, while treatment with trifluoroacetic anhydride gave 21 (Scheme 5). Acylation of 19 with morpholino succinyl chloride gave 22. Cleavage of the 1,2-dimethoxy groups of 19 with boron tribromide gave the quinone 23 which was found to exist in the p-quinonemethine form. Cleavage of the dimethoxy residues of 20 and 21 led to the expected quinones 24 and 25. Cleavage of the methoxy residues of 22 gave the quinone 26 (Scheme 5).

The 1,2-naphthoquinone residue was also covalently bound to a porphyrin backbone, since porphyrins are known to concentrate in cancer tissues. By reaction of the iodide 5 with the tetrabutylammonium salt of meso-p-hydroxyphenylporphyrin, the porphyrin quinone 27 was obtained (Scheme 6).

By esterification of 4,4',4'',4'''-(21H, 23H-porphine-5,10,15,20-tetrayl)tetrakis(benzoic acid) with the quinone alcohol 4 in the presence of EDCI (1,(3-dimethyl aminopropyl)-3-ethylcarbodiimide) and DMAP it was possible to prepare the quinone-porphyrin 28 (Scheme 7).

Synthesis of 1,2-Naphthoquinones Bound to DNA Intercalators

It is known that 4-aminoacridine derivatives intercalate in the DNA helix. Therefore syntheses of 1,2-naphthoquinone residues bound to 4-aminoacridine derivatives were designed (Scheme 8). The salt (6-hydroxyhexyl)triphenylphosphonium bromide was prepared by the reaction of 6-bromohexanol with triphenylphosphine in refluxing acetonitrile. Wittig reaction of (6-hydroxyhexyl)triphenylphosphonium bromide with 4-acetamidobenzaldehyde produced alkene 29 as a mixture of E and Z isomers. Reduction of the double bond ($H_2$, Pd/C) and acidic hydrolysis (2N HCl, MeOH) afforded 4-(7-hydroxyheptyl)-aniline 30. Aniline 30 was reacted with 9-chloroacridine in MeOH in the presence of triethylamine to give alcohol 31. Alcohol 31 was converted to iodide 32 by reaction with methanesulfonyl chloride in pyridine, followed by reaction with sodium iodide in acetone. Reaction of iodide 32 with the silver salt of 2-hydroxy-1,4-naphthoquinone afforded quinone 33 as a mixture of ortho- and para-quinone isomers. The ortho- and para-quinone isomers could be separated and purified by column chromatography.

A second approach to these types of compounds is shown in Scheme 9. The isomer mixture 34 was converted to the iodide 35 by reaction with methanesulfonyl chloride in $CH_2Cl_2$ in the presence of pyridine, followed by a displacement with sodium iodide in acetone. Reaction of 35 with triphenylphosphine in refluxing acetonitrile afforded the phosphonium salt. A Wittig reaction between the phosphonium salt and naphthaldehyde 18 produced diene 36 (as a mixture of double bond isomers). Reduction with $H_2$ over Pd/C followed by hydrolysis (2N HCl, MeOH) gave aniline 37. Aniline 37 was reacted with 9-chloroacridine in MeOH in the presence of triethylamine to give 38. Cleavage of the methyl ethers with boron tribromide gave quinone 39.

A third synthetic approach to a 1,2-naphthoquinone moiety bound to an aminoacridine intercalator is depicted in Scheme 10. Aminoacridine was protected with mesitylenesulfonyl chloride to give 41, which was then alkylated with 1,5-dibromopentane to 42. The latter is brought into reaction with the silver salt of 2-hydroxy-1,4-naphthoquinone and the quinone-acridine 43 was thus obtained. Cleavage of the amide group using samarium iodide gave 44, the expected compound.

Synthesis of 1,2-Naphthoquinol Phosphates

In order to obtain 1,2-naphthoquinone derivatives that behave as "pro-drugs" the synthesis of quinol phosphates that can be hydrolyzed by cell phosphatases to liberate the parent quinones was carried out. Scheme 11 outlines the synthesis of the quinol phosphates. The parent 1,2-naphthoquinone 46 was brought into reaction with dibenzylphosphite to give a mixture of the two possible regioisomers 47. By cleavage of the benzyl residues with hydrogen in the presence of 10% Pd on charcoal the mixture of the two possible quinol phosphates 48 was obtained. They were used as such in the biological studies.

Synthesis of 8-Hydroxy-β-Lapachone 55

Scheme 12 outlines the synthesis of 55, a phenol derivative of β-lapachone that could be used as a building block for the construction of peptide derivatives of β-lapachone. The synthesis starts with the commercially available ester 49, that is acetylated using a Friedel-Crafts reaction to give 50. Cyclization of 50 in the presence of base and air gave the p-quinone 51. Alkylation of 51 with dimethyl allyl bromide gave a mixture of the C-alkyl derivative 52 and the O-alkyl derivative 53. They were separated and on treatment of 52 with concentrated sulfuric acid, the 8-methoxy-β-lapachone 54 was obtained. Cleavage of the methoxy group with boron tribromide gave the expected α-naphthoquinone 55.

Synthesis of 1,2-Naphthoquinone Bisulfite Adducts

Bisulfite adducts of 1,2-naphthoquinones were prepared as "pro-drugs." They are stable in aqueous solutions at pH below 7 but liberate the quinone core at pH above 7. Since biological media are usually above pH 7, the bisulfite adducts led to a slow release of the quinones after administration in an aqueous medium. A list of selected bisulfite adducts is given in FIG. 1. General preparation procedures are given in Experimental.

Synthesis of 1,2-Naphthoquinone Peptides 1,2-Naphthoquinone conjugates of tetra and hexapeptides were prepared to obtain "prodrug" derivatives that can be cleaved by prostatic PSA. The guidelines followed for the synthesis of the peptides were based on the published results of Isaacs and coworkers (Denmeade et al. Cancer Res. 1997, 57, 4924), where they define the substrate specificity of PSA (prostate specific antigen). The synthesis of a quinone tetrapeptide is outlined in Scheme 13 for the 3-β-alanyloxy-β-lapachone (SL-11006) conjugate. SL-11006 (Quin) was coupled to Boc-Gln with DCC in the presence of 1-hydroxybenzotriazole to give Boc-Gln-Quin. Removal of the Boc group from Boc-Gln-Quin with TFA in $CH_2Cl_2$ gave TFA.Gln-Quin. Boc-Leu was coupled to TFA.Gln-Quin with DCC in the presence of 1-hydroxybenzotriazole to give Boc-Leu-Gln-Quin. Removal of the Boc group from Boc-Leu-Gln-Quin with TFA in $CH_2Cl_2$ gave TFA.Leu-Gln-Quin. Boc-Lys(Nε-Cbz) was coupled to TFA.Leu-Gln-Quin with DCC in the presence of 1-hydroxybenzotriazole to give Boc-Lys(Nε-Cl-Cbz)-Leu-Gln-Quin. Removal of the Boc group from Boc-Lys(Nε-Cbz)-Leu-Gln-Quin with TFA in $CHCl_3$ gave TFA.Lys(Nε-Cbz)-Leu-Gln-Quin. Morpholino-Ser(OBn) was coupled to TFA-Lys(Nε-Cbz)-Leu-Gln-Quin with DCC in the presence of 1-hydroxybenzotriazole to give morpholino-Ser(OBn)-Lys(Nε-Cbz)-Leu-Gln-Quin. The side chain protecting groups were removed by hydrogenolysis to yield morpholino-Ser-Lys-Leu-Gln-Quin. During the hydrogenolysis, the quinone was reduced to the hydroquinone, which reoxidized to the quinone on exposure to air.

Morpholino-Ser(OBn) was prepared from N-Fmoc-Ser (OBn). Esterification of N-Fmoc-Ser(OBn) with isobutylene in the presence of a catalytic amount of $H_2SO_4$ afforded N-Fmoc-Ser(OBn)-OtBu. The Fmoc group was removed with piperidine in $CH_2Cl_2$ to produce Ser(OBn)-OtBu. Reaction of Ser(OBn)-OtBu with 4-morpholinecarbonyl chloride in pyridine yielded morpholino-Ser(OBn)-OtBu. Morpholino-Ser(OBn)-OtBu was hydrolyzed with TFA in $CH_2Cl_2$ to yield morpholine-Ser(OBn).

The synthesis of a tetrapeptide conjugate of 3-leucyloxy-β-lapachone is outlined in Scheme 14.

Experimental tert-Butyl δ-[(1,2-dihydro-1,2-dioxonaphth-4-yl)oxy]valerate (1). A mixture of tert-butyl 5-bromovalerate (1 g, 4.2 mmol) and the silver salt of 2-hydroxy-1,4-naphthoquinone (0.8 g, 3.84 mmol) in benzene (10 mL), was stirred for 24 h at 50° C. The reaction mixture was filtered through celite and the solvent was removed in vacuo. The residue was purified by flash chromatography (5% methanol in chloroform) to give a yellow solid (384 mg, 30%). $^1H$ NMR ($CDCl_3$) 8.12 (d, J=7.7 Hz, 1H), 7.89 (d, J=7.7 Hz, 1H), 7.70 (t, J=6.1 Hz, 1H), 7.59 (t, J=6.4 Hz, 1H), 5.95 (s, 1H), 4.17 (t, J=5.9 Hz, 2H), 2.35 (t, J=7.2 Hz, 2H), 1.90-2.05 (m, 2H), 1.78-1.90 (m, 2H), 1.47 (s, 9H).

Benzyl 5-[(1,2-dihydro-1,2-dioxonaphth-4-yl)oxy]valerate (2). A mixture of benzyl 5-bromovalerate (2.27 g, 8.4 mmol) and the silver salt of 2-hydroxy-1,4-naphthoquinone (1.63 g, 5.81 mmol) in benzene (8 mL) was stirred for 48 h at 55° C. and filtered through celite. The filtrate was diluted with diethyl ether, extracted with a 20% aqueous solution of $NaHSO_3$ then basified to pH 10-11 with $Na_2CO_3$, and extracted with $CH_2Cl_2$. Yellow solid (1.334 g, 63%). $^1H$ NMR ($CDCl_3$) 8.12 (d, J=7.5 Hz, 1H), 7.85 (d, J=7.7 Hz, 1H), 7.68 (t, J=7.5 Hz, 1H), 7.58 (t, J=7.7 Hz, 1H), 7.25-7.50 (m, 5H), 5.93 (s, 1H), 5.14 (s, 2H), 4.15 (t, J=5.7 Hz, 2H), 2.50 (t, J=7.0 Hz, 2H), 1.8-2.2 (m, 4H).

5-[(1,2-Dioxo-1,2-dihydronaphth-4-yl)oxy]valeric Acid (3). Benzyl ester 2 (1.90 g, 5.22 mmol) was hydrogenated at 30 psi with Pd (400 mg) in ethyl acetate (120 mL) for 6 h. The catalyst was removed by filtration through celite, the solvent was evaporated in vacuo and the residue was oxidized with $Ag_2O$ (1.45 g, 6.25 mmol) in $Et_2O$ by stirring for 10 h. Following filtration and evaporation of the solvent the product was crystallized from benzene to afford 0.53 g of pure material. The mother liquor was purified by flash chromatography ($CH_2Cl_2$/MeOH 15:1), the product dissolved in $CH_2Cl_2$, extracted with aqueous $NaHCO_3$ solution, acidified to pH 1 with 3% HCl and extracted back with $CH_2Cl_2$ to give additional 0.25 g of pure material (total yield 55%), mp 134-136° C.; $^1H$ NMR ($CDCl_3$) 8.12 (d, J=7.0 Hz, 1H), 7.87 (d, J=7.6 Hz, 1H), 7.70 (t, J=7.5 Hz, 1H), 7.59 (t, J=7.4 Hz, 1H), 7.27 (s, 1H), 4.18 (t, J=5.9 Hz, 2H), 2.51 (t, J=7.0 Hz, 2H), 1.75-2.15 (m, 4H).

1,2-Dihydro-4-(6-hydroxyhexyloxy)-1,2-dioxo-naphthalene (4). A mixture of 6-bromohexanol-1 (4.5 g, 24.85 mmol) and the silver salt of 2-hydroxy-1,4-naphthoquinone (6.46 g, 23.01 mmol) in benzene (24 mL) was stirred for 48 h at 60° C. The reaction mixture was worked up as described for 2 and crystallized from hexane to afford a yellow solid (3.18 g, 50%). mp 96-98° C., $^1$H NMR (CDCl$_3$) 8.12 (d, J=7.5 Hz, 1H), 7.87 (d, J=7.7 Hz, 1H), 7.70 (t, J=7.5 Hz, 1H), 7.58 (t, J=7.5 Hz, 1H), 5.95 (s, 1H), 4.15 (t, J=6.3 Hz, 2H), 3.69 (t, J=6.2 Hz, 2H), 1.92-1.97 (m, 2H), 1.3-1.8 (m, 7H)

1,2-Dihydro-4-(6-iodohexyloxy)-1,2-dioxonaphthalene (5). A mixture of 1,6-diiodohexane (10.14 g, 30 mmol) and the silver salt of 2-hydroxy-1,4-naphthoquinone (2.81 g, 10 mmol) in benzene (60 mL) was stirred for 12 h at room temperature. The reaction mixture was filtered through Celite, concentrated in vacuo, and purified by flash chromatography (hexane/EtOAc 4:1) to give a yellow solid (2,19 g, 57%); mp 85-87° C.; $^1$H NMR (CDCl$_3$) 8.12 (dd, J=6.5, 1.0 Hz, 1H), 7.86 (dd, J=6.9, 0.9 Hz, 1H), 7.70 (dt, J=7.6, 1.5 Hz, 1H), 7.58 (dt, J=7.5, 1.3 Hz, 1H), 5.95 (s, 1H), 4.15 (t, J=6.3, 2H), 3.22 (t, J=6.9 Hz, 2H), 1.80-2.05 (m, 4H), 1.45-2.10 (m, 4H).

bis[6-[(1,2-Dihydro-1,2-dioxonaphth-4-yl)oxy]hexyl] carbonate (6). Pyridine (0.12 ml, 1.5 mmol) was added to a stirred solution of the alcohol 4 (200 mg, 0.73 mmol) and bis(trichloromethyl)carbonate (40 mg, 0.134 mmol) in CH$_2$Cl$_2$ (5 mL) at 0° C. The cooling bath was removed, the reaction mixture was diluted with CH$_2$Cl$_2$, washed with 3% HCl, brine, dried (Na$_2$SO$_4$) and purified by column chromatography (benzene/EtOAc 4:1, 2:1). The product was triturated with Et$_2$O to afford a yellow solid (127 mg, 30%), mp 78-82° C. (decomp.). MS (LSIMS, 3-NBA) 576 (M$^+$+2), 401, 175; $^1$H NMR (CDCl$_3$) 8.09 (dd, J=6.0, 1.6 Hz, 1H), 7.85 (dd, J=7.8, 1.2 Hz, 1H), 7.71 (t, J=6.9 Hz, 1H), 7.58 (t, J=6.2 Hz, 1H), 5.94 (s, 1H), 4.17 (t, J=6.0 Hz, 2H), 4.15 (t, J=5.6 Hz, 2H), 1.85-2.10 (m, 2H), 1.65-1.85 (m, 2H), 1.40-1.65 (m, 4H).

N-(1-Methyl-5-methyloxycarbonylpyrrol-3-yl)-5-[(1,2-dihydro-1,2-dioxonaphth-4-yl)oxy]valeramide (7). A solution of an acid 3 (334 mg, 1.22 mmol) in DMF (1.67 mL) was treated with HBTU (462 mg, 1.22 mmol) followed by DIEA (452 mg, 3.5 mmol) and stirred for 5 min. 3-Amino-1-methyl-5-methyloxycarbonylpyrrol hydrochloride (232 mg, 1.22 mmol) and DIEA (378 mg, 3 mmol) were added to the reaction mixture. The latter was stirred for 2 h, diluted with Et$_2$O, the precipitate was removed, dissolved in CHCl$_3$, washed with 3% HCl, H$_2$O, aqueous NaHCO$_3$, H$_2$O again, dried (MgSO$_4$) and purified by chromatography on alumina column (CHCl$_3$/MeOH 80:1, 50:1). The product was triturated with Et$_2$O/CHCl$_3$ to obtain a yellow-red solid (200 mg, 40%); mp 122-123° C. (decomp.): MS (LSIMS, 3-NBA) 410 (M$^+$), 237 (M$^+$−173). $^1$H NMR (CDCl$_3$) 8.08 (d, J=7.5 Hz, 1H), 7.86 (d, J=7.3 Hz, 1H), 7.68 (t, J=7.5 Hz, 1H), 7.57 (t, J=7.5 Hz, 1H), 7.38 (d, J=1.8 Hz, 1H), 7.34 (s, 1H), 6.65 (d, J=2 Hz, 1H), 5.95 (s, 1H), 4.19 (t, J=5.53 Hz, 2H), 3.88 (s, 3H), 3.80 (s, 3H), 2.46 (t, J=6.6 Hz, 2H), 1.90-2.15 (m, 4H).

4-(tert-Butylcarbonyloxy)-1,2-dihydro-1,2-dioxonaphthalene (8). A mixture of the silver salt of 2-hydroxy-1,4-naphthoquinone (842 mg, 3 mmol), and pivaloyl chloride (434 mg, 3.6 mmol) in benzene (5 mL) was stirred for 8 h at room temperature. The reaction mixture was filtered through Celite, the precipitate washed with EtOAc, and the combined organic solutions were concentrated in vacuo and purified by flash chromatography (EtOAc/hexane 1:10, 1:5). The product was recrystallized from hexane to afford a yellow solid (190 mg, 25%); mp 125-126° C.; $^1$H NMR (CDCl$_3$) 8.15 (dd, J=7.7, 1.1 Hz, 1H), 7.71 (dt, J=7.7, 1.5 Hz, 1H), 7.59 (dt, J=7.5, 1.2 Hz, 1H), 7.57 (dd, J=7.6, 1.1 Hz, 1H), 6.48 (s, 1H), 1.44 (s, 9H).

N-[3-(Dimethylamino)propyl][3-[[3-[[3-[4-[(1,2-dihydro-1,2-dioxonaphth-4-yl)oxy]butylcarbonylamino]-1-methylpyrrol-5-yl]carbonylamino]-1-methylpyrrol-5-yl]carbonylamino]-1-methylpyrrol-5-yl]carboxamide (10) was prepared from acid 3 (61 mg, 0.222 mmol) and Boc-protected pyrrolylamine 9 (84 mg, 0.148 mmol) using the procedure described for 7. After the reaction was completed, the reaction mixture was diluted with Et$_2$O, the precipitate was removed, triturated with hot EtOAc and crystallized from a CHCl$_3$/Et$_2$O mixture. The product was a yellow solid (30 mg, 28%); mp 159-162° C. (decomp.); $^1$H NMR (DMSO-d$_6$) 9.90 (s, 1H), 9.89 (s, 1H), 9.86 (s, 1H), 8.08 (bs, 1H), 7.97 (d, J=7.7 Hz, 1H), 7.87 (d, J=7.2 Hz, 1H), 7.81 (t, J=7.9 Hz, 1H), 7.68 (t, J=7.2 Hz, 1H), 7.24 (s, 1H), 7.19 (s, 1H), 7.04 (s, 1H), 6.89 (s, 1H), 6.84 (s, 1H), 6.06 (s, 1H), 4.25 (t, J=5.8 Hz, 2H), 3.85 (s, 3H), 3.84 (s, 3H), 3.80 (s, 3H), 3.12-3.30 (m, 2H), 2.25-2.45 (m, 4H), 2.19 (s, 6H), 1.72-2.00 (m, 4H), 1.60-1.70 (m, 2H).). MS (LSIMS, 3-NBA) 725.2 (M$^+$+1).

1,2-Dihydro-4-[6-[(4-cyanophenyl)oxy]hexyloxy]-1,2-dioxonaphthalene (11). A mixture of 4-hydroxybenzonitrile (87 mg, 0.73 mmol), naphthoquinone 4 (200 mg, 0.73 mmol), PPh$_3$ (191 mg, 0.73 mmol) in dioxane (10 mL) was cooled to 10° C. and treated with DEAD (140 mg, 0.80 mmol). The reaction mixture was stirred for 10 h, concentrated in vacuo and purified by chromatography (5% EtOAc in benzene) to afford 11 as a yellow solid (171 mg, 53%), $^1$H NMR (CDCl$_3$) 8.13 (dd, J=7.3, 1.4 Hz, 1H), 8.86 (dd, J=7.7, 1.1 Hz, 1H), 7.67 (dt, J=7.5, 1.5 Hz 1H), 7.60 (dt, J=7.5, 1.5 Hz, 1H), 7.57 (d, J=8.8 Hz, 2H), 6.93 (d, J=8.9 Hz, 2H), 5.96 (s, 1H), 4.17 (t, J=6.4 Hz, 2H), 4.03 (t, J=6.3 Hz, 2H), 1.80-2.05 (m, 4H), 1.58-1.68 (m, 4H).

1,2-Dihydro-4-[6-(phenyloxy)hexyloxy]-1,2-dioxonaphthalene (12). Phenol (28 mg, 0.3 mmol) was treated with tetrabutylammonium hydroxide (0.3 mL of 1.0 M solution in methanol) and the reaction mixture was concentrated to dryness in vacuo. Iodonaphthoquinone 5 (115 mg, 0.3 mmol) in DMF (3 mL) was added to the tetrabutylammonium salt, stirred for 48 h and quenched with H$_2$O (10 mL). The product was extracted with CHCl$_3$, the extract was washed with H$_2$O, then brine, dried (Na$_2$SO$_4$), and purified by chromatography (5% EtOAc in benzene) to give 12 as a yellow solid (45 mg, 43%) $^1$H NMR (CDCl$_3$) 8.13 (d, J=7.4 Hz, 1H), 7.86 (d, J=7.4 Hz, 1H), 7.67 (t, J=7.6 Hz, 1H), 7.61 (t, J=7.5 Hz, 1H), 7.15-7.40 (m, 2H), 6.85-7.10 (m, 3H), 5.96 (s, 1H), 4.17 (t, J=6.5 Hz, 2H), 3.99 (t, J=6.2 Hz), 1.70-2.10 (m, 4H), 1.35-1.70 (m, 4H).

3-Dimethylaminophenyl 5-[(1,2-dihydro-1,2-dioxonaphth-4-yl)oxy]valerate (13). A mixture of acid 3 (137 mg, 0.5 mmol), 3-dimethylaminophenol (82 mg, 0.6 mmol), DCC (103 mg, 0.5 mmol), and DMAP (12 mg, 0.01 mmol) in THF (2 mL) was stirred for 2 h. The reaction mixture was concentrated in vacuo, the residue dissolved in benzene, washed with H$_2$O and dried (Na$_2$SO$_4$). Column chromatography (10% EtOAc) in benzene gave 13 as a yellow solid (70 mg, 36%), $^1$H NMR (CDCl$_3$) 8.13, (d, J=7.3 Hz, 1H), 7.90 (d, J=7.4 Hz, 1H), 7.69 (t, J=6.1 Hz, 1H), 7.58 (t, J=7.6 Hz, 1H), 7.22 (dd, J=8.1, 8.1 Hz, 1H), 6.30-6.70 (m, 2H), 5.96 (s, 1H), 4.21 (t, J=5.6 Hz, 2H), 2.69 (t, J=6.5 Hz, 2H), 1.90-2.15 (m, 4H).

2'-[4-[6-(1,2-Dihydro-1,2-dioxo-naphth-4-yl)oxyhexyl]oxyphenyl]-5-(4-methylpiperazin-1-yl)-2,5'-bi-1H-benzimidazole (14). Hoechst 33258 (3.0 g, 5 mmol) was dissolved in a hot mixture of isopropanol-water (24 mL/12 mL) and neutralized with ammonium hydroxide (3 mL). The precipitate was filtered, triturated with Et$_2$O and dried in vacuo to obtain the free base of bisbenzimidazole. A 1.0 M solution of Bu$_4$NOH in MeOH (0.6 mL, 0.6 mmol) was added to the solution of bisbenzimidazole (1.635 g, 3.85 mmol) in MeOH (30 mL), stirred for 15 min and concentrated to dryness in vacuo. Iodonaphthoquinone 5 (1.485 g, 3.87 mmol) in DMF (30 mL) was added to the tetrabutyl ammonium salt and the mixture was stirred for 48 h. The reaction mixture was suspended in H$_2$O, the crude product was filtered, washed with H$_2$O, dried and purified by flash chromatography (MeOH/CHCl$_3$ 1:9, 1:5) to afford 14 as a yellow solid (790 mg, 30%). $^1$H NMR (CDCl$_3$/MeOH-d$_4$) 8.21 (s, 1H), 8.09 (d, J=7.6 Hz, 1H), 8.05 (d, J=8.7 Hz, 2H), 7.85-7.95 (m, 2H), 7.48-7.75 (m, 4H), 7.14 (bs, 1H), 7.10-6.98 (m 3H), 4.21 (t, J=6.3 Hz, 2H), 4.08 (t, J=6.2 Hz, 2H), 2.65-2.75 (m, 4H), 2.40 (s, 3H), 1.80-2.15 (m, 4H), 1.60-1.75 (m, 4H). MS (LSIMS, 3-NBA) 725.2 (M$^+$+1).

Trifluoroacetate of 6-[(1,2-dihydro-1,2-dioxonaphth-4-yl) oxy]hexyl 6-aminohexanoate (15). [6-(tert-Butyloxycarbonyl)amino]hexanoic acid (139 mg, 0.6 mmol) was added into solution of DCC (113 mg, 0.55 mmol) and DMAP (64 mg, 0.52 mmol) in CH$_2$Cl$_2$ (10 mL) at 0° C. and stirred for 15 min, when naphthoquinone 4 (137 mg, 0.5 mmol) was added. The reaction mixture was stirred for 12 h at room temperature, diluted with CH$_2$Cl$_2$, extracted 3 times with an aqueous solution of KHSO$_4$, then with a NaHCO$_3$ solution followed by brine, dried (MgSO$_4$), and finally it was concentrated to dryness in vacuo and triturated with Et$_2$O. The residue was dissolved in CH$_2$Cl$_2$ (3 mL), TFA (0.5 mL) was added to the solution and the mixture stirred at 0° C. for 1 h. All volatiles were removed in vacuo and the residue was triturated in Et$_2$O to give 15 (100 mg, 40%). as a dark yellow oil. $^1$H NMR (CDCl$_3$) 8.90 (d, J=7.6 Hz, 1H), 7.99 (bs, 3H), 7.87 (d, J=7.8 Hz, 1H), 7.71 (t, J=7.6 Hz, 1H), 7.59 (t, J=7.5 Hz, 1H), 5.96 (s, 1H), 4.17 (t, J=6.3 Hz, 2H), 4.09 (t, J=6.2 Hz, 2H), 2.90-3.15 (m, 2H), 2.29 (t, J=7.1 Hz, 2H), 1.90-2.10 (m, 2H), 1.30-1.85 (m, 12H).

1,2-Dihydro-1,2-dioxo-4-[4-[2-[3-[2-(Ethylaminocarbonyl)ethylaminocarbonyl]propyl=aminocarbonyl]ethylaminocarbonyl]butyloxy]naphthalene (17). Acid 3 (137 mg, 0.5 mmol) was dissolved in DMF (1 mL), treated with HBTU (190 mg, 0.5 mmol) followed by DIEA (260 μL, 1.5 mmol) and stirred for 10 min. N-Ethyl[2-[3-(2-aminoethylcarbonylamino)propylcarbonylamino]ethyl]carboxamide hydrochloride 16 (154 mg, 0.5 mmol) and DIEA (260 μL, 1.5 mmol) were added to the reaction mixture, the latter was stirred for 2 h, and the reaction mixture was diluted with Et$_2$O. The product was filtered and triturated with CHCl$_3$ to afford a yellow solid (100 mg, 38%), mp 145-170° C. (decomp.) $^1$H NMR (CDCl$_3$, MeOH-d$_4$) 8.10 (dd, J=7.6, 1.4 Hz, 1H), 7.92 (dd, J=7.8, 1.2 Hz, 1H), 7.72 (dt, J=7.7, 1.2 Hz, 1H), 7.62 (dt, 7.6, 1.3 Hz, 1H), 7.30-7.50 (m, 2H), 7.15 (bs, 1H), 5.97 (s, 1H), 4.20 (t, J=5.8 Hz, 2H), 3.35-3.50 (m, 4H), 3.10-3.30 (m, 4H), 3.32-3.42 (m, 4H), 2.30 (t, J=6.9 Hz, 2H), 2.19 (t, J=7.4 Hz, 2H), 1.75-2.05 (m, 4H), 1.78 (t, J=7.2, 2H), 1.13 (t, J=7.3, 3H). MS (FAB, NaI) 551.2 (M+Na), 529 (M$^+$+1).

3,4-Dimethoxy-1-naphthaldehyde (18). A mixture of 1,2-dimethoxynaphthalene (0.74 g, 4 mmol) and DMF (0.8 mL, 10 mmol) in dichlorobenzene (0.8 mL) was stirred with POCl$_3$ at 100° C. for 2 h. The reaction mixture was cooled to 0° C., quenched with a cold aqueous solution of NaOAc, diluted with H$_2$O and extracted with benzene. The extracts were dried (MgSO$_4$), concentrated in vacuo and dichlorobenzene was removed by kugelrohr distillation at 110° C./0.5 mm Hg. Column chromatography (20% EtOAc in hexane) gave the product 18 (596 mg, 68%), which was used in the following step without further purification. $^1$H NMR (CDCl$_3$) 10.42 (s, 1H), 9.00-9.15 (m, 1H), 8.15-8.30 (m, 1H), 7.61 (s, 1H), 7.50-7.65 (m, 2H), 4.12 (s, 3H), 4.07 (s, 3H).

4-Butylaminomethyl-1,2-dimethoxy-naphthalene (19). A suspension of PtO$_2$ (40 mg) in EtOH (2 mL) was stirred with H$_2$ at 25 psi for 30 min. Naphthaldehyde 18 (596 mg, 2.8 mmol) was dissolved in EtOH and added into the suspension followed by the addition of butylamine (219 mg, 3 mmol). The reaction mixture was hydrogenated for 6 h at 50 psi. The catalyst was filtered through Celite, washed with acetone and the filtrate was concentrated to dryness to give 19 as an oil (665 mg, 87%). The product was utilized in the following step without further purification. $^1$H NMR (CDCl$_3$) 8.16 (d, J=7.5 Hz, 1H), 7.99 (d, J=7.6 Hz, 2H), 7.40-7.60 (m, 2H), 7.35 (s, 1H), 4.19 (s, 2H), 4.00 (s, 3H), 3.98 (s, 3H), 2.76 (t, J=7.0 Hz, 2H), 1.64 (bs, 1H), 1.45-1.60 (m. 2H), 1.30-1.45 (m, 2H), 0.93 (t, J=7.2 Hz, 3H).

4-(N-Acetyl-N-butylaminomethyl)-1,2-dimethoxy-naphthalene (20). Triethylamine (350 μL, 2.5 mmol) was added to a solution of aminonaphthalene 19 (250 mg, 0.9 mmol) and AcCl (90 μL, 1.27 mmol) in CH$_2$Cl$_2$ (5 mL) at 0° C. The cooling bath was removed after 10 min, the reaction mixture was stirred for 1 h at room temperature, diluted fivefold with CH$_2$Cl$_2$, washed with an aqueous solution of NaHCO$_3$ followed by 3% HCl, brine and dried (MgSO$_4$). The crude product (315 mg, 100%) obtained after evaporation of the solvent was used in the following step without further purification. $^1$H NMR (CDCl$_3$) 8.19, 8.15 (2d, J=7.6, 8.4 Hz, 1H), 8.97, 7.80 (2d, J=7.9, 8.2 Hz, 1H), 7.35-7.58 (m, 2H), 7.16, 7.04 (2s, 1H), 5.05, 4.95 (2s, 2H), 4.01, 3.99 (2s, 3H), 3.99, 3.96 (2s, 3H), 3.47, 3.13 (2t, J=7.4, 7.8 Hz, 2H), 2.20, 2.09 (2s, 3H), 1.15-1.70 (m, 4H), 0.91, 0.87 (2t, J=7.2, 7.3 Hz, 3H).

4-(N-Butyl-N-trifluoroacetylaminomethyl)-1,2-dimethoxy-naphthalene (21). Naphthalene 19 (200 mg, 0.73 mmol) was acylated with trifluoroacetyl anhydride (210 mg, 1 mmol) in the presence of TEA (0.2 mL, 1.5 mmol) by raising the temperature during 3 h from −40° to 0° C. The reaction mixture was diluted with CH$_2$Cl$_2$, washed with aqueous NaHCO$_3$, 3% HCl, brine and finally dried (MgSO$_4$). The crude product (266 mg, 99%) was used in the following step without further purification. $^1$H NMR (CDCl$_3$) 8.17-8.25 (m, 1H), 7.82 (t, J=7.7 Hz, 1H), 7.40-7.55 (m, 2H), 7.16, 7.03 (2s, 1H), 5.11, 5.08 (2s, 2H), 4.01, 4.03 (2s, 3H), 3.98, 3.96 (2s, 3H), 3.40, 3.25 (2t, J=7.5, 7.4 Hz, 2H), 1.45-2.75 (m, 2H), 1.10-1.45 (m, 2H), 0.89 (t, J=7.4, 3H).

4-[N-Butyl-N-[3-(4-morpholinocarbonyl)ethylcarbonyl] aminomethyl]-1,2-dimethoxynaphthalene (22). 3-(N-Morpholinocarbonyl)propionic acid (139 mg, 0.74 mmol) in CH$_2$Cl$_2$ (5 mL) was heated to reflux with thionyl chloride (440 mg, 3.7 mmol) for 1 h and all volatiles were evaporated in vacuo. The residue was dissolved in anhydrous CH$_2$Cl$_2$ (3 mL), cooled to 0° C. and naphthalene 19 (100 mg, 0.37 mmol), followed by DMAP (45 mg, 0.37 mmol) and TEA (140 μL, 1 mmol) were added into the reaction mixture. After stirring for 1 h at room temperature the reaction was quenched with wet EtOAc (10 mL), washed with 3% HCl, aqueous NaHCO$_3$, brine, and dried (Na$_2$SO$_4$). Purification by chromatography (15% EtOAc in hexane) gave 22 (160 mg, 98%). The product was used directly in the next step. $^1$H NMR (CDCl$_3$) 8.19, 8.17 (2d, J=7.7, 7.8 Hz, 1H), 7.92, 7.85 (2d, J=8.2, 8.05 Hz, 1H), 7.38-7.56 (m, 4H), 7.25, 7.17 (2s, 1H), 5.05, 5.03 (2s, 2H), 4.03, 4.00 (2s, 3H), 3.99, 3.98 (2s, 3H), 3.25-3.82 (m, 14H), 1.15-1.82 (m, 4H), 0.88. 0.85 (2t, J=7.1, 6.7 Hz, 3H).

Demethylation of dimethoxynaphthalenes with boron tribromide. 4-(Butylamino=methylene)-1,4-dihydro-2-hydroxy-1-oxo-naphthalene (23). A solution of dimethoxynaphthalene 19 (30 mg, 0.11 mmol) in $CH_2Cl_2$ (2 mL) was treated with a 1M solution of $BBr_3$ in $CH_2Cl_2$ (1.1 mL) at −78° C. and stirred at this temperature for 2 h. The reaction mixture was placed in a freezer at −10° C. for 3 h, quenched with $Et_2O$ (1 mL) by stirring for 15 min at room temperature and neutralized with aqueous solution of $NaHCO_3$. The product was extracted with EtOAc, dried ($MgSO_4$), and the solvent was removed in vacuo. The residue was dissolved in $Et_2O$, stirred for 10 h in an open flask and purified by chromatography (5% MeOH in $CHCl_3$). Trituration with $Et_2O$ yielded the product 23 (8 mg, 30%). $^1H$ NMR ($CDCl_3$) 9.05 (bs, 1H), 8.31 (d, J=8.1 Hz, 1H), 7.65-7.85 (m, 1H), 7.05-7.65 (m, 3H), 3.20-3.60 (m, 2H), 1.50-1.85 (m. 2H), 2.25-1.50 (m, 2H), 0.80-1.10 (m, 3H). HRMS (EI) 243.1250. Calcd for $C_{15}H_{17}NO_2$ 243.1259.

4-(N-Acetyl-N-butylaminomethyl)-1,2-dihydro-1,2-dioxonaphthalene (24) was prepared from dimethoxynaphthalene 20 using the procedure described for 23. The product (60%) was purified by chromatography (1.5% MeOH in $CHCl_3$) followed by trituration with $Et_2O$. $^1H$ NMR ($CDCl_3$) 8.1 (dd, J=7.53, 1.2 Hz, 1H), 7.67 (dd, J=7.7, 1.1 Hz, 1H), 7.50-7.62 (m, 2H), 6.21 (s, 1H), 4.68 (s, 2H), 3.35 (t, J=8.0 Hz, 2H), 2.25 (s, 3H), 1.50-1.75 (m, 2H), 1.15-1.50 (m, 2H), 0.96 (t, J=5.8, 3H). HRMS (EI) 285.1383. Calcd for $C_{17}H_{19}NO_3$ 285.1365.

4-(N-Butylaminomethyl-N-trifluorocetyl)-1,2-dihydro-1,2-dioxonaphthalene (25) was obtained from dimethoxynaphthalene 21 using the procedure described for 23. The product (37%) was purified by chromatography (3% MeOH in $CHCl_3$) followed by trituration in $Et_2O$. $^1H$ NMR ($CDCl_3$) 8.29 (d, J=7.13 Hz, 1H), 7.40-7.85 (m, 3H), 6.19 (s, 1H), 4.73 (s, 2H), 3.35-3.70 (m, 2H), 1.50-1.80 (m, 2H), 1.35-1.80 (m, 2H), 0.96 (t, J=7.2 Hz, 3H). HRMS (EI) 339.1106. Calcd for $C_{17}H_{16}F_3NO_3$ 339.1082.

4-[[N-Butyl-N-(4-morpholino-4-oxobutyryl)amino]methyl]-1,2-dihydro-1,2-dioxonaphthalene (26) was obtained from dimethoxynaphthalene 22 using the procedure described for 23. The product (10%) was purified by chromatography (25%-40% EtOAc in hexane) followed by trituration in $Et_2O$. $^1H$ NMR ($CDCl_3$) 8.19 (d, J=7.4 Hz, 1H), 7.70 (t, J=6.4 Hz, 1H), 7.59 (d, J=6.5 Hz, 1H), 7.50 (t, J=7.9 Hz, 1H), 6.33 (s, 1H), 4.65 (s, 2H), 3.35-3.80 (m, 14H), 1.65-1.85 (m, 2H), 1.25-1.50 (m, 2H), 0.96 (t, J=7.2 Hz, 3H).

meso-Tetra[4-[6-[(1,2-dihydro-1,2-dioxonaphth-4-yl)oxy]hexyloxy]phenyl]porphine (27). A 1 M solution of $Bu_4NOH$ in MeOH (0.212 mL,) was added to a stirred solution of meso-tetra(4-hydroxyphenyl)porphine (36 mg, 0.53 mmol) in MeOH (5 mL), stirring was kept for 10 min and the mixture concentrated to dryness in vacuo. Naphthoquinone 5 (81 mg, 0.21 mmol) in DMF (2 mL) was added to the porphyrin, the solution stirred for 48 h and diluted with $H_2O$ (20 mL). The product was extracted with $CHCl_3$, washed with brine, the solvent was evaporated and the residue was triturated with $Et_2O$. Purification by flash chromatography (2-3% MeOH in $CHCl_3$) followed by recrystallization from $CHCl_3/Et_2O$ (1:3) afforded the product as a dark red solid (19.6 mg, 21%). $^1H$ NMR ($CDCl_3$) 8.86 (s, 8H), 8.01-8.15 (m, 12H), 7.9 (d, J=7.8 Hz, 4H), 7.68 (t, J=6.3 Hz, 4H), 7.55 (t, J=7.5 Hz, 4H), 7.27 (d, J=7.8 Hz, 8H), 5.98 (s, 4H), 4.15-4.30 (m, 16H), 1.80-2.10 (m, 16H), 1.65-1.80 (m, 16H). Anal. Calcd for $C_{108}H_{94}N_4O_{16}$× 1.5$H_2O$: C, 74.87; H, 5.43; N, 3.23. Found: C, 74.62; H, 5.57; N, 3.11.

meso-Tetra [4-[6-[(1,2-dihydro-1,2-dioxanaphth-4-yl)oxyhexyl]oxycarbonyl]phenyl]porphyrin (28). EDCI (518 mg, 2.7 mmol) was added at 0° C. to a mixture of meso-tetra(4-carboxyphenyl)porphyrin (500 mg, 0.63 mmol), alcohol 4 (831 mg, 3 mmol), and DMAP (159 mg, 1.3 mmol) in $CH_2Cl_2$ (10 mL). The solution was stirred for 2 h, the cooling bath was removed and the reaction mixture was left at room temperature overnight. It was diluted with $CH_2Cl_2$, washed with 2% HCl, $H_2O$, aqueous solution of $NaHCO_3$, $H_2O$, 5% aqueous solution of $NaHSO_3$, $H_2O$, dried ($Na_2SO_4$) and concentrated in vacuo. The analytical sample was prepared by column chromatography on silica (2% MeOH in $CHCl_3$). Mp 98-110° C. (decomp.) Yield 572 mg, 50%. $^1H$ NMR ($CDCl_3$) 8.81 (s, 8H,), 8.45 (d, J=8.2 Hz, 8H), 8.30 (d, J=8.0 Hz, 8H), 8.09 (d, J=6.9 Hz, 4H), 7.89 (d, J=7.3 Hz, 4H), 7.70 (t, J=7.1 Hz, 4H), 7.56 (t, J=7.1 Hz, 4H), 5.98 (s, 4H), 4.56 (t, J=6.5 Hz, 8H), 4.21 (t, J=6.1 Hz, 8H), 1.85-2.20 (m, 16H), 1.60-1.80 (m, 16H). MS (MALDI) 1838 ($M^+$+23), 1817 ($M^+$+1). Anal. Calcd for $C_{112}H_{94}N_4O_{20}$× 4$H_2O$: C, 71.18; H, 5.40; N, 2.97. Found: C, 71.27; H, 5.24; N, 3.03.

N-Acetyl-4-(7-hydroxy-1-heptenyl)-aniline (29). A solution of 5.213 g (28.8 mmol) of 6-bromohexanol and 7.55 g (28.8 mmol) of triphenylphosphine in 50 mL of $CH_3CN$ was refluxed for 24 hr. Evaporation of solvent yielded the crude phosphonium salt, which was used directly in the next reaction. The crude phosphonium salt and 4.690 g (28.7 mmol) of 4-acetamidobenzaldehyde were dissolved in a mixture of 150 mL of $CH_2Cl_2$ and 150 mL of THF. To the cooled solution was added 1.529 g (60.5 mmol) of 95% NaH as a slurry in $CH_2Cl_2$ (10 mL). The reaction mixture was stirred in an ice bath for 1 hr, then at room temperature for 19 hr. The mixture was partitioned between 350 mL $CH_2Cl_2$ and 500 mL 1N HCl. The aqueous phase was extracted with $CH_2Cl_2$ (4×100 mL). The $CH_2Cl_2$ extracts were combined, dried with $MgSO_4$, and evaporated to dryness. Column chromatography on silica gel eluting first with 1% MeOH in $CH_2Cl_2$ and then with 2% MeOH in $CH_2Cl_2$ afforded 4.913 g (69% from 6-bromohexanol) of alkene 29 as a mixture of E and Z isomers: $^1H$ NMR (250 MHz, $CDCl_3$, TMS) δ 7.5-7.4 (m, 4H), 7.3-7.1 (m, 4H), 6.4-6.3 (m, 2H), 6.2-6.1 (m, 1H), 5.7-5.6 (m, 2H), 3.65 (t, J=6.5 Hz, 2H), 3.63 (t, J=6.5 Hz, 2H), 2.4-2.1 (m, 4H), 2.18 (s, 3H), 2.17 (s, 3H), 1.7-1.3 (m, 12H).

4-(7-Hydroxyheptyl)-aniline (30). To a solution of 4.913 g (19.9 mmol) of N-acetyl-4-(7-hydroxy-1-heptenyl)-aniline 29 in 100 mL of 10% MeOH in $CH_2Cl_2$ in a Parr bottle were added 490 mg of 10% Pd/C. The bottle was placed on a hydrogenation apparatus and shaken for 4 hr at 25 psi of hydrogen. Removal of catalyst by filtration through a celite pad and evaporation of solvent afforded 5.294 g of alkane: $^1H$ NMR (300 MHz, $CDCl_3$, TMS) δ 7.80 (s, NH), 7.38 (d, J=8 Hz, 2H), 7.09 (d, J=8 Hz, 2H), 3.61 (t, J=6.6 Hz, 2H), 2.54 (t, J=7.6 Hz, 2H), 2.12 (s, 3H), 1.6-1.5 (m, 4H), 1.4-1.3 (m, 6H).

A solution of the alkane in 40 mL of MeOH was mixed with 190 mL of 2N HCl. The reaction mixture was refluxed for 23 hr. Then the reaction mixture was added to a cooled mixture of 190 mL 2N NaOH and 200 mL $CH_2Cl_2$. The aqueous phase was extracted with $CH_2Cl_2$ (4×100 mL). The $CH_2Cl_2$ extracts were combined, dried with $MgSO_4$, and evaporated to dryness, to afford 3.579 g of aniline 30 (87% from alkene): $^1H$ NMR (300 MHz, $CDCl_3$, TMS) δ 6.95 (d, J=8.3 Hz, 2H), 6.61 (d, J=8.3 Hz, 2H), 3.60 (t, J=6.6 Hz, 2H), 2.48 (t, J=7.6 Hz, 2H), 1.6-1.5 (m, 4H), 1.4-1.3 (m, 6H).

N-(9-Acridinyl)-4-(7-hydroxyheptyl)-aniline (31). To a solution of 636.9 mg (3.07 mmol) of 4-(7-hydroxyheptyl)-aniline 30 and 428 µL (3.07 mmol) of Et$_3$N in 20 mL of MeOH were added 656.4 mg (3.07 mmol) of 9-chloroacridine. After stirring for 7 hr at room temperature, the solvent was evaporated. Purification by column chromatography on silica gel with 5% MeOH in CH$_2$Cl$_2$ gave 1.079 g (91%) of N-(9-acridinyl)-4-(7-hydroxyheptyl)-aniline 31: $^1$H NMR (300 MHz, CDCl$_3$, TMS) δ 8.0-7.9 (m, 4H), 7.63 (t, J=7 Hz, 2H), 7.3-7.2 (m, 2H), 7.07 (d, J=8.3 Hz, 2H), 6.85 (d, J=8.3 Hz, 2H), 3.64 (t, J=6.6 Hz, 2H), 2.57 (t, J=7.6 Hz, 2H), 1.7-1.5 (m, 4H), 1.4-1.3 (m, 6H).

N-(9-acridinyl)-4-(7-iodoheptyl)-aniline (32). To a solution of 604.1 mg (1.57 mmol) of N-(9-acridinyl)-4-(7-hydroxyheptyl)-aniline 31 in 20 mL of pyridine cooled to 0° C. was added 200 µL (2.58 mmol) of methanesulfonyl chloride. The reaction mixture was stirred at 0° C. for 1 hr 20 min, then partitioned between 180 mL of CH$_2$Cl$_2$ and 75 mL of water. The aqueous phase was extracted with CH$_2$Cl$_2$ (3×30 mL). The CH$_2$Cl$_2$ extracts were combined, washed with 40 mL of saturated NaCl solution, dried with MgSO$_4$, and evaporated to dryness.

The sulfonate was dissolved in 20 mL of acetone. To the solution was added 355.0 mg (2.37 mmol) of NaI, and the mixture was refluxed for 8 hr, then stirred at room temperature for 16 hr. The reaction mixture was partitioned between 200 mL of ethyl acetate and 100 mL of water. The organic phase was washed with 5% sodium thiosulfate (3×30 mL). All aqueous phases were combined and backextracted with 75 mL of ethyl acetate. Both ethyl acetate phases were combined, dried with MgSO$_4$, and evaporated to dryness, to afford 600.2 mg (77%) of N-(9-acridinyl)-4-(7-iodoheptyl)-aniline 32: $^1$H NMR (300 MHz, CDCl$_3$, TMS) δ 8.0-7.9 (m, 4H), 7.66 (t, J=7 Hz, 2H), 7.3-7.2 (m, 2H), 7.06 (d, J=8 Hz, 2H), 6.81 (d, J=8 Hz, 2H), 3.18 (t, J=7 Hz, 2H), 2.57 (t, J=7.6 Hz, 2H), 1.9-1.8 (m, 2H), 1.7-1.7 (m, 2H), 1.4-1.3 (m, 6H).

Quinone-anilinoacridine (33) (SL-11064). To a solution of 1.554 g (3.14 mmol) of N-(9-acridinyl)-4-(7-iodoheptyl)-aniline 32 in a mixture of 40 mL of CHCl$_3$ and 2 mL of MeOH was added 1.765 g (6.28 mmol) of silver salt. The reaction mixture was refluxed for 23 hr. The reaction mixture was diluted with CH$_2$Cl$_2$, filtered, and evaporated to dryness. Purification and separation of the para- and ortho-quinone isomers were accomplished using a series of columns on silica gel using 5% MeOH in CH$_2$Cl$_2$, Et$_2$O, and 10% MeOH in CH$_2$Cl$_2$. Isolated 108.9 mg of 33 as a dark orange solid.

N-Acetyl-4-(7-methanesulfonyl-1-heptenyl)-aniline. To a cooled solution of 500 mg (2.02 mmol) of N-acetyl-4-(7-hydroxy-1-heptenyl)-aniline 29 and 0.5 mL (6.18 mmol) of pyridine in 10 mL of CH$_2$Cl$_2$ was added 240 µL (3.10 mmol) of methane-sulfonyl chloride. The reaction mixture was stirred at room temperature for 22 hr. The reaction mixture was diluted with CH$_2$Cl$_2$, washed with 1N HCl (4×50 mL), washed with saturated NaCl solution (50 mL), dried with MgSO$_4$, and evaporated to dryness. Column chromatography on silica gel with 5% MeOH in CH$_2$Cl$_2$ afforded 416.1 mg (63%) of mesylate (mixture of E and Z isomers): $^1$H NMR (250 MHz, CDCl$_3$, TMS) δ 7.47 (d, J=8 Hz), 7.43 (d, J=8 Hz), 7.29 (d, J=8 Hz), 7.22 (d, J=8 Hz), 6.4-6.3 (m), 6.2-6.0 (m), 5.7-5.6 (m), 4.23 (t, J=6.6 Hz), 4.22 (t, J=6.6 Hz), 2.4-2.3 (m), 2.3-2.1 (m), 2.18 (s), 2.17 (s), 1.9-1.7 (m), 1.6-1.4 (m).

N-Acetyl-4-(7-iodo-1-heptenyl)-aniline (34). To a solution of 2.641 g (8.11 mmol) of N-acetyl-4-(7-methanesulfonyl-1-heptenyl)-aniline in 60 mL of acetone was added 1.832 g (12.2 mmol) of NaI. The reaction mixture was refluxed for 19 hr. Then, filtration and evaporation of solvent gave 3.410 g (quant) of iodide 34, which was used as is in the next reaction.

Phosphonium iodide (35). A solution of 3.410 g of N-acetyl-4-(7-iodo-1-heptenyl)-aniline 34 and 2.143 g (8.17 mmol) of triphenylphosphine in 70 mL of CH$_3$CN was refluxed for 43 hr. Evaporation of solvent and column chromatography on silica gel with 5% MeOH in CH$_2$Cl$_2$ yielded 4.781 g (95% from mesylate) of phosphonium iodide 35.

1-(3,4-Dimethoxy-1-naphthyl)-8-(4-acetamidophenyl)-1,7-octadiene (36). To a cooled solution of 3.17 g (5.12 mmol) of phosphonium iodide 35 and 1.093 g (5.05 mmol) of 3,4-dimethoxy-1-naphthaldehyde 18 in 20 mL of THF and 25 mL of CH$_2$Cl$_2$ was added 130 mg (5.14 mmol) of 95% NaH. The reaction mixture was stirred at room temperature for 21 hr. The mixture was partitioned between 200 mL 1N HCl and 350 mL CH$_2$Cl$_2$. The aqueous phase was extracted with CH$_2$Cl$_2$ (6×75 mL). The CH$_2$Cl$_2$ extracts were combined, dried with MgSO$_4$, and evaporated to dryness. Column chromatography on silica gel with 1% MeOH in CH$_2$Cl$_2$ afforded 1.073 g (49%) of diene 36.

1-(3,4-Dimethoxy-1-naphthyl)-8-(4-acetamidophenyl)-octane. To a solution of 556.3 mg (1.29 mmol) of 1-(3,4-dimethoxy-1-naphthyl)-8-(4-acetamidophenyl)-1,7-octadiene 36 in 20 mL of CH$_2$Cl$_2$ in a Parr bottle were added 55.4 mg of 10% Pd/C. The bottle was placed on a hydrogenation apparatus and shaken for 2.5 hr at 32 psi of hydrogen. Removal of catalyst by filtration through a celite pad and evaporation of solvent afforded 554.6 mg (99%) of octane: $^1$H NMR (250 MHz, CDCl$_3$, TMS) δ 8.14 (d, J=8 Hz, 1H), 7.94 (d, J=8 Hz, 1H), 7.5-7.4 (m, 1H), 7.4-7.3 (m, 3H), 7.12 (s 1H), 7.11 (d, J=8.2 Hz, 2H), 3.99 (s, 3H), 3.98 (s, 3H), 3.0-2.9 (m, 2H), 2.6-2.5 (m, 2H), 2.16 (s, 3H), 1.8-1.3 (m 12H).

1-(3,4-Dimethoxy-1-naphthyl)-8-(4-aminophenyl)-octane (37). A solution of 554.6 mg (1.28 mmol) of 1-(3,4-dimethoxy-1-naphthyl)-8-(4-acetamidophenyl)-octane in 20 mL of MeOH was mixed with 21 mL of 2N HCl. The reaction mixture was refluxed for 23 hr. Then the reaction mixture was partitioned between 75 mL of CH$_2$Cl$_2$ and 21 mL of 2N NaOH. The aqueous phase was extracted with CH$_2$Cl$_2$ (5×40 mL). The CH$_2$Cl$_2$ extracts were combined, dried with MgSO$_4$, and evaporated to dryness. Column chromatography on silica gel with 1% MeOH in CH$_2$Cl$_2$ gave 374.6 mg (75%) of aniline 37: $^1$H NMR (250 MHz, CDCl$_3$, TMS) δ 8.14 (d, J=8 Hz, 1H), 7.94 (d, J=8 Hz, 1H), 7.47 (t, J=8 Hz, 1H), 7.37 (t, J=8 Hz, 1H), 7.12 (s, 1H), 6.96 (d, J=8 Hz, 2H), 6.62 (d, J=8 Hz, 2H), 3.99 (s, 3H), 3.97 (s, 3H), 3.1-3.0 (m, 2H), 2.5-2.4 (m, 2H), 1.8-1.3 (m 12H).

Naphthylacridine (38). To a solution of 99 mg (2.53×10$^{-4}$ mol) of 1-(3,4-dimethoxy-1-naphthyl)-8-(4-aminophenyl)-octane 37 and 35 mL (2.51×10$^{-4}$ mol) of Et$_3$N in 4 mL of MeOH were added 54 mg (2.53×10$^{-4}$ mol) of 9-chloroacridine. The reaction mixture was stirred at room temperature for 20 hr. Evaporation of solvent and column chromatography on silica gel with first 1% MeOH in CH$_2$Cl$_2$ and then 3% MeOH in CH$_2$Cl$_2$ afforded 118.2 mg (82%) of acridine 38: $^1$H NMR (250 MHz, CDCl$_3$, TMS) δ 8.14 (d, J=8 Hz, 1H), 8.0-7.9 (m, 5H), 7.66 (br t, 2H), 7.46 (t, J=8 Hz, 1H), 7.37 (t, J=8 Hz, 1H), 7.3-7.2 (m, 2H), 7.12 (s, 1H), 7.06 (d, J=8.4 Hz, 2H), 6.82 (d, J=8.4 Hz, 2H), 3.1-3.0 (m, 2H), 2.6-2.5 (m, 2H), 1.8-1.3 (m, 12H).

Quinone-acridine (39) (SL-11125). To a solution of 546 mg (9.60×10$^{-4}$ mol) of acridine 38 in 15 mL of CH$_2$Cl$_2$ cooled to −68° C. was added 9.6 mL of 1M BBr$_3$ in CH$_2$Cl$_2$.

After –18.5 hr at –10° C., the reaction mixture was cooled to 68° C. and 10 mL of Et$_2$O were added. After stirring at room temperature for 30 min, 20 mL of saturated NaHCO$_3$ solution were added. The resulting precipitate was collected by filtration and triturated twice with 50 mL of CH$_2$Cl$_2$ to give 555.9 mg of quinone 39: $^1$H NMR (250 MHz, DMSO-d$_6$, TMS) δ 9.11 (s), 8.59 (s), 8.14 (d, J=9 Hz), 8.0-7.9 (m), 7.82 (d, J=8 Hz), 7.4-7.2 (m), 6.98 (s), 2.87 (t, J=7 Hz), 2.65 (t, J=7 Hz), 1.7-1.5 (m), 1.4-1.3 (m).

N-(9-acridyl)-mesitylenesulfonamide (41). To a suspension of 4.00 g (20.6 mmol) of 9-aminoacridine 40 in 350 mL of CHCl$_3$ was added 2.9 mL (20.8 mmol) of Et$_3$N and 4.50 g (20.6 mmol) of mesitylenesulfonyl chloride. The reaction mixture was refluxed for 72 hr. Then the reaction mixture was filtered and the solvent was evaporated. The material was purified by column chromatography on silica gel by eluting first with 1% MeOH in CH$_2$Cl$_2$ and then with 5% MeOH in CH$_2$Cl$_2$ to yield 458.4 mg (6%) of sulfonamide 41 as an orange solid: $^1$H NMR (300 MHz, CDCl$_3$, TMS) δ 9.25 (s, 1H), 8.77 (d, J=8 Hz, 2H), 7.46 (t, J=8 Hz, 2H), 7.21 (d, J=8 Hz, 2H), 7.15 (t, J=8 Hz, 2H), 7.02 (s, 2H), 2.78 (s, 6H), 2.36 (s, 3H).

N-(9-acridyl)-N-(5-bromopentyl)-mesitylenesulfonamide (42). A solution of 450 mg (1.20 mmol) of N-(9-acridyl)-mesitylenesulfonamide in 20 mL of DMF was placed under an atmosphere of argon and cooled to 0° C. To the cooled solution was added 36 mg (1.42 mmol) of NaH (95%). The reaction mixture was stirred at 0° C. for 5 min and at room temperature for 1 hr. Then the reaction mixture was cooled to 0° C., and 1.65 mL (12.1 mmol) of 1,5-dibromopentane were added. The reaction mixture was stirred at 70-80° C. for 23 hr. The reaction mixture was cooled, and quenched with 20 mL of water. The mixture was partitioned between CH$_2$Cl$_2$ and water. The aqueous phase was washed with CH$_2$Cl$_2$ (2×20 mL). The CH$_2$Cl$_2$ washes were combined with the organic phase, dried with MgSO$_4$, and evaporated to dryness. The material was purified by column chromatography on silica gel with CH$_2$Cl$_2$ to afford 382.2 mg (60%) of bromide 42 as an orange oil: $^1$H NMR (300 MHz, CDCl$_3$, TMS) δ 8.25 (d, J=9 Hz, 2H), 7.94 (d, J=9 Hz, 2H), 7.76 (t, J=8 Hz, 2H), 7.45 (t, J=8 Hz, 2H), 6.87 (s, 2H), 4.0-3.9 (m, 2H), 3.27 (t, J=6.5 Hz, 2H), 2.30 (s, 3H), 2.22 (s, 6H), 1.8-1.6 (m, 4H), 1.4-1.3 (m, 2H).

Mesityl-acridine-quinone (43). To a solution of 632.6 mg (1.20 mmol) of N-(9-acridyl)-N-(5-bromopentyl)-mesitylenesulfonamide 42 in 15 mL of benzene was added 338.4 mg (1.20 mmol) of silver salt. The reaction mixture was refluxed for 24 hr. The reaction mixture was diluted with CH$_2$Cl$_2$ and filtered to remove insoluble salts. The solvent was removed and the material was purified by column chromatography on silica gel with Et$_2$O to afford 333.1 mg (45%) of ortho-quinone 43 as an orange glassy solid: $^1$H NMR (300 MHz, CDCl$_3$, TMS) δ 8.24 (d, J=9 Hz, 2H), 8.11 (d, J=8 Hz, 1H), 7.95 (d, J=9 Hz, 2H), 7.8-7.7 (m, 3H), 7.7-7.5 (m, 2H), 7.5-7.4 (m, 2H), 6.86 (s, 2H), 5.85 (s, 1H), 4.1-4.0 (m, 4H), 2.29 (s, 3H), 2.21 (s, 6H), 1.9-1.5 (m, 4H), 1.5-1.4 (m, 2H).

Acridine-quinone (44) (SL-11059). Under an atmosphere of argon, 151.4 mg (2.45×10$^{-4}$ mol) of mesityl-acridine-quinone 43 was dissolved in 30 mL of 0.1M SmI$_2$ in THF. Then, 2.2 mL (18.2 mmol) of DMPU were added dropwise. The reaction mixture was refluxed for 24 hr. Filtration to remove a precipitate and evaporation of solvent yielded an orange oil, which was purified by column chromatography on silica gel with 5% MeOH in CH$_2$Cl$_2$ to afford 48.7 mg (45%) of acridine-quinone 44 as an orange glassy solid: $^1$H NMR (300 MHz, DMSO-d$_6$, TMS) δ 8.54 (d, J=8 Hz, 2H), 7.96 (t, J=7 Hz, 2H), 7.92 (d, J=7 Hz, 1H), 7.79 (d, J=8 Hz, 2H), 7.7-7.6 (m, 3H), 7.51 (t, J=8 Hz, 2H), 6.01 (s, 1H), 4.20 (t, J=6 Hz, 2H), 4.13 (t, J=7 Hz, 2H), 2.1-1.9 (m, 4H), 1.7-1.6 (m, 2H).

Synthesis of Quinol Phosphates: General Procedure

To a solution of 500 mg (2.05 mmol) of 4-pentyloxy-1,2-naphthoquinone 46 in 10 mL of benzene was added 2.3 mL (25.1 mmol) of dibenzylphosphite. The reaction mixture was refluxed under nitrogen for 2.5 hr, after which the benzene was removed. Column chromatography of the residue on silica gel with 1% MeOH in CH$_2$Cl$_2$ afforded 729.3 mg (70%) of aryldibenzylphosphate 47 (mixture of two regioisomers) as an orange oil: R$_f$=0.51, 0.66 (1% MeOH in CH$_2$Cl$_2$); $^1$H NMR (250 MHz, CDCl$_3$, TMS) major regioisomer δ 8.1 (d), 8.0 (br, s), 7.8 (d), 7.4 (t), 7.3-7.1 (m), 6.50 (s), 5.3-5.0 (AB of ABX, δ$_A$=5.16, δ$_B$=5.08, J$_{AB}$=11.5 Hz, J$_{AX}$=8.3 Hz, J$_{BX}$=8.8 Hz), 4.01 (t, J=6 Hz), 2.0-1.8 (m), 1.6-1.3 (m), 0.96 (t, J=7 Hz); $^{13}$C NMR (52 MHz, CDCl$_3$, TMS) both regioisomers δ 153.4, 144.7, 135.6 (d, J=6.1 Hz, minor regioisomer), 134.8 (d, J=5.5 Hz, major regioisomer), 128.7-127.7 (m), 127.2, 123.0, 122.2, 121.4, 119.8, 99.5, 71.0 (q, J=4.8 Hz), 68.3, 28.8, 22.5.

To a solution of 1.637 g (3.23 mmol) of aryldibenzylphosphate 47 in 40 mL of MeOH was added 150 mg of 10% Pd/C. The reaction mixture was placed under an atmosphere of hydrogen (balloon) and stirred at room temperature for 1 hr. Removal of catalyst by filtration and evaporation of solvent afforded phosphate as a brown oil. The phosphate was dissolved in 6 mL of benzene. Addition of 9 mL of hexane and cooling gave a precipitate. The precipitate was collected by filtration, washed with benzene/hexane=2:3, and dried, affording 797.3 mg (76%) of arylphosphate 48 as a gray solid; R$_f$=0.77 (MeOH); $^1$H NMR (250 MHz, acetone-d$_6$, TMS) δ 8.13 (d, J=8 Hz, 1H), 7.96 (d, J=8 Hz, 1H), 7.49 (t, J=7 Hz, 1H), 7.32 (t, J=7 Hz, 1H), 6.59 (s, 1H), 4.13 (t, J=6 Hz, 1H), 2.0-1.8 (m, 2H), 1.6-1.3 (m, 4H), 0.96 (t, J=7 Hz, 3H); $^{13}$C NMR (52 MHz, acetone-d$_6$, TMS) δ 153.3 (d, J=1.3 Hz), 145.8 (narrow t), 129.3 (d, J=3.3 Hz), 127.4, 123.2, 122.2, 121.6, 120.9, 100.0, 68.7, 29.2, 28.7, 22.7, 13.9.

Ethyl 2'-acetyl-5'-methoxyphenylacetate (50) Acetyl chloride (21.3 mL, 300 mmol) was added to a mixture of AlCl$_3$ (26.7 g, 200 mmol) and ethyl 3'-methoxyphenylacetate (49, 28.66 g, 147.6 mmol) in CS$_2$ (200 mL) at 0° C. The ice bath was removed and the mixture was allowed to warm to 20° C. with HCl gas bubbling out. After stirring at 20° C. for 30 min, the mixture was refluxed for 30 min. Upon cooling down, the mixture was added ice (200 g) and aqueous 2 N HCl (400 mL). The resulting mixture was extracted with ethyl acetate (2×200 mL). The extracts were washed with water (2×100 mL), dried over MgSO$_4$ and concentrated in vacuo. The residue was crystallized from a mixture of ethyl acetate (20 mL) and hexanes (60 mL) to afford 50 (30.60 g, 88%): $^1$H NMR (CDCl$_3$) δ 7.84 (1H, d, J=8.6 Hz), 6.86 (1H, dd, J=8.6, 2.6 Hz), 6.75 (1H, d, J=2.6 Hz), 4.17 (2H, q, J=7.1 Hz), 3.92 (2H, s), 3.86 (3H, s), 2.55 (3H, s), 1.28 (3H, t, J=7.1 Hz); $^{13}$C NMR (CDCl$_3$) δ 199.04 (s), 171.44 (s), 162.22 (s), 137.70 (s), 132.97 (d), 129.48 (s), 118.68 (d), 111.84 (d), 60.60 (t), 55.39 (q), 41.17 (t), 28.39 (q), 14.24 (q).

2-Hydroxy-7-methoxy-1,4-naphthoquinone (51). Sodium ethoxide (10.40 g, 150 mmol) was added to a suspension of 50 (30.45 g, 128.90 mmol) in absolute alcohol (200 mL) at 20° C. After stirring the mixture for 1 h, air was bubbled in for 20 h. The mixture was concentrated in vacuo. The residue was dissolved in water (500 mL), and extracted with diethyl ether (200 mL). The ether layer was counter-extracted with water (50 mL). The combined aqueous phase was acidified with concentrated HCl (30 mL). The mixture was filtered to afford 51 (14.42 g, 55%): $^1$H NMR (DMSO-d$_6$) δ 11.56 (1H, s, br), 7.89 (1H, d, J=8.5 Hz), 7.42 (1H, d, J=2.8 Hz), 7.36 (1H, dd, J=8.5, 2.8 Hz), 6.10 (1H, s), 3.92 (3H, s); $^{13}$C NMR (DMSO-d$_6$) 6.184.07 (s), 181.20 (s), 162.92 (s), 159.16 (s), 132.35 (s), 127.82 (d), 125.16 (s), 120.02 (d), 110.85 (s), 109.94 (d), 55.90 (q).

7-Methoxy-lapachol (52). A mixture of K$_2$CO$_3$ (30 mmol) and 51 (10.21 g, 50 mmol) in HMPA (100 mL) was stirred for 30 min, when it became a suspension. Dimethylallyl bromide (8.7 mL, 75 mmol) and KI (4.15 g, 25 mmol) were added, and stirring was continued for 20 h at 20° C. The mixture was diluted with ice water (600 mL) and concentrated HCl (30 mL), and extracted with ethyl acetate (2×200 mL). Some solid was collected by filtration to afford the first portion of 53 (0.628 g): $^1$H NMR (CDCl$_3$) δ 8.01 (1H, d, J=8.6 Hz), 7.56 (1H, d, J=2.7 Hz), 7.20 (1H, dd, J=8.6, 2.7 Hz), 6.09 (1H, s), 5.49 (1H, t, J=6.8 Hz), 4.57 (2H, d, J=6.8 Hz), 3.94 (3H, s), 1.81 (3H, s), 1.76 (3H, S). The ethyl acetate extracts were pooled, extracted with saturated NaHCO$_3$ (2×150 mL), and the resultant aqueous extracts were acidified with concentrated HCl and filtered to recover 51 (2.10 g, 21%).

The main ethyl acetate extract was concentrated in vacuo. The residue was dissolved in a mixture of 1 N NaOH (500 mL) and diethyl ether (300 mL). After separation, the organic layer was extracted with 1 N NaOH (100 mL) and concentrated in vacuo. The residue was chromatographed on silica gel (10% ethyl acetate in hexanes) to afford a second portion of 53 (3.43 g, 30% total).

The NaOH extracts were acidified by concentrated HCl (50 mL), and extracted with ethyl acetate (2×200 mL). The pooled extracts were dried (MgSO$_4$), concentrated in vacuo, and the residue was purified by chromatography on silica gel (10% ethyl acetate in hexanes) to afford 52 (4.39 g, 32%): $^1$H NMR (CDCl$_3$) δ 8.05 (1H, d, J=8.6 Hz), 7.51 (1H, d, J=2.7 Hz), 7.20 (1H, dd, J=8.6, 2.7 Hz), 7.18 (OH, s), 5.20 (1H, tt, J=6.7, 1.5 Hz), 3.93 (3H, s), 3.29 (2H, d, J=7.2 Hz), 1.79 (3H, s), 1.68 (3H, s); $^{13}$C NMR (CDCl$_3$) δ 183.99 (s), 181.85 (s), 163.28 (s), 152.51 (s), 133.71 (s), 131.18 (s), 129.04 (d), 126.23 (d), 123.28 (s), 120.69 (d), 119.82 (d), 109.82 (d), 55.89 (q), 25.77 (q), 22.60 (t), 17.90 (q).

8-Methoxy-β-lapachone (54) Concentrated H$_2$SO$_4$ (25 mL) was added to compound 52 (2.454 g) at 20° C. After stirring for 20 min, the mixture was diluted with ice water (500 mL). The resulting red precipitate 54 was collected by filtration, washed with water, and dried in vacuo. It was obtained as a red powder (2.36 g, 96%): $^1$H NMR (CDCl$_3$) δ 7.72 (1H, d, J=8.6 Hz), 7.56 (1H, d, J=2.7 Hz), 7.12 (1H, dd, J=8.6, 2.7 Hz), 3.90 (3H, S), 2.55 (2H, t, J=6.7 Hz), 1.84 (2H, t, J=6.7 Hz), 1.46 (6H, S).

8-Hydroxy-β-lapachone (55) Boron tribromide (15.0 mL, 1.0 M in CH$_2$Cl$_2$) was added to a solution of 54 (1.05 g, mmol) in anhydrous CH$_2$Cl$_2$ (40 mL) at 0° C. After stirring for 15 min, the mixture was allowed to warm to 20° C. and kept stirring for 2 h. Ice water (500 mL) was added, the mixture was extracted with CHCl$_3$ (3×100 mL), the combined extracts were dried, and concentrated in vacuo. The residue was treated with concentrated H$_2$SO$_4$ (20 mL) at 20° C. The mixture was diluted with ice water (500 mL) and extracted with CHCl$_3$ (3×100 mL). The combined extracts were reextracted with aqueous 5% NaHSO$_3$ (3×150 mL). The aqueous extracts were acidified with concentrated HCl (100 mL), and extracted with CHCl$_3$ (3×150 mL). The extracts were dried and concentrated to afford 55 (270 mg, 27%): $^1$H NMR (CDCl$_3$) δ 9.81 (OH, s), 7.64 (1H, d, J=8.5 Hz), 7.49 (1H, d, J=2.6 Hz), 7.06 (1H, dd, J=8.5, 2.6 Hz), 2.51 (2H, t, J=6.6 Hz), 1.84 (2H, t, J=6.6 Hz), 1.45 (6H, s); HRMS (m/z) calcd for C$_{15}$H$_{14}$O$_4$ 258.0892, found 258.0885.

Preparation of 1,2-Naphthoquinone Bisulfite Adducts

General Procedure I. The quinone was dissolved in 10% NaHSO$_3$. After standing for several hours at room temperature or with cooling, the quinone-bisulfite adduct precipitated. The quinone-bisulfite was collected by filtration and dried. The quinone-bisulfite was stablized with addition of 300% its weight of sodium bisulfite.

General Procedure II. The quinone is dissolved in 10% NaHSO$_3$ in a volume of solution such that there is no more than 300% weight excess of NaHSO$_3$ (relative to quinone-bisulfite). When the quinone-bisulfite did not precipitate, it was recovered from the solution by evaporation of the water in vacuo. This procedure gives a quinone-bisulfite adduct with a 300% weight excess NaHSO$_3$.

Synthesis of Morpholino-Ser-Lys-Leu-Gln-β-Ala-β-Lapachone (Scheme 13)

Boc-Gln-β-Ala-β-Lapachone
To a solution of 1.000 g (2.437 mmol) of β-Ala-β-Lapachone-TFA salt (SL-11006) and 600.3 mg (2.437 mmol) of Boc-Gln in 10 mL of DMF was added 395.3 mg (2.925 mmol) of 1-hydroxybenzotriazole. The mixture was cooled in an ice bath. Then 270 µL (2.456 mmol) of N-methylmorpholine were added, followed by 553.0 mg (2.680 mmol) of DCC. The reaction mixture was stirred in the ice bath for 30 min and at room temperature for 6.5 hr. The reaction mixture was then diluted with CH$_2$Cl$_2$ and filtered. The filtrate was washed with saturated NaHCO$_3$ (50 mL), with 5% citric acid (3×50 mL), with saturated NaHCO$_3$ (2×50 mL), with saturated NaCl (50 mL), dried with MgSO$_4$, and evaporated to dryness. Purification by column chromatography on silica gel with 5% MeOH in CH$_2$Cl$_2$ afforded 692.7 mg (51%) of peptide as an orange glassy solid: R$_f$=0.11 (5% MeOH in CH$_2$Cl$_2$); $^1$H NMR (250 MHz, acetone-d$_6$, TMS) δ 8.00 (dd, J=7.6, 1.3 Hz, 1H), 7.9-7.7 (m, 2H), 7.64 (td, J=7.6, 1.3 Hz, 1H), 7.5-7.4 (br d, NH), 6.9 (br s, NH), 6.2 (br s, NH), 5.2-5.1 (m, 1H), 4.1-4.0 (m, 1H), 3.5-3.4 (m, 2H), 2.7-2.5, (m, 4H), 2.3-2.2 (m, 2H), 2.0-1.8 (m, 2H), 1.53 (s, 3H), 1.51 (s, 3H), 1.39 (s, 9H); $^{13}$C NMR (52 MHz, acetone-d$_6$, TMS) δ 179.8, 178.8, 175.0, 172.5, 171.6, 160.8, 156.2, 111.1, 135.6, 133.0, 131.6, 131.2, 128.7, 124.8, 80.8, 80.3, 79.2, 70.2, 54.8, 35.6, 34.7, 32.1, 28.4, 24.8, 23.2, 23.1.

Gln-β-Ala-β-Lapachone
To a solution of 681.9 mg (1.223 mmol) of Boc-Gln-β-Ala-β-Lapachone in 10 mL of CH$_2$Cl$_2$ was added 10 mL of TFA. The reaction mixture was stirred at room temperature for 25-30 min. The solvent was removed in vacuo. Column chromatography on silica gel with 10-20% MeOH in CH$_2$Cl$_2$ afforded 578.5 mg (83%) of the TFA salt as an orange glassy solid: R$_f$=0.55 (BuOH/H$_2$O/AcOH=5:3:2), 0.05 (10% MeOH in CH$_2$Cl$_2$), 0.24 (5% MeOH in CH$_2$Cl$_2$).

Boc-Leu-Gln-β-Ala-β-Lapachone
To a solution of 650.2 mg (1.138 mmol) of Gln-β-Ala-β-Lapachone-TFA salt and 263.0 mg (1.138 mmol) of Boc-Leu in 4.6 mL of DMF was added 184.5 mg (1.365 mmol) of 1-hydroxybenzotriazole. The mixture was cooled in an ice bath. Then 130 µL (1.182 mmol) of N-methylmorpholine were added, followed by 258.4 mg (1.252 mmol) of DCC. The reaction mixture was stirred in the ice bath for 30 min and at room temperature for 6.5 hr. The reaction mixture was then diluted with $CH_2Cl_2$ and filtered. The filtrate was washed with saturated $NaHCO_3$ (30 mL), with 5% citric acid (4×30 mL), with saturated $NaHCO_3$ (3×30 mL), with saturated NaCl (30 mL), dried with $MgSO_4$, and evaporated to dryness. Purification by column chromatography on silica gel with 5% MeOH in $CH_2Cl_2$ afforded 396.9 mg (51%) of peptide as a yellow-orange glassy solid: $R_f$=0.11 (5% MeOH in $CH_2Cl_2$), 0.45 (10% MeOH in $CH_2Cl_2$), 0.81 (20% MeOH in $CH_2Cl_2$), 0.78 ($BuOH/H_2O/AcOH$=5:3:2); $^1H$ NMR (250 MHz, acetone-$d_6$, TMS) δ 8.00 (d, J=7.5 Hz, 1H), 7.9-7.7 (m, 2H), 7.64 (t, J=7.5 Hz, 1H), 7.5 (br d, NH), 6.9 (br s, NH), 6.3 (br s, NH), 5.2-5.1 (m, 1H), 4.4-4.2 (m, 1H), 4.1-4.0 (m, 1H), 3.6-3.3 (m, 2H), 2.7-2.5 (m, 4H), 2.3-2.2 (m, 2H), 2.0-1.8 (m, 2H), 1.8-1.7 (m, 1H), 1.6-1.5 (m, 2H), 1.53 (s, 3H), 1.51 (s, 3H), 1.39 (s, 9H), 1.0-0.9 (m, 6H); $^{13}C$ NMR (52 MHz, acetone-$d_6$, TMS) δ 179.9, 179.0, 175.2, 173.4, 172.0, 171.5, 160.9, 156.8, 135.7, 133.1, 131.6, 131.2, 128.8, 124.9, 111.2, 80.9, 80.4, 79.5, 70.3, 54.5, 53.5, 41.7, 35.8, 34.8, 32.1, 28.5, 27.8, 25.4, 24.9, 23.4, 23.2, 21.9.

Leu-Gln-β-Ala-β-Lapachone

To a solution of 317.0 mg (4.725×10$^{-4}$ mol) of Boc-Leu-Gln-β-Ala-β-Lapachone in 4 mL of $CH_2Cl_2$ was added 4 mL of TFA. The reaction mixture was stirred at room temperature for 25-30 min. The solvent was removed in vacuo. Column chromatography on silica gel with 20% MeOH in $CH_2Cl_2$ afforded 277.3 mg (86%) of the TFA salt as an orange glassy solid: $R_f$=0.17 (10% MeOH in $CH_2Cl_2$), 0.39 (20% MeOH in $CH_2Cl_2$), 0.74 ($BuOH/H_2O/AcOH$=5:3:2).

Nα-Boc-Lys(Nε-Cbz)-Leu-Gln-β-Ala-β-Lapachone

To a solution of 277.3 mg (4.050×10$^{-4}$ mol) of Leu-Gln-β-Ala-β-Lapachone-TFA salt and 168.0 mg (4.049×10$^{-4}$ mol) of Nα-Boc-Lys(Nε-Cbz) in 1.6 mL of DMF was added 65.7 mg (4.862×10$^{-4}$ mol) of 1-hydroxybenzotriazole. The mixture was cooled in an ice bath. Then 50 μL (4.548×10$^{-4}$ mol) of N-methylmorpholine were added, followed by 91.9 mg (4.454×10$^{-4}$ mol) of DCC. The reaction mixture was stirred in the ice bath for 30 min and at room temperature for 6.5 hr. The reaction mixture was then diluted with 2 mL of $CHCl_3$ and filtered. The filtrate was washed with saturated $NaHCO_3$ (20 mL), with 5% citric acid (4×20 mL), with saturated $NaHCO_3$ (3×20 mL), with saturated NaCl (2×20 mL), dried with $MgSO_4$, and evaporated to dryness. Purification by column chromatography on silica gel with 10% MeOH in $CH_2Cl_2$ afforded 167.5 mg (42%) of peptide as an orange glassy solid: $R_f$=0.08 (5% MeOH in $CH_2Cl_2$), 0.44 (10% MeOH in $CH_2Cl_2$); $^1H$ NMR (250 MHz, DMSO-$d_6$, TMS) δ 8.0-7.7 (m, 6H, quinone-H5, H6, H7, H8, & NH's), 7.7-7.6 (m, NH), 7.5-7.4 (m, 2H, Cl-Cbz), 7.4-7.3 (m, 2H, Cl-Cbz), 7.20 (br s, NH), 6.73 (br s, NH), 6.90 (br d, J=7.9 Hz, NH), 5.07 (s, 3H), 4.3-4.2 (m, 1H), 4.2-4.1 (m, 1H), 3.9-3.8 (m, 1H), 3.3-3.2 (m, 2H), 3.0-2.9 (m, 2H), 2.8-2.7 (m, 2H), 2.6-2.4 (m, 2H), 2.1-2.0 (m, 2H), 1.8-1.3 (m, 11H), 1.43 (s, 3H), 1.39 (s, 3H), 1.36 (s, 9H), 0.85 (d, J=6.5 Hz, 3H), 0.81 (d, J=6.6 Hz, 3H); $^{13}C$ NMR (52 MHz, DMSO-$d_6$, TMS) δ 178.6, 177.8, 173.5, 173.4, 172.0, 171.7, 171.0, 170.5, 162.2, 155.7, 134.9, 134.5, 132.2, 131.4, 130.9, 129.9, 129.5, 129.2, 127.9, 127.2, 123.7, 79.7, 79.3, 78.0, 68.9, 62.4, 54.2, 52.0, 50.8, 40.7, 35.7, 33.5, 31.2, 30.7, 29.0, 28.1, 27.8, 24.1, 23.9, 23.0, 22.8, 22.7, 22.1, 21.4.

Lys(Nε-Cbz)-Leu-Gln-β-Ala-β-Lapachone

To a suspension of 203.1 mg (2.099×10$^{-4}$ mol) of Boc-Lys(Nε-Cbz)-Leu-Gln-β-Ala-β-Lapachone in 2 mL of $CHCl_3$ was added 1.7 mL of TFA (material dissolved). The reaction mixture was stirred at room temperature for 20-25 min. The solvent was removed in vacuo. Column chromatography on silica gel with 20% MeOH in $CH_2Cl_2$ afforded 202.0 mg (98%) of the TFA salt as an orange glassy solid: $R_f$=0.10 (10% MeOH in $CH_2Cl_2$), 0.40 (20% MeOH in $CH_2Cl_2$).

Morpholino-Ser(OBn)-Lys(Nε-Cbz)-Leu-Gln-β-Ala-β-Lapachone

To a solution of 194.8 mg (1.985×10$^{-4}$ mol) of Lys(Nε-Cbz)-Leu-Gln-β-Ala-β-Lapachone-TFA salt and 61.2 mg (1.985×10$^{-4}$ mol) of morpholino-Ser(OBn) in 1.0 mL of DMF was added 32.2 mg (2.383×10$^{-4}$ mol) of 1-hydroxybenzotriazole. The mixture was cooled in an ice bath. Then 23 μL (2.092×10$^{-4}$ mol) of N-methylmorpholine were added, followed by 45.1 mg (2.186×10$^{-4}$ mol) of DCC. The reaction mixture was stirred in the ice bath for 35 min and at room temperature for 6 hr. The reaction mixture was then diluted with 2 mL of $CH_2Cl_2$ and filtered. The filtrate was washed with 5% citric acid (3×20 mL), with saturated $NaHCO_3$ (3×20 mL), with saturated NaCl (20 mL), dried with $MgSO_4$, and evaporated to dryness. Purification by column chromatography on silica gel with 10% MeOH in $CH_2Cl_2$ afforded 83.3 mg (36%) of peptide as an orange glassy solid: $R_f$=0.05 (5% MeOH in $CH_2Cl_2$), 0.41 (10% MeOH in $CH_2Cl_2$); $^1H$ NMR (250 MHz, acetone-$d_6$, TMS) δ 8.0-7.7 (m, 7H, quinone-H5, H6, H7, H8, NH's), 7.7-7.6 (m, NH), 7.5-7.2 (m, 10H, Cl-Cbz, OBn, NH), 6.75 (br s, NH), 6.60 (br d, J=7.1 Hz, NH), 5.07 (s, 3H), 4.49 (s, 2H), 4.4-4.3 (m, 1H), 4.3-4.0 (m, 3H), 3.7-3.6 (m, 2H), 3.6-3.5 (m, 4H), 3.3-3.2 (m, 6H), 3.0-2.9 (m, 2H), 2.8-2.7 (m, 2H), 2.5-2.4 (m, 2H), 2.1-2.0 (m, 2H), 1.8-1.3 (m, 11H), 1.43 (s, 3H), 1.38 (s, 3H), 0.82 (d, J=6.0 Hz, 3H), 0.78 (d, J=6.1 Hz, 3H).

Morpholino-Ser-Lys-Leu-Gln-β-Ala-β-Lapachone (SL-11147)

To a solution of 78.3 mg (6.763×10$^{-5}$ mol) of morpholino-Ser(OBn)-Lys(Nε-Cbz)-Leu-Gln-β-Ala-β-Lapachone in 1.5 mL of MeOH/$CH_2Cl_2$=1:9 was added 30.6 mg 10% Pd/C. Then 0.5 mL of MeOH and one drop of HCl were added. The reaction mixture was placed under an atmosphere of $H_2$ (balloon) and stirred at room temperature for 16 hr. Removal of catalyst by filtration and evaporation of solvent afforded 64.5 mg of crude quinone-tetrapeptide. The material was purified by prep HPLC to yield 14.4 mg (24%): $R_f$=0.04 (20% MeOH in $CH_2Cl_2$).

N-Fmoc-Ser(OBn) t-butyl ester

Isobutylene was condensed into a 500 mL pressure bottle until the volume was between 30 and 40 mL. A solution of 3.02 g (7.23 mmol) of N-Fmoc-Ser(OBn) in 20 mL of THF was added, followed by 2 mL of concentrated $H_2SO_4$. The bottle was securely stoppered and shaken at room temperature for 24 hr. The reaction mixture was poured into an ice-cold mixture of 150 mL of ethyl acetate and 150 mL of saturated $NaHCO_3$. The organic phase was washed with water (3×50 mL) and dried with $MgSO_4$. The solvent was removed, and column chromatography on silica gel with $CH_2Cl_2$ afforded 2.453 g (72%) of t-butyl ester as a colorless oil: $^1H$ NMR (250 MHz, acetone-$d_6$, TMS) δ 7.85 (d, J=7.5 Hz, 2H), 7.74 (d, J=7.3 Hz, 2H), 7.5-7.3 (m, 9H), 6.71 (br d, J=8.6 Hz, NH), 4.55 (ABq, $δ_A$=4.57, $δ_B$=4.52, $J_{AB}$=12 Hz, 2H), 4.4-4.2 (m, 4H), 3.9-3.7 (AB of ABX, $δ_A$=3.89, $δ_B$=3.75, $J_{AB}$=9.5 Hz, $J_{AX}$=4.6 Hz, $J_{BX}$=3.6 Hz, 2H); $^{13}C$ NMR (52 MHz, acetone-$d_6$, TMS) δ 170.0, 156.8, 145.0, 144.9, 142.0, 129.0, 128.4, 128.3, 128.2, 127.8, 126.1, 120.7, 81.9, 73.6, 70.9, 67.3, 55.9, 47.9, 28.1.

Ser(OBn) t-butyl ester

To a solution of 3.049 g (6.44 mmol) of N-Fmoc-Ser (OBn) t-butyl ester in 50 mL of $CH_2CL_2$ was added 3 mL of piperidine. The reaction mixture was stirred at room temperature for 2.3 hr. Removal of solvent and column chromatography on silica gel with 5% MeOH in $CH_2Cl_2$ yielded 1.306 g (81%) of Ser(OBn) t-butyl ester as a colorless oil: $R_f$=0.12 (2% MeOH in $CH_2Cl_2$); $^1$H NMR (250 MHz, acetone-$d_6$, TMS) δ 7.4-7.2 (m, 5H), 4.53 (Abq, $δ_A$=4.55, $δ_B$=4.52, $J_{AB}$=12 Hz, 2H), 3.7-3.6 (m, AB of ABX, $δ_A$=3.68, $δ_B$=3.61, $J_{AB}$=12 Hz, $J_{AX}$=4.9 Hz, $J_{BX}$=4.4 Hz, 2H), 3.5-3.4 (m, X of ABX, $δ_X$=3.45, 1H), 1.43 (s, 9H); $^{13}$C NMR (52 MHz, acetone-$d_6$, TMS) δ 173.9, 139.5, 128.9, 128.2, 128.1, 80.7, 73.8, 73.5, 56.2, 28.1.

Morpholino-Ser(OBn) t-butyl ester

To a solution of 140.6 mg (5.59×10$^{-4}$ mol) of Ser(OBn) t-butyl ester in 4 mL of pyridine was added 66 μL (5.66× 10$^{-4}$ mol) of 4-morpholinecarbonyl chloride. After stirring for 1 hr, the reaction mixture was partitioned between 75 mL of $CH_2Cl_2$ and 60 mL of water. The organic phase was washed with saturated $NaHCO_3$ (50 mL), with 1N HCl (2×50 mL), with saturated NaCl (50 mL), dried with $MgSO_4$, and evaporated to dryness. The crude amide was purified by column chromatography on silica gel with ethyl acetate to yield 80.9 mg (40%) of amide as a light orange oil: $R_f$=0.58 (ethyl acetate), 0.60 (5% MeOH in $CH_2Cl_2$); $^1$H NMR (250 MHz, acetone-$d_6$, TMS) δ 7.4-7.2 (m, 5H), 5.8 (br d, NH), 4.53 (Abq, $δ_A$=4.55, $δ_B$=4.52, $J_{AB}$=12 Hz, 2H), 4.5-4.4 (m, X of ABX, $δ_X$=4.47, 1H), 3.9-3.6 (m, AB of ABX, $δ_A$=3.86, $δ_B$=3.69, $J_{AB}$=9.4 Hz, $J_{AX}$=4.4 Hz, $J_{BX}$=3.7 Hz, 2H), 3.63-3.58 (m, 4H), 3.4-3.3 (m, 4H), 1.44 (s, 9H); $^{13}$C NMR (52 MHz, acetone-$d_6$, TMS) δ 170.9, 157.9, 139.2, 129.0, 128.3, 128.2, 81.5, 73.5, 71.3, 67.0, 55.5, 44.9, 28.1.

Morpholino-Ser(OBn)

A solution of 80 mg (2.195×10$^{-4}$ mol) of morpholino-Ser (OBn) t-butyl ester in a mixture of 1.5 mL of $CH_2Cl_2$ and 1.5 mL of TFA was stirred at room temperature for 30 min. The solvent was removed in vacuo and the remaining TFA was removed by repeated evaporation with acetone. The residue was triturated with $Et_2O$. The material was then filtered, washed with $Et_2O$, washed with 0.5 mL acetone, washed again with $Et_2O$, and dried to yield 41.8 mg (62%) of amino acid as an off-white solid: $R_f$=0.72 ($BuOH/H_2O/AcOH$=5:3:2); $^1$H NMR (250 MHz, acetone-$d_6$, TMS) δ 7.4-7.3 (m, 5H), 6.0-5.9 (br d, NH), 4.6-4.5 (m, 3H, $OCH_2Ph$ & X of ABX), 3.95-3.75 (m, AB of ABX, $δ_A$=3.90, $δ_B$=3.73, $J_{AB}$=9.6 Hz, $J_{AX}$=4.9 Hz, $J_{BX}$=3.9 Hz, 2H), 3.6-3.5 (m, 4H), 3.4-3.3 (m, 4H); $^{13}$C NMR (52 MHz, DMSO-$d_6$, TMS) d 172.4, 157.2, 138.2, 128.2, 127.4, 127.4, 72.0, 69.5, 65.9, 53.8, 43.9.

Synthesis of
Morpholino-Ser-Lys-Leu-Gln-Leu-β-Lapachone
(Scheme 14)

Boc-Leu-β-Lapachone

A solution of 2.820 g (12.20 mmol) of Boc-Leu and 1.976 g (12.19 mmol) of 1,1-carbonyldiimidazole in 33 mL of DMF was stirred at room temperature for 20 min. To the solution was added 2.100 g (8.130 mmol) of 3-hydroxy-β-lapachone followed by 1.6 mL (10.70 mmol) of DBU. After stirring at room temperature for 5 hr, the reaction mixture was partitioned between 200 mL of water and 200 mL of $CHCl_3$. The aqueous phase was washed with $CHCl_3$ (4×50 mL). The $CHCl_3$ extracts were combined, dried with $MgSO_4$, and evaporated to dryness. Column chromatography on silica gel with 2% MeOH in $CH_2Cl_2$ afforded 2.038 g (53%) of quinone as an orange glassy solid (and mixture of two diastereomers): $R_f$=0.45 (5% MeOH in $CH_2Cl_2$); $^1$H NMR (250 MHz, acetone-$d_6$, TMS) δ 8.1-8.0 (m, 1H), 8.0-7.9 (m, 1H), 7.9-7.8 (m, 1H), 7.7-7.6 (m, 1H), 6.34 (br d, NH), 5.2-5.1 (m, 1H), 4.2-4.1 (m, 1H), 2.9-2.8 (m, 1H), 2.7-2.5 (m, 1H), 1.8-1.6 (m, 3H), 1.56 (s, 1.5H), 1.53 (s, 3H), 1.52 (s, 1.5H), 1.34 (s, 4.5H), 1.33 (s, 4.5H), 0.91 (d, J=7.0 Hz, 1.5H), 0.88 (d, J=6.7 Hz, 1.5H), 0.84 (d, J=6.3 Hz, 1.5H), 0.82 (d, J=6.1 Hz, 1.5H).

Leu-β-Lapachone

To a solution of 2.017 mg (4.277 mmol) of Boc-Leu-β-Lapachone in 20 mL of $CH_2Cl_2$ was added 20 mL of TFA. The reaction mixture was stirred at room temperature for 30 min. The solvent was removed in vacuo. Column chromatography on silica gel with 20% MeOH in $CH_2Cl_2$ afforded 2.507 g (quant.) of the TFA salt as an orange glassy solid: $R_f$=0.52 (10% MeOH in $CH_2Cl_2$), 0.82 (20% MeOH in $CH_2Cl_2$); $^1$H NMR (250 MHz, DMSO-$d_6$, TMS) δ 8.6-8.5 (br s, NH), 8.0-7.9 (m, 1H), 7.9-7.8 (m, 2H), 7.7-7.6 (m, 1H), 5.3-5.2 (m, 1H), 4.1-4.0 (m, 1H), 2.8-2.5 (m, 2H), 1.8-1.5 (m, 3H), 1.52 (s, 1.5H), 1.49 (s, 1.5H), 1.43 (s, 3H), 0.83 (d, J=6.0 Hz, 3H), 0.66 (br t, 3H); $^{13}$C NMR (52 MHz, DMSO-$d_6$, TMS) δ 178.7, 177.8, 169.2, 169.1, 160.0, 159.7, 135.1, 135.1, 131.5, 131.4, 131.1, 131.0, 129.8, 129.8, 127.9, 123.9, 123.8, 109.6, 109.3, 79.4, 79.1, 71.1, 70.9, 50.6, 50.4, 39.0, 24.0, 23.9, 22.9, 22.3, 22.1, 22.0, 21.8, 21.7, 21.1.

Boc-Gln-Leu-β-Lapachone

To a solution of 2.235 g (3.895 mmol) of Leu-β-Lapachone-TFA salt and 959.1 mg (3.894 mmol) of Boc-Gln in 15.6 mL of DMF was added 631.4 mg (4.673 mmol) of 1-hydroxybenzotriazole. The mixture was cooled in an ice bath. Then 760 μL (6.912 mmol) of N-methylmorpholine were added, followed by 883.9 mg (4.284 mmol) of DCC. The reaction mixture was stirred in the ice bath for 30 min and at room temperature for 5.8 hr. The reaction mixture was then diluted with 8 mL of $CH_2Cl_2$ and filtered. The filtrate was washed with 5% citric acid (3×50 mL), with saturated $NaHCO_3$ (3×50 mL), with saturated NaCl (50 mL), dried with $MgSO_4$, and evaporated to dryness. Purification by column chromatography on silica gel with 5% MeOH in $CH_2Cl_2$ afforded 1.555 g (66%) of peptide as an orange glassy solid: $R_f$=0.19 (5% MeOH in $CH_2Cl_2$), 0.09 (5% MeOH in $CHCl_3$), 0.37 (10% MeOH in $CHCl_3$); $^1$H NMR (250 MHz, DMSO-$d_6$, TMS) δ 8.24 (br d, J=7 Hz, NH), 8.17 (br d, J=7 Hz, NH), 8.0-7.9 (m, 1H), 7.8-7.7 (m, 2H), 7.7-7.6 (m, 1H), 7.22 (br s, NH), 6.83 (br d, J=8 Hz, NH), 6.76 (br s, NH), 5.1-5.0 (m, 1H), 4.3-4.1 (m, 1H), 3.9-3.8 (m, 1H), 2.8-2.6 (m, 1H), 2.6-2.4 (m, 1H), 2.1-2.0 (m, 2H), 1.8-1.4 (m, 5H), 1.47 (s, 1.5H), 1.43 (s, 1.5H), 1.42 (s, 1.5H), 1.40 (s, 1.5H), 1.36 (s, 9H), 0.86 (d, J=6.3 Hz, 1.5H), 0.79 (d, J=6.2 Hz, 1.5H), 0.73 (br t, 3H); $^{13}$C NMR (52 MHz, DMSO-$d_6$, TMS) δ 178.7, 177.8, 177.7, 173.7, 172.0, 171.7, 171.5, 159.9, 159.7, 155.1, 135.1, 135.0, 131.5, 131.4, 131.0, 130.9, 129.8, 129.7, 127.9, 127.8, 123.8, 109.8, 109.6, 79.5, 79.3, 77.9, 69.6, 69.4, 53.7, 53.6, 50.5, 50.4, 31.4, 28.1, 27.6, 27.4, 24.2, 24.1, 24.0, 22.6, 22.5, 22.1, 21.9, 21.6, 21.2.

Gln-Leu-β-Lapachone

To a solution of 1.519 g (2.533 mmol) of Boc-Gln-Leu-β-Lapachone in 12 mL of $CH_2Cl_2$ was added 11 mL of TFA. The reaction mixture was stirred at room temperature for 30 min. The solvent was removed in vacuo. Column chromatography on silica gel with 20% MeOH in $CH_2Cl_2$ afforded 1.976 mg (quant) of the TFA salt as an orange glassy solid; $^1$H NMR (250 MHz, DMSO-$d_6$, TMS) δ 8.97 (br d, J=6.5

Hz, NH), 8.90 (br d, J=7.0 Hz, NH), 8.30 (br s, NH), 8.0-7.9 (m, 1H), 7.9-7.8 (m, 2H), 7.7-7.6 (m, 1H), 7.45 (br s, NH), 6.98 (br s, NH), 5.2-5.1 (m, 1H), 4.3-4.2 (m, 1H), 3.9-3.8 (m, 1H), 2.8-2.7 (m, 1H), 2.5-2.4 (m, 1H), 2.2-2.1 (m, 2H), 2.0-1.8 (m, 2H), 1.7-1.5 (m, 3H), 1.49 (s, 1.5H), 1.44 (s, 1.5H), 1.42 (s, 1.5H), 1.41 (s, 1.5H), 0.87 (d, J=6.3 Hz, 1.5H), 0.81 (d, J=6.3 Hz, 1.5H), 0.75 (d, J=5.8 Hz, 1.5H), 0.73 (d, J=5.8 Hz, 1.5H); $^{13}$C NMR (52 MHz, DMSO-$d_6$, TMS) δ 178.7, 177.8, 177.8, 173.5, 171.3, 171.1, 168.7, 168.7, 159.9, 159.8, 135.1, 131.5, 131.4, 131.1, 131.0, 129.9, 129.8, 128.0, 123.8, 109.7, 109.5, 79.5, 79.3, 69.9, 69.8, 51.7, 51.6, 50.8, 50.8, 30.3, 26.8, 24.2, 24.1, 22.7, 22.5, 22.2, 22.0, 21.9, 21.6, 21.2.

Boc-Leu-Gln-Leu-β-Lapachone

To a solution of 1.949 g (max 2.533 mmol) of Gln-Leu-β-Lapachone-TFA salt and 585.7 mg (2.533 mmol) of Boc-Leu in 10 mL of DMF was added 410.6 mg (3.038 mmol) of 1-hydroxybenzotriazole. The mixture was cooled in an ice bath. Then 685 μL (6.230 mmol) of N-methylmorpholine were added, followed by 574.7 mg (2.785 mmol) of DCC. The reaction mixture was stirred in the ice bath for 30 min and at room temperature for 5.5 hr. The reaction mixture was then diluted with CHCl$_3$ and filtered. The filtrate was washed with 5% citric acid (5×50 mL), with saturated NaHCO$_3$ (4×70 mL), with saturated NaCl (70 mL), dried with MgSO$_4$, and evaporated to dryness. Purification by column chromatography on silica gel with 5% MeOH in CHCl$_3$ afforded 1.221 g (68%, from Boc-Gln-Leu-β-Lapachone) of peptide as an orange glassy solid: $R_f$ 0.09 (5% MeOH in CHCl$_3$), 0.29 (7% MeOH in CHCl$_3$); $^1$H NMR (250 MHz, DMSO-$d_6$, TMS) δ 8.36 (br d, NH), 8.30 (br d, NH), 8.0-7.9 (m, 1H), 7.9-7.7 (m, 2H), 7.7-7.6 (m, 1H), 7.19 (br s, NH), 6.90 (br s, NH), 6.75 (br d, NH), 5.1-5.0 (m, 1H), 4.3-4.1 (m, 2H), 4.0-3.9 (m, 1H), 2.8-2.7 (m, 1H), 2.5-2.4 (m, 1H), 2.1-2.0 (m, 2H), 1.8-1.4 (m, 8H), 1.47 (s, 1.5H), 1.43 (s, 1.5H), 1.41 (s, 1.5H), 1.40 (s, 1.5H), 1.37 (s, 4.5H), 1.35 (s, 4.5H), 0.9-0.8 (m, 7.5H), 0.78 (d, J=6.2 Hz, 1.5H), 0.73 (d, J=5.5 Hz, 1.5H), 0.71 (d, J=5.3 Hz, 1.5H); $^{13}$C NMR (52 MHz, DMSO-$d_6$, TMS) δ 178.7, 177.8, 177.7, 173.6, 173.6, 172.3, 171.5, 171.4, 171.3, 159.9, 159.7, 155.2, 135.0, 131.5, 131.4, 131.0, 130.9, 129.8, 129.8, 127.9, 127.9, 123.8, 109.7, 109.6, 79.5, 79.3, 78.0, 69.6, 69.5, 52.8, 51.4, 50.5, 50.5, 40.7, 31.2, 28.1, 24.2, 24.1, 22.9, 22.6, 22.5, 22.1, 22.0, 21.9, 21.6, 21.4, 21.2.

Leu-Gln-Leu-β-Lapachone

To a solution of 1.196 g (1.678 mmol) of Boc-Leu-Gln-Leu-β-Lapachone in 8 mL of CH$_2$Cl$_2$ was added 8 mL of TFA. The reaction mixture was stirred at room temperature for 30 min. The solvent was removed in vacuo. Column chromatography on silica gel with 20% MeOH in CHCl$_3$ afforded 1.430 g (quant) of the TFA salt as an orange glassy solid: $R_f$=0.04 (10% MeOH in CHCl$_3$), 0.10 (15% MeOH in CHCl$_3$), 0.19 (20% MeOH in CHCl$_3$); $^1$H NMR (250 MHz, DMSO-$d_6$, TMS) δ 8.46 (br d, J=6.6 Hz, NH), 8.41 (br d, J=7.2 Hz, NH), 8.0-7.9 (m, 1H), 7.9-7.8 (m, 2H), 7.7-7.6 (m, 1H), 7.26 (br s, NH), 6.77 (br s, NH), 5.1-5.0 (m, 1H), 4.3-4.1 (m, 2H), 3.5-3.4 (m, 1H), 2.8-2.7 (m, 1H), 2.5-2.4 (m, 1H), 2.1-2.0 (m, 2H), 1.9-1.4 (m, 8H), 1.47 (s, 1.5H), 1.43 (s, 1.5H), 1.41 (s, 1.5H), 1.40 (s, 1.5H), 0.9-0.8 (m, 7.5H), 0.78 (d, J=6.1 Hz, 1.5H), 0.74 (d, J=5.9 Hz, 1.5H), 0.72 (d, J=5.5 Hz, 1.5H); $^{13}$C NMR (52 MHz, DMSO-$d_6$, TMS) δ 178.7, 177.8, 177.8, 173.6, 171.6, 171.4, 171.2, 159.9, 159.8, 135.1, 131.5, 131.4, 131.1, 131.0, 129.9, 129.8, 127.9, 123.9, 109.8, 109.6, 79.6, 79.3, 69.6, 69.5, 51.9-51.6, 51.6, 50.5, 42.3-41.8, 31.2, 28.2, 28.0, 24.2, 24.1, 23.7, 22.8, 22.7, 22.6, 22.1, 21.9, 21.8, 21.6, 21.3, 21.2.

Nα-Boc-Lys(Nε-Cl-Cbz)-Leu-Gln-Leu-β-Lapachone

To a solution of 1.400 g (max 1.643 mmol) of Leu-Gln-Leu-β-Lapachone-TFA salt and 681.6 mg (1.643 mmol) of Nα-Boc-Lys(Nε-Cl-Cbz) in 6.6 mL of DMF was added 266.3 mg (1.971 mmol) of 1-hydroxybenzotriazole. The mixture was cooled in an ice bath. Then 380 μL (3.456 mmol) of N-methylmorpholine were added, followed by 372.9 mg (1.807 mmol) of DCC. The reaction mixture was stirred in the ice bath for 30 min and at room temperature for 5.5 hr. The reaction mixture was then diluted with CHCl$_3$ and filtered. The filtrate was washed with 5% citric acid (4×50 mL), with saturated NaHCO$_3$ (4×50 mL), with saturated NaCl (65 mL), dried with MgSO$_4$, and evaporated to dryness. Purification by column chromatography on silica gel with 5% MeOH in CHCl$_3$ afforded 897.4 mg (54%) of peptide as an orange glassy solid: $R_f$=0.10 (5% MeOH in CHCl$_3$); $^1$H NMR (250 MHz, DMSO-$d_6$, TMS) δ 8.31 (br d, J=7. Hz, NH), 8.25 (br d, J=7 Hz, NH), 8.0-7.9 (m, 2H (1 quinone-H+1 NH)), 7.8-7.7 (m, 3H (2 quinone-H+1 NH)), 7.7-7.6 (m, 1H (quinone-H)), 7.5-7.4 (m, 2H), 7.4-7.3 (m, 3H (2 Cl-Ph-H+1 NH)), 7.19 (br s, NH), 6.90 (br d, J=8 Hz, NH), 6.77 (br s, NH), 5.1-5.0 (m, 4H), 4.3-4.1 (m, 3H), 3.9-3.8 (m, 1H), 3.0-2.9 (m, 2H), 2.8-2.7 (m, 1H), 2.5-2.4 (m, 1H), 2.1-2.0 (m, 2H), 1.9-1.4 (m, 14H), 1.47 (s, 1.5H), 1.42 (s, 1.5H), 1.41 (s, 1.5H), 1.40 (s, 1.5H), 1.37 (s, 9H), 0.9-0.8 (m, 7.5H), 0.77 (d, J=6.2 Hz, 1.5H), 0.73 (d, J=5.7 Hz, 1.5H), 0.70 (d, J=5.6 Hz, 1.5H); $^{13}$C NMR (52 MHz, DMSO-$d_6$, TMS) δ 178.7, 177.8, 177.7, 173.6, 171.8, 171.6, 171.4, 171.3, 159.9, 159.7, 155.7, 155.3, 135.0, 134.5, 132.2, 131.5, 131.4, 131.0, 130.9, 129.8, 129.8, 129.5, 129.1, 127.9, 127.8, 127.2, 123.8, 109.7, 109.6, 79.5, 79.3, 78.0, 69.6, 69.5, 62.4, 54.3, 51.6, 50.7, 50.5, 50.4, 41.0, 40.1, 31.3, 29.0, 28.1, 27.9, 27.7, 24.2, 24.1, 24.0, 23.9, 23.0, 22.7, 22.6, 22.5, 22.1, 22.0, 21.9, 21.6, 21.5, 21.2.

Lys(Nε-Cl-Cbz)-Leu-Gln-Leu-β-Lapachone

To a solution of 1.196 g (1.678 mmol) of Boc-Lys(Nε-Cl-Cbz)-Leu-Gln-Leu-β-Lapachone in 6 mL of CH$_2$Cl$_2$ was added 5 mL of TFA. The reaction mixture was stirred at room temperature for 30 min. The solvent was removed in vacuo. Column chromatography on silica gel with 15% MeOH in CHCl$_3$ afforded 568.9 mg (65%) of the TFA salt as an orange glassy solid: $R_f$=0.09 (10% MeOH in CHCl$_3$), 0.23 (15% MeOH in CHCl$_3$), 0.38 (20% MeOH in CHCl$_3$); $^1$H NMR (250 MHz, DMSO-$d_6$, TMS) δ 8.28 (br d, J=7 Hz, NH), 8.23 (br d, J=7 Hz, NH), 8.1-8.0 (m, NH), 8.0-7.9 (m, 2H (1 quinone-H+1 NH)), 7.8-7.7 (m, 2H), 7.7-7.6 (m, 1H), 7.5-7.4 (m, 2H), 7.4-7.3 (m, 3H (2 Cl-Ph-H+1NH)), 7.23 (br s, NH), 6.78 (br s, NH), 5.1-5.0 (m, 4H), 4.3-4.1 (m, 4H), 3.0-2.9 (m, 2H), 2.8-2.7 (m, 1H), 2.5-2.4 (m, 1H), 2.1-2.0 (m, 2H), 1.9-1.4 (m, 14H), 1.47 (s, 1.5H), 1.42 (s, 1.5H), 1.41 (s, 1.5H), 1.39 (s, 1.5H), 0.9-0.8 (m, 7.5H), 0.77 (d, J=6.2 Hz, 1.5H), 0.73 (d, J=5.8 Hz, 1.5H), 0.71 (d, J=5.6 Hz, 1.5H); $^{13}$C NMR (52 MHz, DMSO-$d_6$, TMS) δ 178.7, 177.8, 177.7, 173.7, 171.8, 171.6, 171.4, 171.3, 159.9, 159.7, 155.7, 135.0, 134.6, 132.2, 131.5, 131.4, 131.0, 130.9, 129.9, 129.8, 129.5, 129.2, 127.9, 127.8, 127.2, 123.8, 109.7, 109.6, 79.5, 79.3, 69.6, 69.4, 62.4, 54.4, 51.7, 50.6, 50.5, 50.4, 41.1, 31.2, 29.2, 27.6, 27.5, 24.2, 24.2, 24.1, 23.0, 22.6, 22.5, 22.4, 22.0, 21.9, 21.6, 21.2.

Morpholino-Ser(OBn)-Lys(Nε-Cl-Cbz)-Leu-Gln-Leu-β-Lapachone

To a solution of 544.9 mg (5.323×10$^{-4}$ mol) of Lys(Nε-Cl-Cbz)-Leu-Gln-Leu-β-Lapachone-TFA salt and 164.2 mg 5.325×10$^{-4}$ mol) of morpholino-Ser(OBn) in 2.15 mL of DMF was added 86.2 mg (6.379×10$^{-4}$ mol) of 1-hydroxybenzotriazole. The mixture was cooled in an ice bath. Then 59 μL (5.366×10$^{-4}$ mol) of N-methylmorpholine were added, followed by 120.7 mg (5.850×10$^{-4}$ mol) of DCC. The reaction mixture was stirred in the ice bath for 30 min and at room temperature for 5.5 hr. The reaction mixture was then diluted with CHCl$_3$ and filtered. The filtrate was washed with 5% citric acid (4×30 mL), with saturated NaHCO$_3$ (4×30 mL), with saturated NaCl (30 mL), dried with MgSO$_4$, and evaporated to dryness. Purification by column chromatography on silica gel with 7% MeOH in CHCl$_3$ afforded 515.8 mg (81%) of peptide as an orange glassy solid: R$_f$=0.17 (7% MeOH in CHCl$_3$), 0.36 (10% MeOH in CHCl$_3$); $^1$H NMR (250 MHz, DMSO-d$_6$, TMS) δ 8.22 (br d, J=7 Hz, NH), 8.18 (br d, J=7 Hz, NH), 8.0-7.9 (m, 2H (1 quinone-H+1 NH)), 7.9-7.7 (m, 3H (2 quinone-H+1 NH)), 7.7-7.6 (m, 1H), 7.5-7.4 (m, 2H), 7.4-7.2 (m, 8H (2 Cl-Ph-H+5 Ph-H+1 NH)), 7.20 (br s, NH), 6.78 (br s, NH), 6.60 (br d, J=7 Hz, NH), 5.1-5.0 (m, 4H), 4.50 (s, 2H), 4.4-4.3 (m, 1H), 4.3-4.1 (m, 4H), 3.7-3.6 (m, 2H), 3.6-3.5 (m, 4H), 3.3-3.2 (m, 4H), 3.0-2.9 (m, 2H), 2.8-2.6 (m, 1H), 2.5-2.4 (m, 1H), 2.1-2.0 (m, 2H), 1.9-1.4 (m, 14H), 1.46 (s, 1.5H), 1.42 (s, 1.5H), 1.41 (s, 1.5H), 1.39 (s, 1.5H), 0.9-0.7 (m, 9H), 0.72 (d, J=5.4 Hz, 1.5H), 0.70 (d, J=5.3 Hz, 1.5H); $^{13}$C NMR (52 MHz, DMSO-d$_6$, TMS) δ 178.7, 177.8, 177.7, 173.6, 171.6, 171.5, 171.4, 171.3, 171.3, 170.8, 170.8, 159.9, 159.7, 157.3, 155.7, 138.2, 135.0, 134.5, 132.2, 131.5, 131.4, 131.0, 130.9, 129.9, 129.8, 129.5, 129.1, 128.1, 127.9, 127.8, 127.4, 127.3, 127.2, 123.8, 109.8, 109.6, 79.5, 79.3, 71.9, 69.6, 69.5, 65.8, 62.4, 54.6, 52.7, 51.7, 51.0, 50.5, 50.4, 43.9, 31.3, 31.3, 29.0, 27.8, 27.7, 24.2, 24.2, 24.1, 24.0, 22.9, 22.5, 22.5, 22.0, 21.8, 21.6, 21.4, 21.2.

Morpholino-Ser-Lys-Leu-Gln-Leu-β-Lapachone (SL-11154)

To a solution of 486.8 mg (4.057×10$^{-4}$ mol) of morpholino-Ser(OBn)-Lys(Nε-Cl-Cbz)-Leu-Gln-Leu-β-Lapachone in 9 mL of MeOH/CHCl$_3$=1:9 was added 180.5 mg 10% Pd/C. Then two drops of HCl were added. The reaction mixture was placed under an atmosphere of H$_2$ (balloon) and stirred at room temperature for 15.5 hr. Removal of catalyst by filtration and evaporation of solvent afforded a light brown solid. The material was dissolved in 12 mL of MeOH/CHCl$_3$=1:9, and stirred at room temperature for 1 hr while bubbling air through the solution. Evaporation of solvent afforded an orange glassy solid. Column chromatography on silica gel with 20-30% MeOH in CHCl$_3$ yielded 52.8 mg (14%) of material as an orange solid. The material was further purified by prep HPLC: R$_f$=0.06 (20% MeOH in CHCl$_3$).

Figure 15:
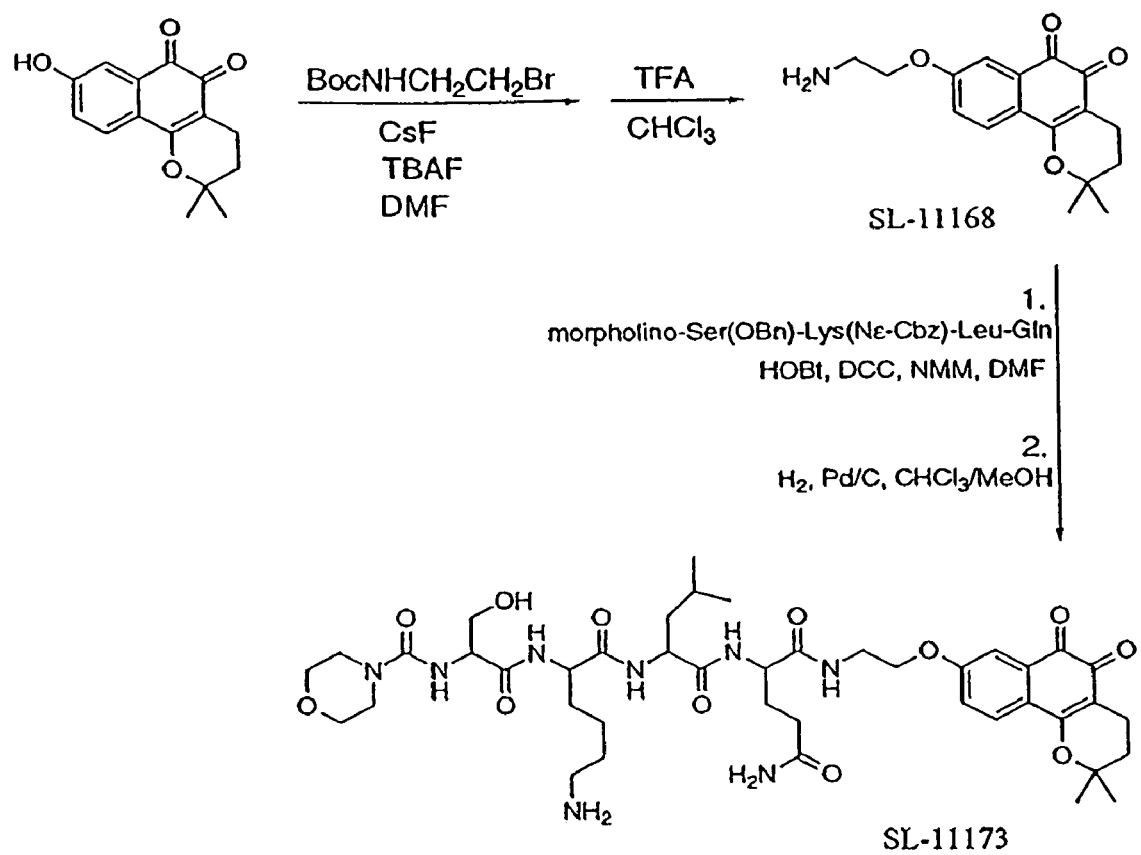
FIG. 15 depicts additional synthetic preparation of peptides conjugated to certain quinone compounds, including attachment of a linker group between the quinone and the peptide.

Synthesis of Morpholine-Ser-Lys-Leu-Gln-NHCH$_2$CH$_2$O-β-Lapachone (Sl-11173) (see FIG. 15)

8-(N-Boc-(2-Aminoethoxy))-β-Lapachone

To a solution of 507.1 mg (2.263 mmol) of N-boc-2-bromethylamine and 562.3 mg (2.177 mmol) of 8-hydroxy-β-Lapachone in 18 mL of DMF was added 727 mg (4.786 mmol) of CsF, followed by 2.2 mL of a solution of 1M TBAF in THF. The reaction mixture was stirred under N$_2$ at room temperature for 48 hr. Then the reaction mixture was partitioned between 100 mL of CHCl$_3$ and 75 mL of water plus 10 mL of 5% citric acid. The aqueous phase was extracted with CHCl$_3$ (5×40 mL). The CHCl$_3$ extracts were combined, dried with MgSO$_4$, and evaporated. Column chromatography on silica gel with 5% MeOH in CHCl$_3$ afforded 305.8 mg (35%) of quinone as a red-orange glassy solid; R$_f$=0.49 (5% MeOH in CHCl$_3$); $^1$H NMR (250 MHz, DMSO-d$_6$, TMS) δ 7.68 (d, J=8.6 Hz, 1H), 7.35 (d, J=2.7 Hz, 1H), 7.28 (dd, J=8.6, 2.7 Hz, 1H), 7.05 (br t, NH), 4.08 (t, J=5.6 Hz, 2H), 3.4-3.3 (m, 2H), 2.37 (t, J=6.5 Hz, 2H), 1.81 (t, J=6.5 Hz, 2H), 1.41 (s, 6H), 1.39 (s, 9H), $^{13}$C NMR (52 MHz, DMSO-d$_6$, TMS) δ 179.0, 177.8, 161.3, 160.3, 131.4, 125.6, 124.7, 120.5, 113.3, 110.3, 78.9, 77.8, 67.0, 30.8, 28.1, 26.2, 15.7.

8-(2-Aminoethoxy)-β-Lapachone (SL-11168)

To a solution of 219.8 mg (5.474×10$^{-4}$ mol) of 8-(N-Boc-(2aminoethyoxy))-β-lapachone in 6 mL of CHCl$_3$ was added 6 mL of TFA. The reaction mixture was stirred at room temperature for 20 min. The solvent was removed in vacuo. Column chromatography on silica gel with 20% MeOH in CHCl$_3$ afforded 210.7 mg (93%) of quinone (as the trifluoroacetate salt) as a red glassy solid: R$_f$=0.13 (10% MeOH in CHCl$_3$); $^1$H NMR (250 MHz, DMSO-d$_6$, TMS) δ 8.1-8.0 (v br s, NH), 7.74 (d, J=8.6 Hz, 1H), 7.45 (d, J=2.6 Hz, 1H), 7.34 (dd, J=8.6, 2.6 Hz, 1H), 4.4-4.2 (m, 2H), 3.3-3.2 (m, 2H), 2.38 (t, 6.5 Hz, 2H), 1.82 (t, J=6.5 Hz, 2H), 1.42 (s, 6H).

Morpholino-Ser(OBn)-Lys(Nε-Cbz)-Leu-Gln-NHCH$_2$CH$_2$O-β-Lapachone

To a solution of 210.7 mg (5.072×10$^{-4}$ mol) of NH$_2$CH$_2$CH$_2$O-β-lapachone-TFA salt an d 411.9 mg (5.072×10$^4$ mol) of morpholino-Ser(OBn)-Lys(Nε-Cbz)-Leu-Gln in 2.25 mL of DMF was added 82.4 mg (6.098×10$^{-4}$ mol) of 1-hydroxybenzotriazole. The mixture was cooled in an ice bath. Then 56 μL (5.093×10$^{-4}$ mol) of N-methylmorpholine were added, followed by 115.1 mg (5.578×10$^{-4}$ mol) of DCC. The reaction mixture was stirred in the ice bath for 45 min and at room temperature for 5 hr. The reaction mixture was then filtered and the filtrate diluted with CHCl$_3$. The filtrate was washed with 5% citric acid (4×30 mL), with saturated NaHCO$_3$ (3×40 mL), with saturated NaCl (40 mL), dried with MgSO$_4$, and evaporated to dryness. Purification by column chromatography on silica gel with 5% MeOH in CHCl$_3$ afforded 139.6 mg (25%) of peptide as a red-orange glassy solid: R$_f$=0.07 (5% MeOH in CHCl$_3$); 0.33 (10% MeOH in CHCl$_3$); $^1$H NMR (250 MHz, DMSO-d$_6$, TMS) δ 8.00 (br d, J=6 Hz, NH), 7.85 (br d, J=8 Hz, NH), 7.82 (br d, J=7 Hz, NH), 7.68 (d, J=8.6 Hz, 1H (quinone)), 7.4-7.2 (m, 12H (2 quinone+10 Ph)), 7.2-7.1 (m, NH), 6.75 (br s, NH), 6.60 (br d, J=7 Hz, NH), 4.99 (s, 2H), 4.48 (s, 2H), 4.4-4.3 (m, 1H), 4.3-4.0 (m, 5H), 3.7-3.6 (m, 2H), 3.6-3.4 (m, 6H), 3.35-3.25 (m, 4H), 3.0-2.9 (m, 2H), 2.4-2.3 (m, 2H), 2.1-2.0 (m, 2H), 1.9-1.4 (m, 13H), 1.40 (s, 6H), 0.81 (d, J=6.4 Hz, 3H), 0.77 (d, J=6.3 Hz, 3H).

Morpholino-Ser-Lys-Leu-Gln-NHCH$_2$CH$_2$O-β-Lapachone

To a solution of 133.1 mg (1.215×10$^{-4}$ mol) of morpholino-Ser(OBn)-Lys(Nε-Cbz)-Leu-Gln-NHCH$_2$CH$_2$O-β-lapachone in 45 mL MeOH plus 5 mL CHCl$_3$ was added 57.9 mg of 10% Pd/C. Then two drops of HCl were added. The reaction mixture was placed under an atmosphere of H$_2$ (balloon) and stirred at room temperature for 23 hr. Removal of catalyst by filtration and evaporation of solvent afforded a reddish-brown solid. The material was dissolved in 20 mL of MeOH and stirred at room temperature for 21 hr while bubbling air through the solution. Evaporation of solvent afforded 107.0 mg of a dark red glassy solid. The material was purified by prep HPLC to yield 55.1 mg (52%).

Figure 16:
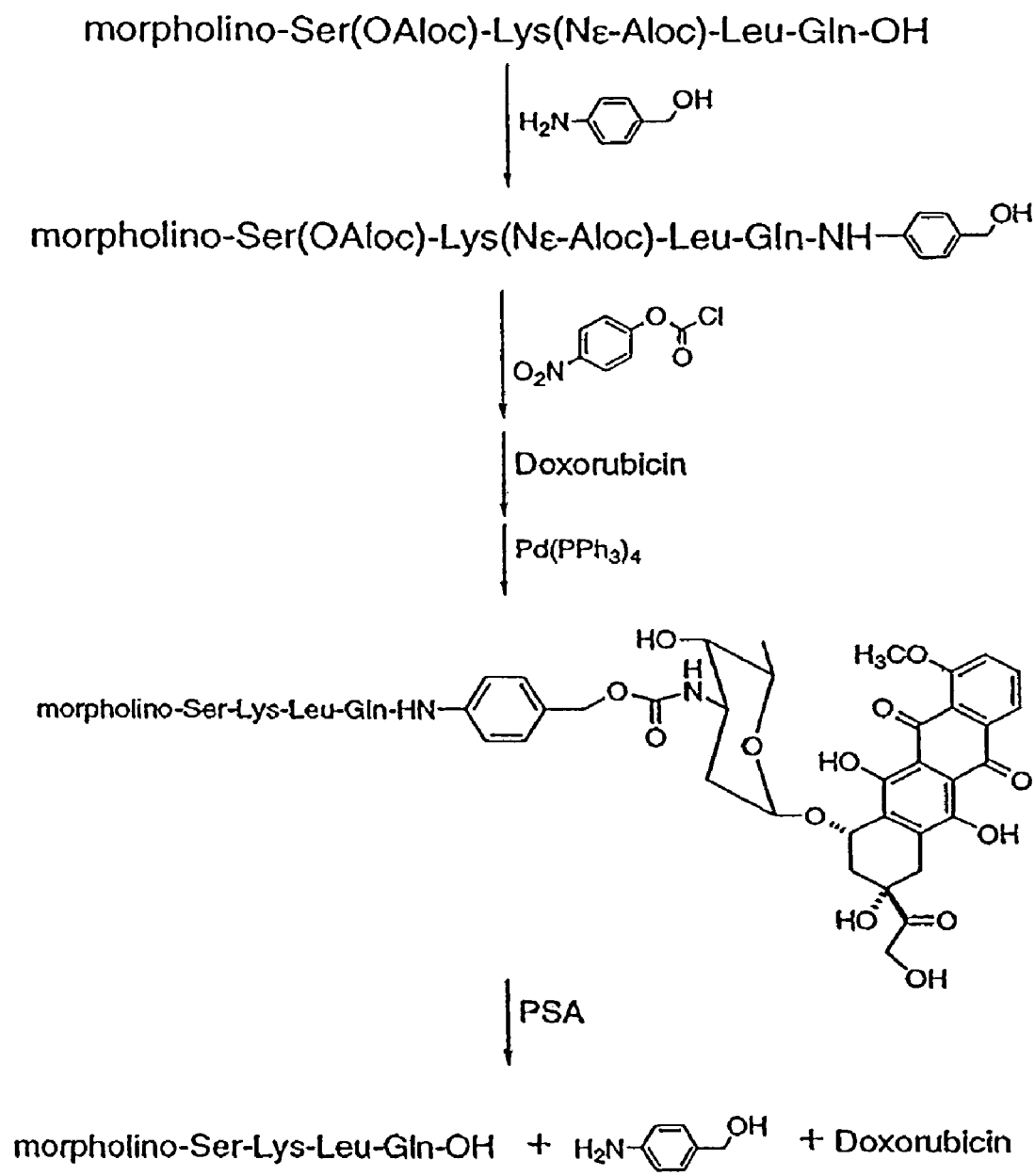
FIG. 16 depicts the attachment of doxorubicin to a peptide, including attachment of a linker group between doxorubicin and the peptide.

Synthesis of Morpholino-Ser-Lys-Leu-Gln-PABC-DOX (see FIG. 16)

Morpholino-Ser(OAloc) was prepared from Ser(OtBu)-OtBu. Reaction of Ser(OtBu)-OtBu with 4-morpholinecarbonyl chloride in pyridine yielded morpholino-Ser(OtBu)-OtBu. Morpholino-Ser(OtBu)-OtBu was hydrolyzed with TFA to yield morpholino-Ser. Esterification of morpholino-Ser with isobutylene in the presence of a catalytic amount of $H_2SO_4$ afforded morpholino-Ser-OtBu. Reaction of morpholino-Ser-OtBu with allyl 1-benzotriazolyl carbonate yielded morpholino-Ser(OAloc)-OtBu. Morpholino-Ser(OAloc)-OtBu was hydrolyzed with TFA in $CHCl_3$ (1:1) to yield morpholino-Ser(OAloc).

Preparation of the tetrapeptide was accomplished using standard procedures. Fmoc-Leu was coupled to Gln-OtBu with DCC in the presence of 1-hydroxybenzotriazole (HOBt) to give Fmoc-Leu-Gln-OtBu. Removal of the Fmoc group from Fmoc-Leu-Gln-OtBu with piperidine in $CH_2Cl_2$/DMF produced Leu-Gln-OtBu. Fmoc-Lys(Nε-Aloc) was coupled to Leu-Gln-OtBu with DCC in the presence of HOBt to give Fmoc-Lys(Nε-Aloc)-Leu-Gln-OtBu. Removal of the MFmoc group from Fmoc-Lys(Nε-Aloc)-Leu-Gln-OtBu with piperidine in DMF produced Lys(Nε-Aloc)-Leu-Gln-OtBu. Morpholino-Ser(OAloc) was coupled to Lys(Nε-Aloc)-Leu-Gln-OtBu with DCC in the presence of HOBt to give morpholino-Ser(OAloc)-Lys(Nε-Aloc)-Leu-Gln-OtBu. Hydrolysis of morpholino-Ser(OAloc)-Lys(Nε-Aloc)-Leu-Gln-OtBu with TFA in $CHCl_3$ (1:1) would give the tetrapeptide morpholino-Ser(OAloc)-Lys(Nε-Aloc)-Leu-Gln-OH. The tetrapeptide is condensed with PABC-DOX as described elsewhere. De Groot et al. (1999) *J. Med. Chem.* 42:5277-83. The amino acid side chains are deprotected as described. De Groot et al. (1999) *J. Med. Chem.* 42:5277-83. Morpholino-Ser-Lys-Leu-Gln-PABC-DOX has been used as a substrate of the enzyme PSA as shown in FIG. 16.

Figure 17:
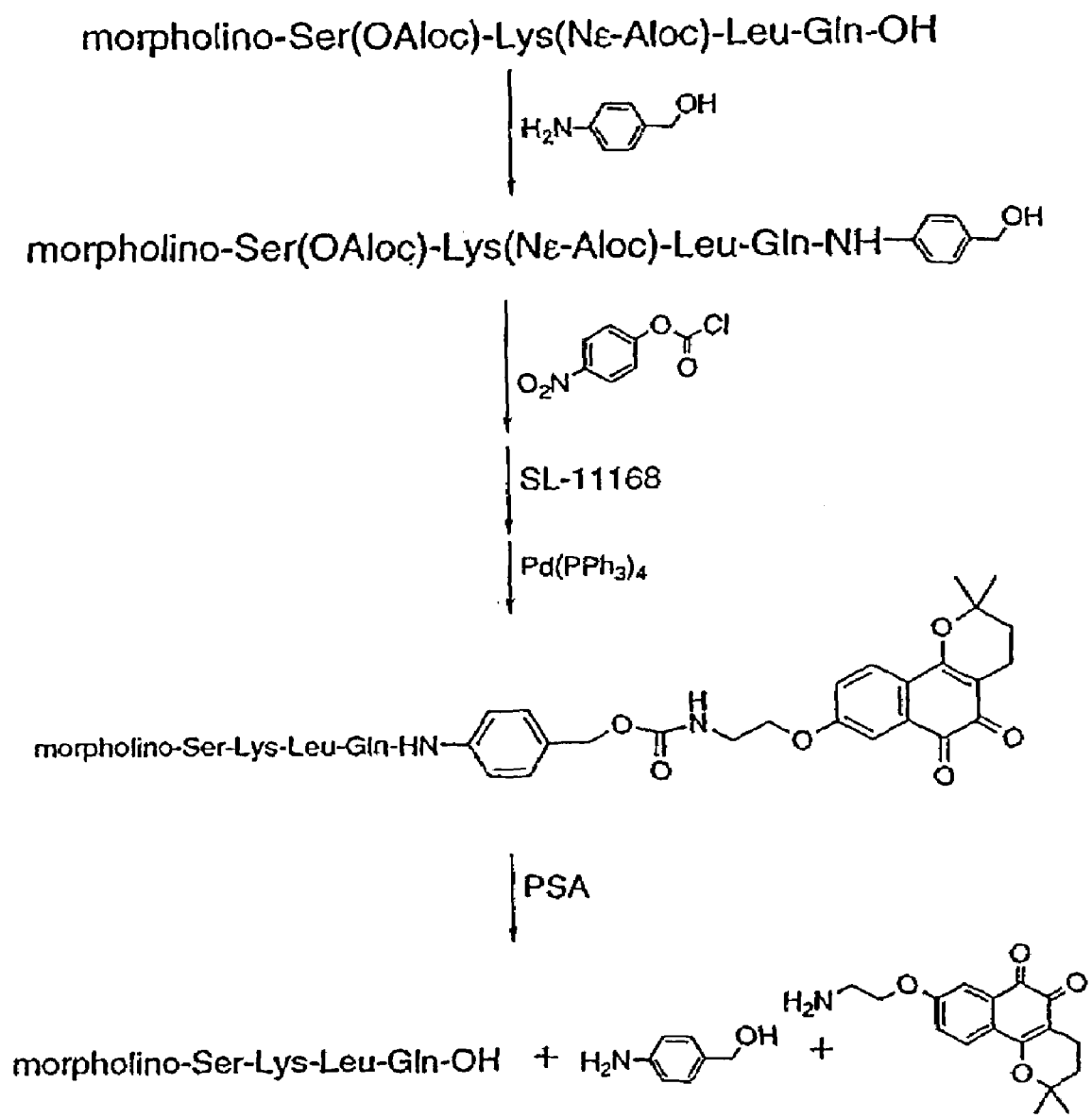
FIG. 17 depicts additional synthetic preparation of peptides conjugated to certain quinone compounds, including attachment of a linker group between the quinone and the peptide.

Synthesis of Morpholino-Ser-Lys-Leu-Gln-PABC-NHCH$_2$CH$_2$O-β-Lapachone (see FIG. 17)

Morpholino-Ser(OAloc) was prepared from SER(OtBu)-OtBu. Reaction of Ser(OtBu)-OtBu with 4-morpholineacarbonyl chloride in pyridine yielded morpholino-Ser(OtBu)-OtBu. Morpholino-Ser(OtBu)-OtBu was hydrolyzed with TFA to yield morpholino-Ser. Esterification of morpholino-Ser with isobutylene in the presence of a catalytic amount of $H_2SO_4$ afforded morpholino-Ser-OtBu. Reaction of morpholino-Ser-OtBu with allyl 1-benzotriazolyl carbonate yielded morpholino-Ser(OAloc)-OtBu. Morpholino-Ser(OAloc)-OtBu was hydrolyzed with TFA in $CHCl_3$ (1:1) to yield morpholino-Ser(OAloc).

Preparation of the tetrapeptide was accomplished using standard procedures. Fmoc-Leu was coupled to Gln-OtBu with DCC in the presence of 1-hydroxybenzotriazole (HOBt) to give Fmoc-Leu-Gln-OtBu. Removal of the Fmoc group from Fmoc-Leu-Gln-OtBu with piperidine in $CH_2Cl_2$/DMF produced Leu-Gln-OtBu. Fmoc-Lys(Nε-Aloc) was coupled to Leu-Gln-OtBu with DCC in the presence of HOBt to give Fmoc-Lys(Nε-Aloc)-Leu-Gln-OtBu. Removal of the Fmoc group from Fmoc-Lys(Nε-Aloc)-Leu-Gln-OtBu with piperidine in DMF produced Lys(Nε-Aloc)-Leu-Gln-OtBu. Morpholino-Ser(OAloc) was coupled to Lys(Nε-Aloc)-Leu-Gln-OtBu with DCC in the presence of HOBt to give morpholino-Ser(OAloc)-Lys(Nε-Aloc)-Leu-Gln-OtBu. Hydrolysis of morpholino-Ser(OAloc)-Lys(Nε-Aloc)-Leu-Gln-OtBu with TFA in $CHCl_3$ (1:1) would give the tetrapeptide morpholino-Ser(OAloc)-Lys(Nε-Aloc)-Leu-Gln-OH. The tetrapeptide is condensed with PABC-NHCH$_2$CH$_2$O-β-lapachone in an analogous manner as the condensation of the tetrapeptide with doxorubicin, described in De Groot et al. (1999) *J. Med. Chem.* 42:5277-83; the amino acid side chains are deprotected using the procedure described in that reference. Morpholino-Ser-Lys-Leu-Gln-PABC-NHCH$_2$CH$_2$O-β-lapachone is used as a substrate of the enzyme PSA as shown in FIG. 17.

Example 2

Cell Culture and Drug Testing Protocol

Cell Culture: The human lung adenocarcinoma cell line, A549, and human prostatic cancer cell line, DUPRO, were a gift from Dr. M. Eileen Dolan, University of Chicago, Department of Medicine. A549 was grown in Ham's F-12K medium (Fisher Scientific, Itasca, Ill.) supplemented with 10% fetal bovine serum and 2 mM L-glutamine. DUPRO was grown in RPMI-1640 supplemented with 10% fetal bovine serum. The human colon carcinoma cell line, HT29, and the human breast carcinoma cell line, MCF7, were obtained from the American Type Culture Collection, Rockville, Md. HT29 cells were grown in McCoy's 5A medium (Gibco, BRL, Gaithersburg, Md.) supplemented with 10% fetal bovine serum. MCF7 cells were grown in Richter's Improved Modified Eagle's medium supplemented with 10% fetal bovine serum and 2.2 g/L sodium bicarbonate. The human prostate adenocarcinoma cell lines, LNCAP, PC-3 and DU145, were gifts from Dr. George Wilding, University of Wisconsin Comprehensive Cancer Center and the Department of Medicine, and were grown in Dulbecco's Modified Eagle's medium supplemented with a 5% fetal bovine serum. The malignant glioma cell line, U251MG NCI was obtained from the brain tumor tissue bank at the University of California, San Francisco Department of Neurosurgery, and was grown in Dulbecco's Modified Eagle's medium supplemented with 10% fetal bovine serum. DUPRO, A549 and MCF7 cells were grown in 100 units/mL penicillin and 100 μg/mL streptomycin. HT29 and U251MG NCI cells were grown in 50 g/μL gentamycin. LNCAP, PC-3 and DU145 cells were maintained in 1% antibiotic antimycotic solution (Sigma, St. Louis, Mo.). All cell cultures were maintained at 37° C. in 5% $CO_2$/95% humidified air.

MTT assay. Exponentially growing monolayer cells were plated in 96 well plates at a density of 500 cells/well and allowed to grow for 24 h. Serially diluted drug solutions were added such that the final drug concentrations in the treatment media were between 0 and 35 μM. Cells were incubated with drug at either 4 hr or 72 hr. After 4 hr and 72 hr treatment, drugs were removed, fresh media (without) drug (100 uL) was added and cells were incubated for 6 days. After six days, 25 μL of a Dulbecco's phosphate-buffered saline solution containing 5 mg/mL of MTT (Thiazolyl blue) (Sigma) was added to each well and incubated for 4 h at 37° C. Then 100 μL of lysis buffer (20% sodium dodecyl sulfate, 50% N,N-dimethylformamide and 0.8% acetic acid, pH 4.7) was added to each well and incubated for an additional 22 h. A microplate reader (E max, Molecular Devices, Sunnyvale, Calif.) set at 570 nm was used to determine the optical density. Results were plotted as a ratio of the optical density in drug treated wells to the optical density in wells treated with vehicle alone. Plotting and estimation of $ID_{50}$ values were accomplished with manufacturer supplied software.

TABLE 1
ID$_{50}$ (μM) Values of Quinones in Various Cultured Human Prostate Tumor Cell Lines Determined by the MTT Assay
| No. | Structures of Quinones | ID$_{50}$ (μM) of different prostate cells | | |
|---|---|---|---|---|
| | | PC-3 | DUPRO | DU145 LNCAP |
| SL-11051 |  | 17.11 | 19.3 | 11.16 |
| SL-11059 | 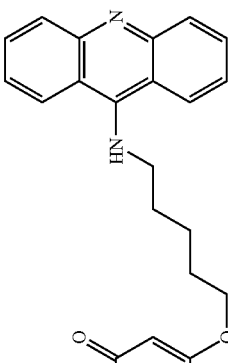 | 4.3 | | |
| SL-11062 | 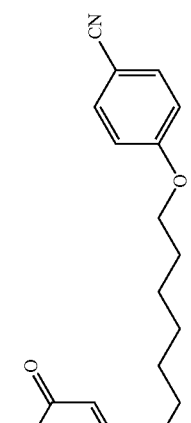 | 1.71 | | |

TABLE 1-continued
ID$_{50}$ (μM) Values of Quinones in Various Cultured Human Prostate Tumor Cell Lines Determined by the MTT Assay
| No. | Structures of Quinones | ID$_{50}$ (μM) of different prostate cells | | |
|---|---|---|---|---|
| | | PC-3 | DUPRO | DU145 LNCAP |
| SL-11064 | 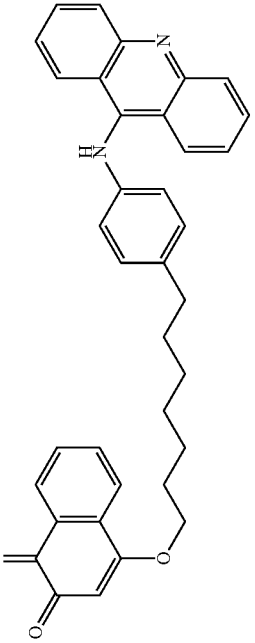 | 0.7 | 2.2 | 0.13 |
| SL-11065 | 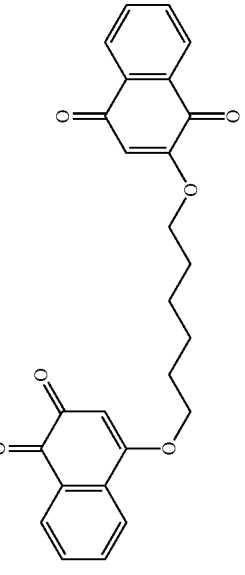 | 1.4 | | |
| SL-11066 | 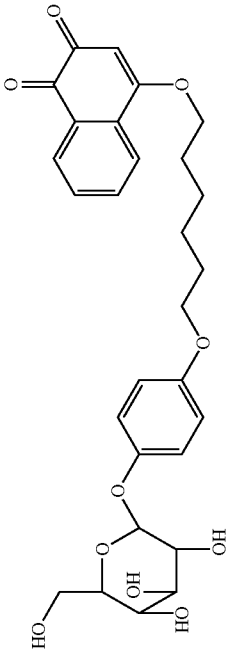 | >31.25 | | |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | | |
|---|---|---|---|---|---|
| | | PC-3 | DUPRO | DU145 | LNCAP |
| SL-11067 | | 0.25 | | | |
| SL-11068 | | 1.5 | | | |
| SL-11074 | | 4.6 | | | |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | | |
|---|---|---|---|---|---|
| | | PC-3 | DUPRO | DU145 | LNCAP |
| SL-11075 | | 2.0 | | | |
| SL-11076 | | 1.8 | | | |
| SL-11078 | | 18.4 | | | |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | | |
|---|---|---|---|---|---|
| | | PC-3 | DUPRO | DU145 | LNCAP |
| SL-11079 | | 22.5 | | | |
| SL-11080 | | 7.3 | | | |
| SL-11081 | | 5.6 | | | |

TABLE 1-continued

ID$_{50}$ (µM) Values of Quinones in Various Cultured Human Prostate Tumor Cell Lines Determined by the MTT Assay

| No. | Structures of Quinones | ID$_{50}$ (µM) of different prostate cells | | | |
|---|---|---|---|---|---|
| | | PC-3 | DUPRO | DU145 | LNCAP |
| SL-11082 | | 5.4 | | | |
| SL-11083 | | 5.2 | | | |
| SL-11084 | | 5.9 | | | |

TABLE 1-continued
ID$_{50}$ (μM) Values of Quinones in Various Cultured Human Prostate Tumor Cell Lines Determined by the MTT Assay
| No. | Structures of Quinones | ID$_{50}$ (μM) of different prostate cells | | |
|---|---|---|---|---|
| | | PC-3 | DUPRO | DU145 | LNCAP |
| SL-11085 | 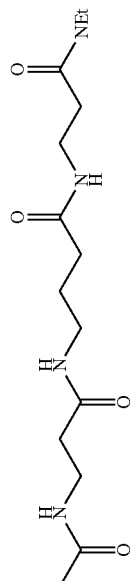 | >31.25 | | | |
| SL-11087 | 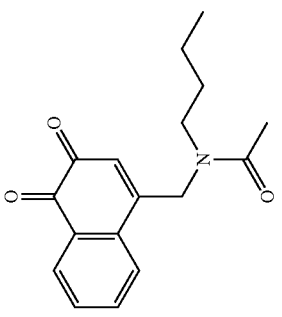 | 2.4 | | | |
| SL-11088 | 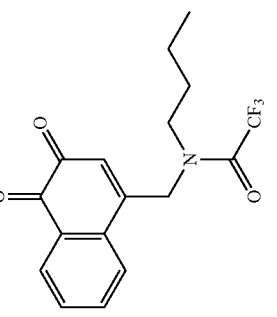 | >31.25 | | | |

TABLE 1-continued
ID$_{50}$ (μM) Values of Quinones in Various Cultured Human Prostate Tumor Cell Lines Determined by the MTT Assay
| No. | Structures of Quinones | ID$_{50}$ (μM) of different prostate cells | | | |
|---|---|---|---|---|---|
| | | PC-3 | DUPRO | DU145 | LNCAP |
| SL-11089 | 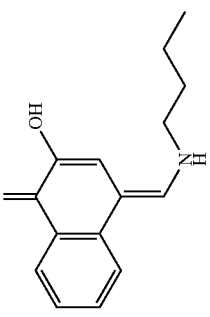 | 11.03 | | | |
| SL-11095 | 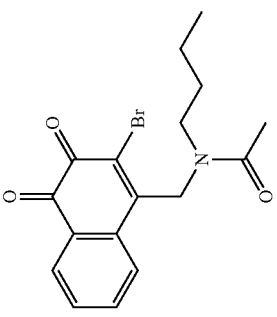 | 4.2 | | | |
| SL-11096 | 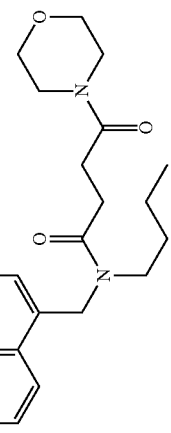 | 3.6 | | | |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | | |
|---|---|---|---|---|---|
| | | PC-3 | DUPRO | DU145 | LNCAP |
| SL-11106 | | >31.25 | | | |
| SL-11107 | | 4.3 | | >31.25 | 17.2 |
| SL-11112 | | >31.25 | | >27.9 | 22.9 |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | |
|---|---|---|---|---|
| | | PC-3 | DUPRO | DU145 | LNCAP |
| SL-11113 | | 27.9 | >31.25 | 29.2 |
| SL-11120 | | 6.4 | 13.1 | 3.8 |

TABLE 1-continued

ID$_{50}$ (μM) Values of Quinones in Various Cultured Human Prostate Tumor Cell Lines Determined by the MTT Assay

| No. | Structures of Quinones | ID$_{50}$ (μM) of different prostate cells | | |
|---|---|---|---|---|
| | | PC-3 | DUPRO | DU145 LNCAP |
| SL-11125 | | 5.9 | 7.9 | 0.13 |
| SL-11145 | | 1.97 (4 hr) 0.51 (6 days) | | 0.7 (4 hr) 0.8 (6 days) |

TABLE 1-continued
ID$_{50}$ (μM) Values of Quinones in Various Cultured Human Prostate Tumor Cell Lines Determined by the MTT Assay
| No. | Structures of Quinones | ID$_{50}$ (μM) of different prostate cells | | |
|---|---|---|---|---|
| | | PC-3 | DUPRO | DU145 LNCAP |
| SL-11147 | 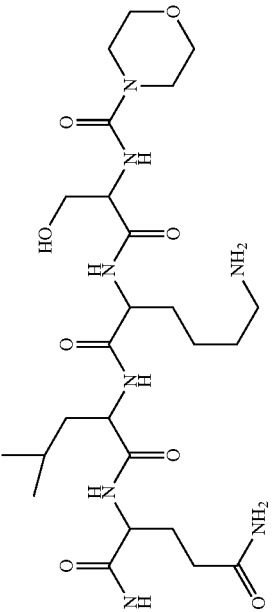 | 6.3 (4 hr) 1.24 (72 hr) | | 28.08 (4 hr) 2.01 (72 hr) |
| SL-11148 | 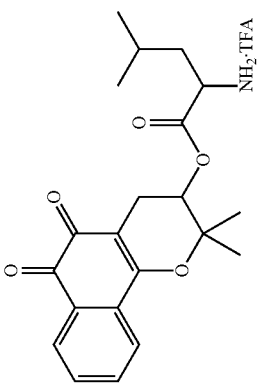 | 6.3 | | 1.84 |

TABLE 2

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11051 | | 17.23 | 20.02 | | |
| SL-11052 | | 26.88 | | | |
| SL-11053 | | 7.39 | 2.8 | | |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11054 | | >31.25 | >31.25 | | |
| SL-11056 | | >31.25 | >31.25 | >31.25 | >31.25 |
| SL-11059 | | 15.0 | 10.12 | | |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11060 | | >31.25 | >31.25 | 17.23 | >31.25 |
| SL-11062 | | 18.64 | | | |
| SL-11064 | | 9.3 | | | |

TABLE 2-continued
ID$_{50}$ (μM) Values of Quinones in Various Cultured Human Tumor Cell Lines Determined by the MTT Assay
| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11065 | | 2.13 | | | |
| SL-11066 | | >31.25 | | | |
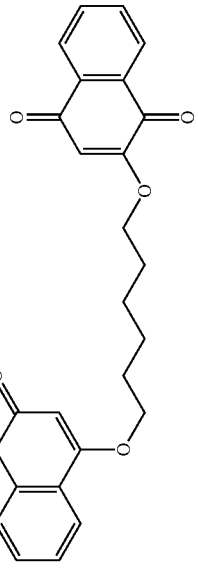

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11067 | | >31.25 | 0.53 | | |
| SL-11068 | | 24.0 | | | |

TABLE 2-continued
ID$_{50}$ (μM) Values of Quinones in Various Cultured Human Tumor Cell Lines Determined by the MTT Assay
| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11074 |  | | | | |
| SL-11075 |  | | | | |
| SL-11076 |  | 1.8 | 1.7 | | 10.24 |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11078 | | 18.9 | 19.3 | 30.85 | |
| SL-11079 | | | | | |
| SL-11080 | | | | | |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11081 | | | | | |
| SL-11082 | | | | | |
| SL-11083 | | | | | |

TABLE 2-continued

ID$_{50}$ (µM) Values of Quinones in Various Cultured Human Tumor Cell Lines Determined by the MTT Assay

| No. | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11084 | | | | | |
| SL-11085 | | | | | |
| SL-11087 | | 19.8 | 6.05 | 4.0 | |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11088 | | >31.25 | >31.25 | >31.25 | |
| SL-11089 | | | | >31.25 | |
| SL-11095 | | >31.25 | 22.1 | 20.6 | |

TABLE 2-continued

ID$_{50}$ (µM) Values of Quinones in Various Cultured Human Tumor Cell Lines Determined by the MTT Assay

| No. | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11096 | | 17.4 | 3.4 | 3.8 | |
| SL-11106 | | >31.25 | | | |
| SL-11107 | | >31.25 | | | |

TABLE 2-continued

ID$_{50}$ (µM) Values of Quinones in Various Cultured Human Tumor Cell Lines Determined by the MTT Assay

| No. | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11112 | | | | | |
| SL-11113 | | | | | |

TABLE 2-continued

ID$_{50}$ (μM) Values of Quinones in Various Cultured Human Tumor Cell Lines Determined by the MTT Assay

| No. | Structures of Quinones | ID$_{50}$ (μM) of different Tumor cells | | | |
|---|---|---|---|---|---|
| | | Lung A549 | Colon HT-29 | Breast MCF7 | Brain U251-MG |
| SL-11120 | | 26.7 | 20.9 | 4.1 | |
| SL-11125 | | 27.97 | 5.7 | 5.1 | |

TABLE 2-continued
ID$_{50}$ (μM) Values of Quinones in Various Cultured Human Tumor Cell Lines Determined by the MTT Assay
| No. | Structures of Quinones | ID$_{50}$ (μM) of different Tumor cells | | | | |
|---|---|---|---|---|---|---|
| | | Lung A549 | Colon HT-29 | Breast MCF7 | Brain U251-MG | |
| SL-11145 | 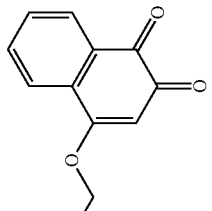 | | 2.4 (4hr) 1.0 (6 days) | | | |
| SL-11147 | 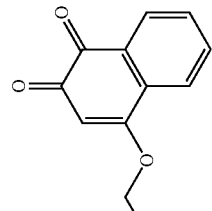 | | | | | |

TABLE 2-continued

ID$_{50}$ (µM) Values of Quinones in Various Cultured Human Tumor Cell Lines Determined by the MTT Assay

| No. | Structures of Quinones | ID$_{50}$ (µM) of different Tumor cells | | | |
|---|---|---|---|---|---|
| | | Lung A549 | Colon HT-29 | Breast MCF7 | Brain U251-MG |
| SL-11148 | (structure: 2,2-dimethyl-3,4-dihydro-2H-benzo[g]chromene-5,10-dione with 3-O-leucinyl ester, NH$_2$·TFA) | | | | |

TABLE 3

ID$_{50}$ (μM) Value(s) of Non-Quinone Structure in A Cultured Human Prostate Tumor Cell Line Determined by the MTT Assay

| No. | Structures of Compound | ID$_{50}$ (μM) of different prostate cells | | | |
|---|---|---|---|---|---|
| | | PC-3 | DUPRO | DU145 | LNCAP |
| SL-11063 | 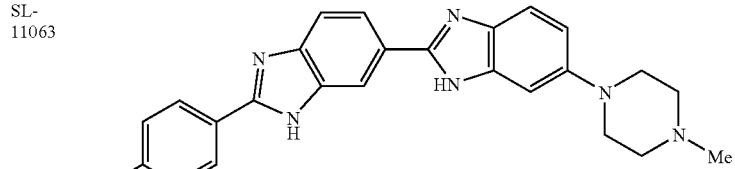 | >31.25 | | | |

TABLE 4

ID$_{50}$ (μM) Values of Selected Non-Quinone Compounds in Various Cultured Human Tumor Cell Lines Determined by the MTT Assay

| No. | Structures of Non-Quinone Compounds | ID$_{50}$ (μM) of different Tumor cells | | | |
|---|---|---|---|---|---|
| | | Lung A549 | Colon HT-29 | Breast MCF7 | Brain U251-MG |
| SL-11055 | 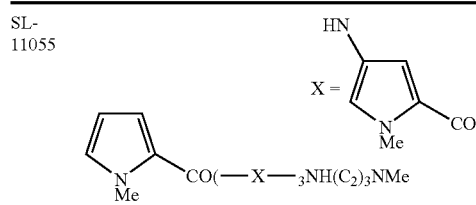 | >31.25 | >31.25 | >31.25 | >31.25 |
| SL-11058 | 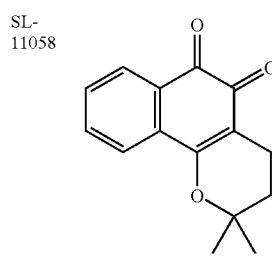 | | | | >31.25 |
| SL-11063 | 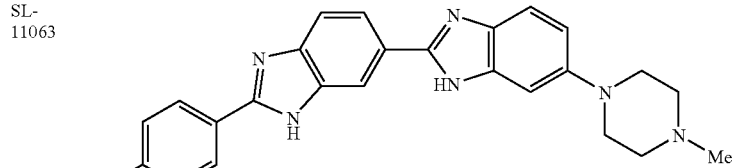 | >31.25 | | | |

Table 5 lists additional quinones and quinone derivatives which are useful in the invention, either as therapeutics or, in the case of quinones which are not already covalently linked to or derivatized with peptides, as therapeutics in conjunction with peptides.

TABLE 5
| No. | Name and/or Structure |
|---|---|
| SL-11001 | β-lapachone 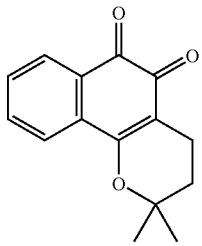 |
| SL-11002 | 3-hydroxy-β-lapachone 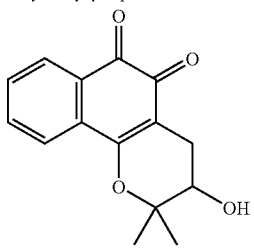 |
| SL-11003 | 3-malonyloxy-β-lapachone 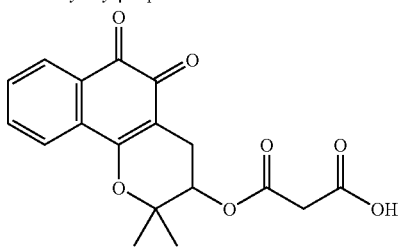 |
| SL-11004 | 3-(pyrrolidinosuccinoyl)-β-lapachone 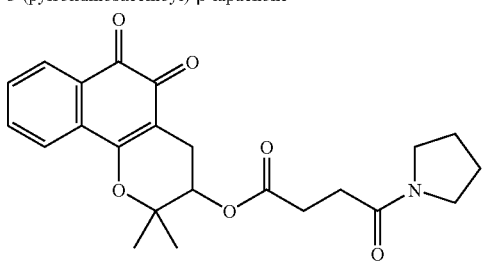 |
| SL-11005 | 3-(morpholinosuccinoyl)-β-lapachone 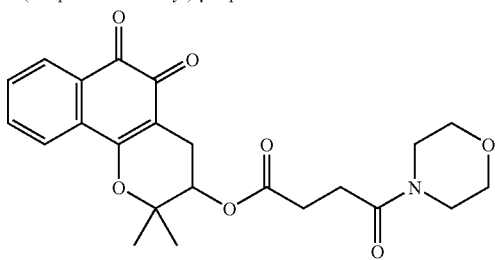 |

TABLE 5-continued
| No. | Name and/or Structure |
| --- | --- |
| SL-11006 | 3-(β-alanyloxy)-β-lapachone hydrobromide 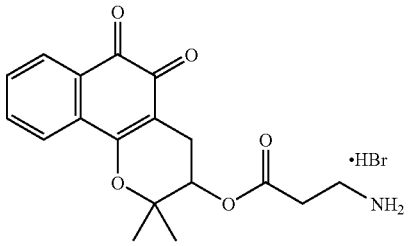 |
| SL-11007 | 3-(N-ethyl-β-alanyloxy)-β-lapachone hydrobromide 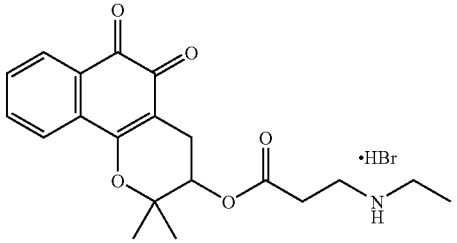 |
| SL-11008 | 3,3-dinordunnione 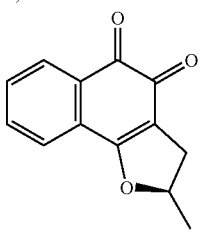 |
| SL-11009 | 3-nordunnione 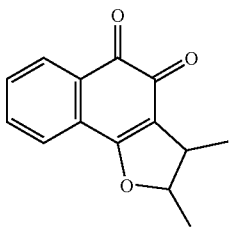 |
| SL-11010 | dunnione 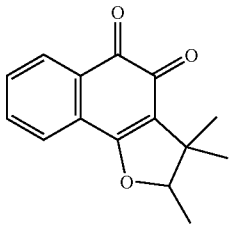 |
| SL-11011 | naphthoquinonefuran 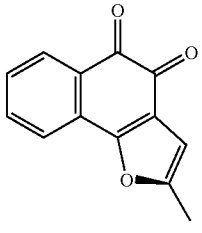 |

TABLE 5-continued
| No. | Name and/or Structure |
|---|---|
| SL-11012 | β-norlapachone 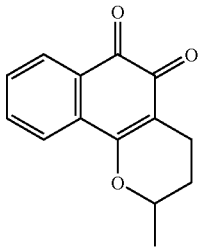 |
| SL-11013 | 4-pentoxy-1,2-naphthoquinone 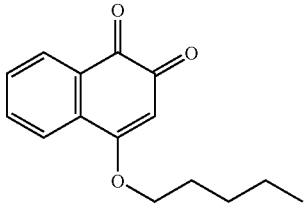 |
| SL-11014 | 4-isobutoxy-1,2-naphthoquinone 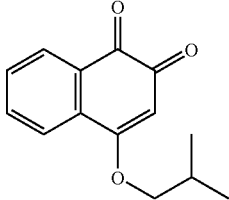 |
| SL-11015 | 4-isoamyloxy-1,2-naphthoquinone 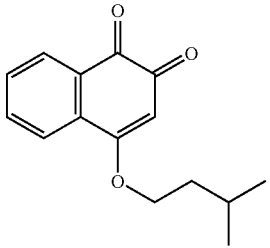 |
| SL-11016 | 4-isopropoxy-1,2-naphthoquinone 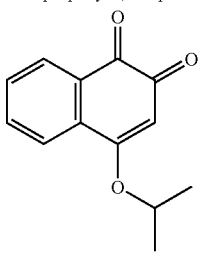 |
| SL-11017 | 4-(2butenyloxy)- -1,2-naphthoquinone 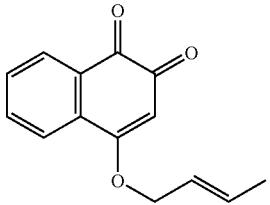 |

TABLE 5-continued
| No. | Name and/or Structure |
|---|---|
| SL-11018 | 4-benzyloxy-1,2-naphthoquinone 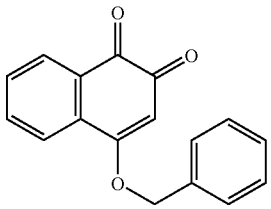 |
| SL-11019 | 4-cyclohexylmethoxy-1,2-naphthoquinone 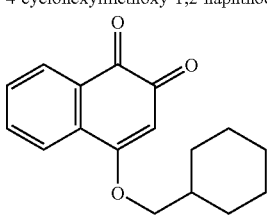 |
| SL-11020 | 4-(γ-ethylalloxy)-1,2-naphthoquinone 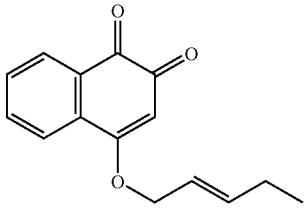 |
| SL-11021 | 4-heptoxy-1,2-naphthoquinone 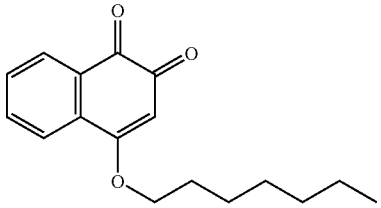 |
| SL-11022 | 4-pentanethio-1,2-naphthoquinone 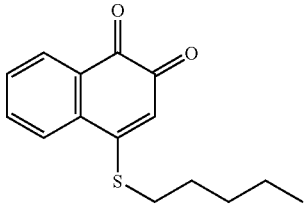 |
| SL-11023 | 4-[2-(dimthylamino)ethylamino-1,2-naphthoquinone 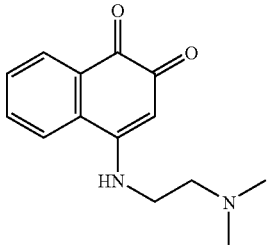 |

TABLE 5-continued
| No. | Name and/or Structure |
|---|---|
| SL-11024 | 4-methoxy-1,2-naphthoquinone 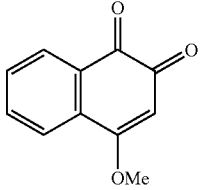 |
| SL-11025 | 8-methoxy-3-hydroxy-β-lapachone 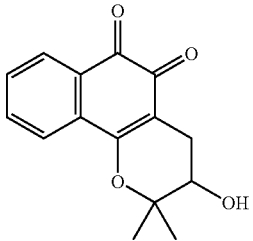 |
| SL-11026 | 4-pentylamino-1,2-naphthoquinone 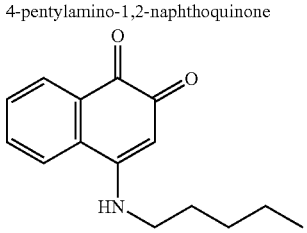 |
| SL-11031 | 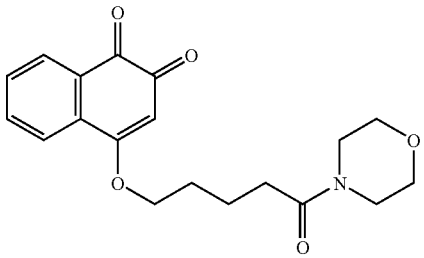 |
| SL-11039 | 4-ethoxy-1,2-naphthoquinone 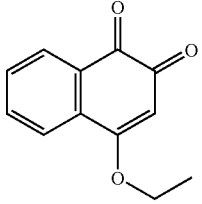 |
| SL-11041 | 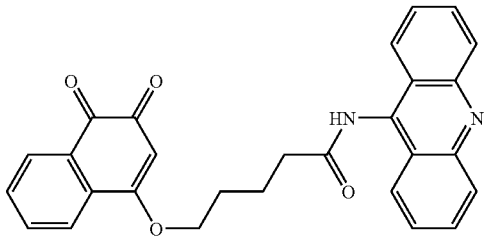 |

TABLE 5-continued

| No. | Name and/or Structure |
|---|---|
| SL-11042 | 4-hexyloxy-1,2-naphthoquinone |
| SL-11045 | 5-oxo-4'-(1',2'-naphthoquinone)valeric acid |
| SL-11046 | 4-(5'-aminopentoxy)-1,2-naphthoquinone •TFA salt |
| SL-11049 | 4-(3'-cyclohexylpropyloxy)-1,2-naphthoquinone |
| SL-11057 | O(CH$_2$)$_n$CO(—X—)$_3$NH(CH$_2$)$_3$NMe$_2$·HCl, n = 4 |
| SL-11142 | |

115 116
TABLE 5-continued
| No. | Name and/or Structure |
|---|---|
| SL-11146 | 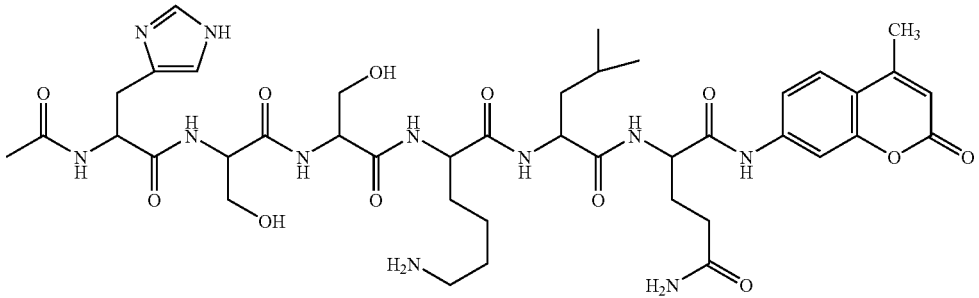 |
| SL-11151 | 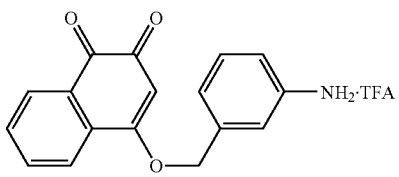 |
| SL-11152 | 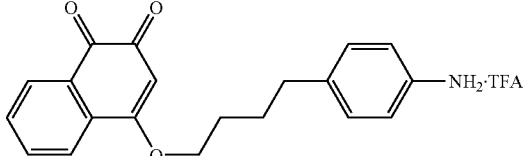 |
| SL-11153 | 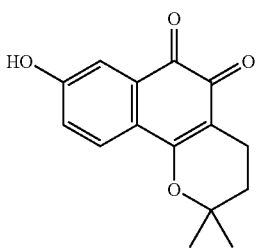 |
| SL-11154 | 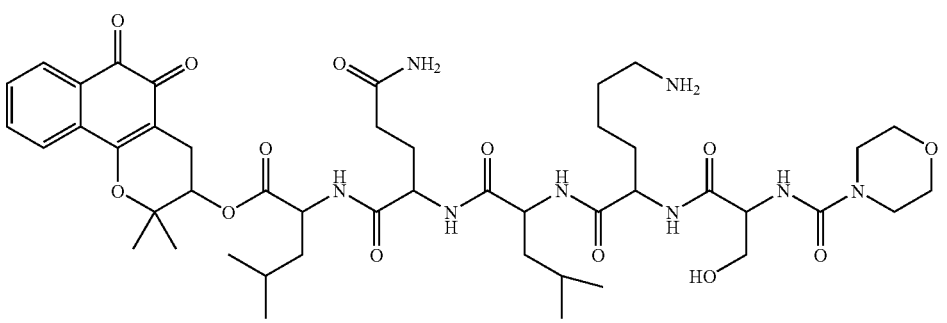 |
| SL-11168 | 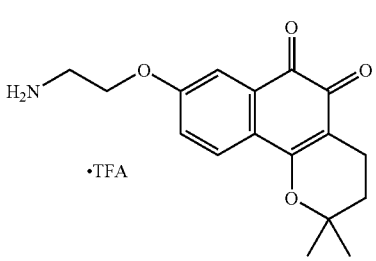 |

TABLE 5-continued
| No. | Name and/or Structure |
|---|---|
| SL-11173 | 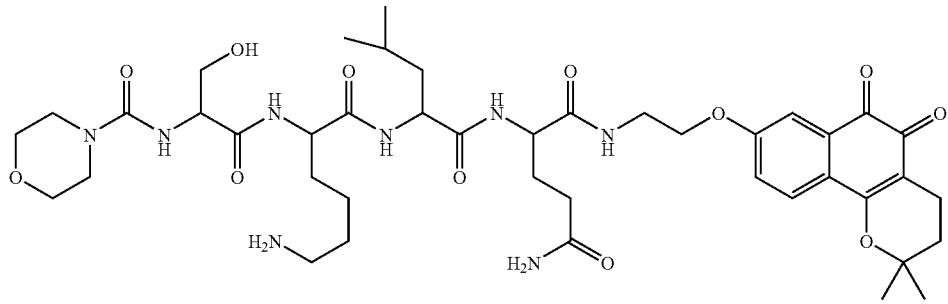 |
| SL-11185 | 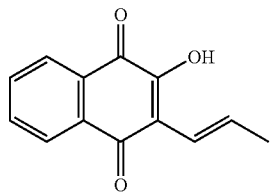 |
| SL-11186 | 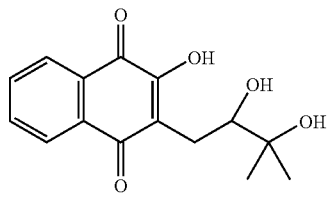 |
| SL-11187 | 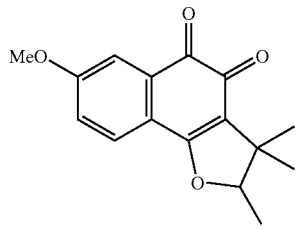 |
| SL-11188 | 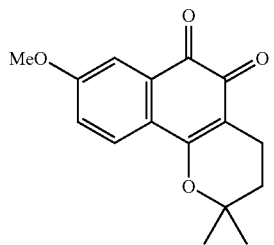 |
| SL-11189 | 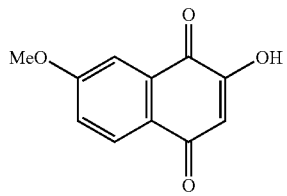 |

TABLE 5-continued

| No. | Name and/or Structure |
|---|---|
| SL-11190 | 4,7-dichloro-5,6-dihydroxy-1,3-diimino-isoindoline |
| SL-11191 | 7-methoxy-2-hydroxy-3-(3-methyl-2-butenyl)-1,4-naphthoquinone |
| SL-11192 | 4,5-dichloro-3-(4-phthalimidobutyl)-6-(3-phthalimidopropoxy)phthalonitrile |
| SL-11193 | 4,5-dichloro-3,6-dihydroxyphthalonitrile |
| SL-11194 | 2-allyloxy-1,4-naphthoquinone |
| SL-11195 | 2-(3-methyl-2-butenyloxy)-1,4-naphthoquinone |

TABLE 5-continued

| No. | Name and/or Structure |
|---|---|
| SL-11196 | 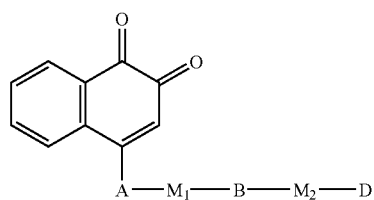 |
| SL-11205 | |

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention, which is delineated by the appended claims.

What is claimed is:

1. A compound of the formula:

A—$M_1$—B—$M_2$—D wherein A is selected from the group consisting of —O— and —$CH_2$—;

wherein $M_1$ is selected from the group consisting of a single bond and $C_1$-$C_8$ alkyl, $C_1$-$C_8$ branched alkyl, $C_3$-$C_8$ cycloalkyl, and $C_3$-$C_8$ cycloaryl;

wherein B is selected from the group consisting of —$CH_2$—, —O—, —C(=O)—O—; —O—C(=O)—, and —N($R_1$)—;

wherein $R_1$ is selected from the group consisting of —H, $C_1$-$C_8$ alkyl, $C_1$-$C_8$ branched alkyl, $C_3$-$C_8$ cycloalkyl, and $C_3$-$C_8$ cycloaryl;

wherein $M_2$ is selected from the group consisting of a single bond and $C_1$-$C_8$ alkyl, $C_1$-$C_8$ branched alkyl, $C_3$-$C_8$ cycloalkyl, and $C_3$-$C_8$ cycloaryl;

wherein D is selected from the group consisting of —OH, —N($R_7$)($R_8$),

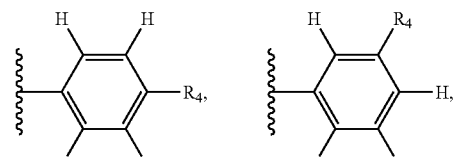

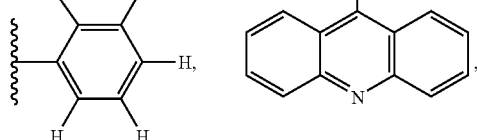

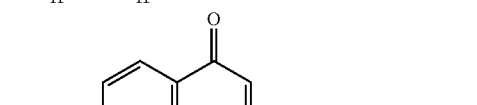

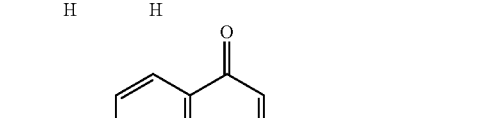

wherein $R_4$ is selected from the group consisting of —H, $C_1$-$C_8$ alkyl, $C_1$-$C_8$ branched alkyl, $C_3$-$C_8$ cycloalkyl, $C_3$-$C_8$ cycloaryl, —N($R_9$)($R_{10}$), and —CN; and wherein $R_7$, $R_8$, $R_9$ and $R_{10}$ are independently selected from the group consisting of —H, $C_1$-$C_8$ alkyl, $C_1$-$C_8$ branched alkyl, $C_3$-$C_8$ cycloalkyl, $C_3$-$C_8$ cycloaryl, and

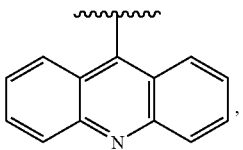

or a salt, stereoisomer or tautomer thereof.

2. A compound according to the formula

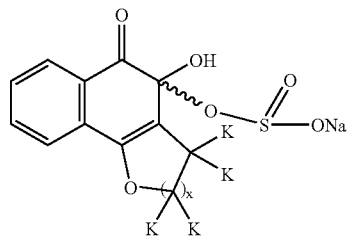

wherein x is an integer between 1 and 2;

and each K is independently selected from the group consisting of H, $C_1$-$C_8$ alkyl, $C_1$-$C_8$ alkenyl, $C_1$-$C_8$ alkanol, $C_1$-$C_8$ alkoxy,

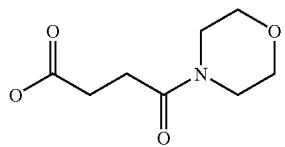

and where zero or two, but no more than two, vicinal K's in the molecule represent single electrons which form a pi bond, thus forming a double bond together with the existing sigma bond between the two adjacent carbons bearing the two vicinal K's, or a salt, stereoisomer or tautomer thereof.

3. A compound of the formula

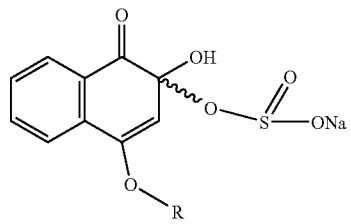

wherein R is selected from the group consisting of $C_1$-$C_8$ alkyl, $C_1$-$C_8$ cycloalkyl, $C_3$-$C_8$ cycloaryl, $C_1$-$C_8$ branched alkyl, and $C_1$-$C_8$ alkanol, or a salt, stereoisomer or tautomer thereof.

4. A compound of the formula

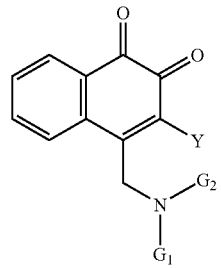

wherein Y is selected from the group consisting of —H, —F, —Br, —Cl, and —I; and wherein $G_1$ and $G_2$ are independently selected from the group consisting of H, $C_1$-$C_8$ alkyl,

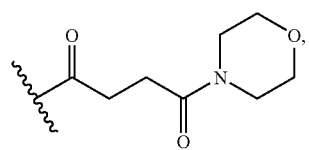

and —C(=O)—$CH_nX_{3-n}$, where n is an integer from 0 to 3 and X is selected from the group consisting of F, Cl, Br, and I, or a salt, stereoisomer or tautomer thereof.

5. A compound of the formula

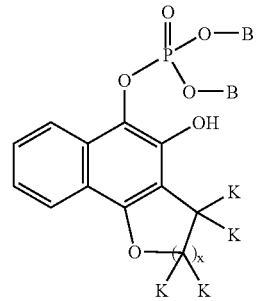

wherein x is an integer between 1 and 2;

each B is independently selected from the group consisting of H, $C_1$-$C_8$ alkyl, $C_3$-$C_8$ cycloalkyl, $C_3$-$C_8$ cycloaryl, $C_1$-$C_8$ alkyl-$C_3$-$C_8$ cycloalkyl, and $C_1$-$C_8$ alkyl-$C_3$-$C_8$ cycloaryl;

and each K is independently selected from the group consisting of H, OH, $C_1$-$C_8$ alkyl, $C_1$-$C_8$ alkenyl, $C_1$-$C_8$ alkanol, $C_1$-$C_8$ alkoxy, and where zero or two, but no more than two, vicinal K's in the molecule represent single electrons which form a pi bond, thus forming a double bond together with the existing sigma bond between the two adjacent carbons bearing the two vicinal K's, or a salt, stereoisomer or tautomer thereof.

6. A compound of the formula

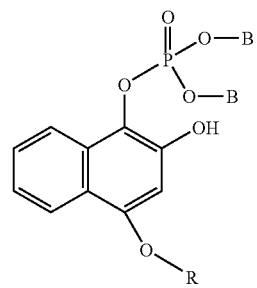

wherein each B is independently selected from the group consisting of H, $C_1$-$C_8$ alkyl, $C_3$-$C_8$ cycloalkyl, $C_3$-$C_8$ cycloaryl, $C_1$-$C_8$ alkyl-$C_3$-$C_8$ cycloalkyl, and $C_1$-$C_8$ alkyl-$C_3$-$C_8$ cycloaryl; and wherein R is selected from the group consisting of $C_1$-$C_8$ alkyl and $C_1$-$C_8$ alkanol, or a salt, stereoisomer or tautomer thereof.

7. A compound of the formula

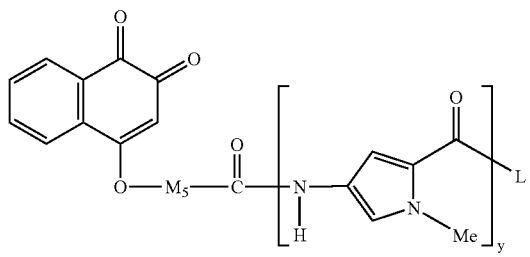

where $M_5$ is $C_1$-$C_8$ alkyl, y is an integer from 1 to 6, and L is selected from the group consisting of —O—$K_1$ or —N($K_1K_2$);

where $K_1$ and $K_2$ are independently selected from the group consisting of H, $C_1$-$C_8$ alkyl, $C_1$-$C_8$ alkyl-COOH, $C_1$-$C_8$ alkyl-COOH, $C_1$-$C_8$ alkyl, $C_1$-$C_8$ alkyl-N($G_1G_2$), and $C_1$-$C_8$ alkyl-N($G_3$)-$C_1$-$C_8$ alkyl-N ($G_4G_5$); and wherein each of $G_1$, $G_2$, $G_3$, $G_4$, and $G_5$ is independently selected from the group consisting of H and $C_1$-$C_8$ alkyl, or a salt, stereoisomer or tautomer thereof.

8. A compound of the formula:

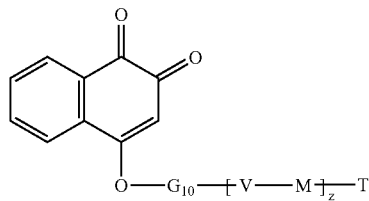

where z is an integer between one and ten; $G_{10}$ is selected from the group consisting of $C_1$-$C_8$ alkyl; each M is independently selected from the group consisting of $C_1$-$C_8$ alkyl; V is selected from the group consisting of —C(=O)—N— and —N—(C=O)—; and T is selected from the group consisting of —COOM$_8$ and —CONM$_9$M$_{10}$, where each of $M_8$, $M_9$ and $M_{10}$ are independently selected from the group consisting of H and $C_1$-$C_8$ alkyl, or a salt, stereoisomer or tautomer thereof.

9. A compound of the formula

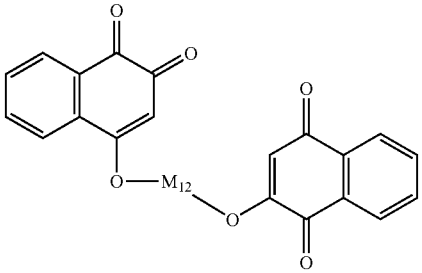

where $M_{12}$ is selected from the group consisting of $C_1$-$C_8$ alkyl, or a salt, stereoisomer or tautomer thereof.

10. A compound of the formula

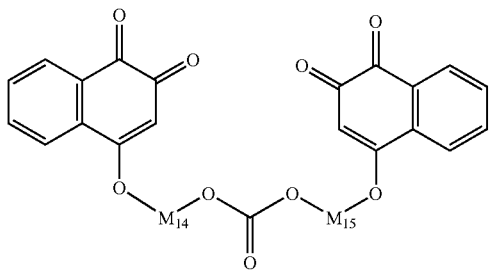

where $M_{14}$ and $M_{15}$ are independently selected from the group consisting of $C_1$-$C_8$ alkyl, or a salt, stereoisomer or tautomer thereof, with the proviso that the compound is not

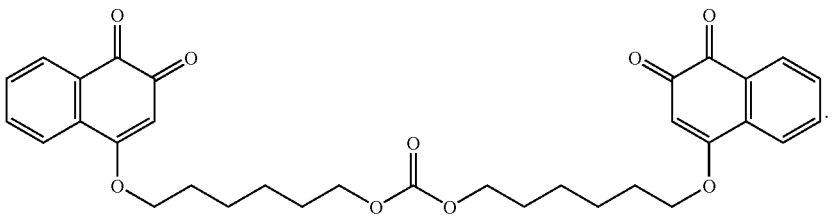

11. A compound of the formula

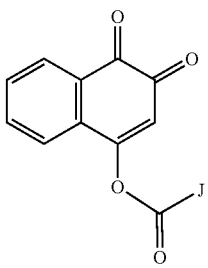

where J is selected from the group consisting of $C_1$-$C_8$ alkyl, $C_1$-$C_8$ cycloalkyl, $C_3$-$C_8$ cycloaryl, and $C_1$-$C_8$ branched alkyl, or a salt, stereoisomer or tautomer thereof.

12. A compound of the formula

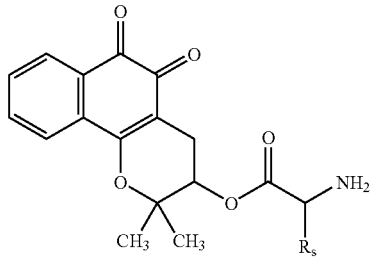

where $R_s$ is the side chain of a naturally-occurring amino acid, attached in S or R configuration, or a salt, stereoisomer or tautomer thereof.

13. A compound of the formula

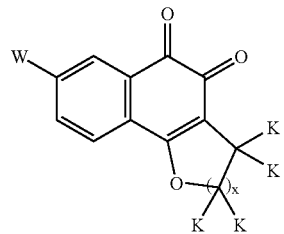

wherein x is an integer between 1 and 2;

W is selected from —OH, —O—$C_1$-$C_8$ alkyl, —O—$C_1$-$C_8$ alkyl-NH$_2$, and —O—$C_1$-$C_8$ -alkyl-NH—S, wherein S is a single amino acid or a peptide of two or more amino acids;

and each K is independently selected from the group consisting of H, OH, $C_1$-$C_8$ alkyl, $C_1$-$C_8$ alkenyl, $C_1$-$C_8$ alkanol, $C_1$-$C_8$ alkoxy, and where zero or two, but no more than two, vicinal K's in the molecule represent single electrons which form a pi bond, thus forming a double bond together with the existing sigma bond between the two adjacent carbons bearing the two vicinal K's, or a salt, stereoisomer or tautomer thereof.

14. A compound according to claim 13 of the formula

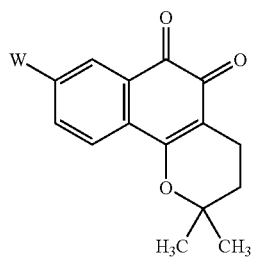

wherein W is selected from —OH, —O—$C_1$-$C_8$ alkyl, —O—$C_1$-$C_8$ alkyl-NH$_2$, and —O—$C_1$-$C_8$ alkyl-NH—S, and wherein S is a single amino acid or a peptide of two or more amino acids, or a salt, stereoisomer or tautomer thereof.

15. A compound according to claim 13, wherein W is —O—$C_1$-$C_8$ alkyl-NH—S, wherein S is a single amino acid or a peptide of two or more amino acids; wherein the group —NH— forms an amide bond with the alpha-carboxy group of S when S is a single amino acid and the group —NH— forms an amide bond with the C-terminal alpha-carboxy group of S when S is a peptide of two or more amino acids, or a salt, stereoisomer or tautomer thereof.

16. A compound according to claim 14, wherein W is —O—$C_1$-$C_8$ alkyl-NH—S, wherein S is a single amino acid or a peptide of two or more amino acids; wherein the group —NH— forms an amide bond with the alpha-carboxy group of S when S is a single amino acid and the group —NH— forms an amide bond with the C-terminal alpha-carboxy group of S when S is a peptide of two or more amino acids, or a salt, stereoisomer or tautomer thereof.

17. A compound according to claim 14 of the formula:

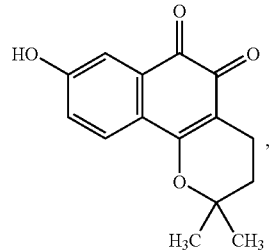

or a salt, stereoisomer or tautomer thereof.

18. A method of treating cancer in an individual, comprising administering a therapeutically effective amount of a compound of claim 14 to the individual.

19. The method of claim 18, wherein the cancer is prostate cancer.

20. A method of treating cancer in an individual, comprising administering a therapeutically effective amount of a compound of claim 17 to an individual.

21. The method of claim 20, wherein the cancer is prostate cancer.

* * * * *